(12) United States Patent
Brockway

(10) Patent No.: US 9,294,074 B2
(45) Date of Patent: *Mar. 22, 2016

(54) PHYSIOLOGICAL SIGNAL DENOISING

(71) Applicant: VivaQuant LLC, St. Paul, MN (US)

(72) Inventor: Marina Brockway, St. Paul, MN (US)

(73) Assignee: VivaQuant LLC, St. Paul, MN (US)

(*) Notice: Subject to any disclaimer, the term of this patent is extended or adjusted under 35 U.S.C. 154(b) by 136 days.

This patent is subject to a terminal disclaimer.

(21) Appl. No.: 14/156,219

(22) Filed: Jan. 15, 2014

(65) Prior Publication Data

US 2014/0136585 A1    May 15, 2014

Related U.S. Application Data

(63) Continuation of application No. 12/938,995, filed on Nov. 3, 2010, now Pat. No. 8,632,465.

(60) Provisional application No. 61/257,718, filed on Nov. 3, 2009, provisional application No. 61/366,052, filed on Jul. 20, 2010.

(51) Int. Cl.
| | |
|---|---|
| *A61B 5/0452* | (2006.01) |
| *H03H 17/02* | (2006.01) |
| *G06F 17/14* | (2006.01) |
| *A61B 5/04* | (2006.01) |
| *G06K 9/00* | (2006.01) |
| *A61B 5/00* | (2006.01) |

(52) U.S. Cl.
CPC ........ *H03H 17/0248* (2013.01); *A61B 5/04017* (2013.01); *A61B 5/0452* (2013.01); *G06F 17/14* (2013.01); *G06K 9/0051* (2013.01); *G06K 9/0053* (2013.01); *A61B 5/7253* (2013.01)

(58) Field of Classification Search
None
See application file for complete search history.

(56) References Cited

U.S. PATENT DOCUMENTS

| | | | |
|---|---|---|---|
| 5,090,418 | A | 2/1992 | Squires et al. |
| 5,521,851 | A | 5/1996 | Wei et al. |
| 5,792,065 | A | 8/1998 | Xue et al. |
| 5,817,027 | A | 10/1998 | Arand et al. |
| 5,827,195 | A | 10/1998 | Lander |
| 5,987,352 | A | 11/1999 | Klein et al. |

(Continued)

FOREIGN PATENT DOCUMENTS

WO    2013/043157 A2    3/2013

OTHER PUBLICATIONS

Tsalaile, et al. "Blind Source Extraction of Heart Sound Signals From Lung Sound Recordings Exploiting Periodicity of the Heart Sound," ICASSP 2008 IEEE, p. 461-464.

(Continued)

*Primary Examiner* — Brian T Gedeon
(74) *Attorney, Agent, or Firm* — Crawford Maunu PLLC

(57) ABSTRACT

Physiological signals are denoised. In accordance with an example embodiment, a denoised physiological signal is generated from an input signal including a desired physiological signal and noise. The input signal is decomposed from a first domain into subcomponents in a second domain of higher dimension than the first domain. Target subcomponents of the input signal that are associated with the desired physiological signal are identified, based upon the spatial distribution of the subcomponents. A denoised physiological signal is constructed in the first domain from at least one of the identified target subcomponents.

29 Claims, 23 Drawing Sheets

(56) References Cited

U.S. PATENT DOCUMENTS

| | | | |
|---|---|---|---|
| 6,389,308 B1 | 5/2002 | Shusterman | |
| 6,589,189 B2 | 7/2003 | Meyerson et al. | |
| 6,690,959 B2 | 2/2004 | Thompson | |
| 6,701,170 B2 | 3/2004 | Stetson | |
| 6,822,564 B2 | 11/2004 | Al-Ali | |
| 7,096,060 B2 | 8/2006 | Arand et al. | |
| 7,115,096 B2 | 10/2006 | Siejko et al. | |
| 7,236,819 B2 | 6/2007 | Brockway et al. | |
| 7,272,265 B2 | 9/2007 | Kouri et al. | |
| 7,376,453 B1 | 5/2008 | Diab et al. | |
| 7,395,114 B2 * | 7/2008 | Czygan et al. | 607/6 |
| 7,627,369 B2 | 12/2009 | Hunt | |
| 7,672,717 B1 | 3/2010 | Zikov et al. | |
| 7,840,259 B2 | 11/2010 | Xue et al. | |
| 8,086,304 B2 | 12/2011 | Brockway et al. | |
| 8,201,330 B1 | 6/2012 | Rood et al. | |
| 8,214,007 B2 | 7/2012 | Baker et al. | |
| 8,271,073 B2 | 9/2012 | Zhang et al. | |
| 8,348,852 B2 | 1/2013 | Bauer et al. | |
| 8,460,189 B2 | 6/2013 | Libbus et al. | |
| 8,478,389 B1 | 7/2013 | Brockway et al. | |
| 2005/0010120 A1 | 1/2005 | Jung et al. | |
| 2005/0234361 A1 | 10/2005 | Holland | |
| 2005/0283090 A1 | 12/2005 | Wells | |
| 2007/0219453 A1 | 9/2007 | Kremliovsky et al. | |
| 2007/0219455 A1 | 9/2007 | Wong et al. | |
| 2007/0260151 A1 | 11/2007 | Clifford | |
| 2007/0265508 A1 | 11/2007 | Sheikhzadeh-Nadjar | |
| 2008/0065158 A1 | 3/2008 | Ben-Ezra et al. | |
| 2008/0097537 A1 | 4/2008 | Duann et al. | |
| 2008/0183093 A1 | 7/2008 | Duann et al. | |
| 2008/0200832 A1 | 8/2008 | Stone | |
| 2009/0069703 A1 | 3/2009 | Takla et al. | |
| 2009/0222262 A1 | 9/2009 | Kim et al. | |
| 2012/0165691 A1 | 6/2012 | Ting et al. | |
| 2012/0197144 A1 | 8/2012 | Christ et al. | |
| 2012/0232417 A1 | 9/2012 | Zhang | |
| 2013/0109937 A1 | 5/2013 | Banet et al. | |
| 2014/0005988 A1 | 1/2014 | Brockway | |

OTHER PUBLICATIONS

Jungwirth B, Mackensen GB, Blobner M, Neff F, Reichart B, Kochs EF, Nollert G: Neurologic outcome after cardiopulmonary bypass with deep hypothermic circulatory arrest in rats: description of a new model. J Thorac Cardiovasc Surg 2006, 131:805-812.
Kellermann, et al.,"A mobile phone based alarm system for supervising vital parameters in free moving rats," BMC Research Notes 2012, 5:119, Feb. 23, 2012.
http://www.simplehelp. net/2006/09/12/how-to-set-up-outlook-2003-for-email/.
G.-J. Jang, T.-W. Lee and Y.-H Oh, "Single-Channel Signal Separation Using Time-Domain Basis Functions," IEEE Signal Processing Letters, vol. 10, No. 6, pp. 168-171 (Jun. 2003).
T. Blaschke and L. Wiskott, "Cubica: Independent Component Analysis by Simultaneous Third- and Fourth-Order Cumulant Diagonalization," IEEE Transactions on Signal Processing, vol. 52, No. 5, pp. 1250-1256 (May 2004).
D A Clunie, "Extension of an open source DICOM toolkit to support SCP-ECG waveforms," 2nd OpenECG Workshop 2004, Berlin, Germany.
J.-P. Martinez, et. al., "A wavelet-based ECG delineator: Evaluation on standard databases," IEEE transactions on biomedical engineering, vol. 51, No. 4, pp. 57 (2004).
Thomsen, M. B., Verduyn, S. C., Stengl, M., Beekman, J. D., de Pater, G., van Opstal, J., et al. (2004). Increased short-term variability of repolarization predicts d—sotalolinduced torsade de pointes in dogs. Circulation, 110, 2453-2459.
Malik M, Hnatkova K, Batchvarov V, Gang Y, Smetana P, Camm AJ. Sample size, power calculations, and their implications for the cost of thorough studies of drug induced QT interval prolongation. Pacing Clin Electrophysiol. Dec. 2004;27(12):1659-69.

Madalena Costa.et. al. Multiscale entropy analysis of biological signals. Physical Review E 71, 021906 s2005d.
M. Alghoniemy and A. Tewfik, "Reduced Complexity Bounded Error Subset Selection," IEEE Int. Conf. Acoustics, Speech and Signal Processing (ICASSP), pp. 725-728 (Mar. 2005).
S.-C. Tai, C.-C. Sun and W.-C Yan, "2-D ECG Compression Method Based on Wavelet Transform and Modified SPIHT," IEEE Trans. Biomed. Eng., vol. 52, No. 6, pp. 999-1008 (Jun. 2005).
Hamlin RL. Non-drug-related electrocardiographic features in animal models in safety pharmacology. J Pharmacol Toxicol Methods. Jul.-Aug. 2005; 52(1): 60-76.
HJ van der Linde, A van Water, W Loots, B van Dueren, K van Ammel, M Peters and DJ Gallacher. A new method to calculate the beat-to-beat instability of QT duration in drug-induced long QT in anesthetized dogs. Journal of Pharmacological and Toxicological Methods 52 (2005) 168-177.
R. Sameni, MB Shamsollahi, C. Jutten, and M. Babaie-Zadeh, "Filtering Noisy ECG Signals Using the Extended Kalman Filter Based on a Modified Dynamic ECG Model," Computers in Cardiology, pp. 1017-1020 (2005).
M. Blanco-Velasco, B. Weng and KE Barner, "A New ECG Enhancement Algorithm for Stress ECG Tests," Computers in Cardiology, vol, 33, pp. 917-920 (2006).
Chen PC, Lee S, Kuo CD. Delineation of T-wave in ECG by wavelet transform using multiscale differential operator. IEEE Trans Biomed Eng. Jul. 2006;53(7):1429-33.
K. Zhang, L.-W. Chan, "An Adaptive Method for Subband Decomposition ICA", Neural Computation, vol. 18, No. 1, pp. 191-223 (2006).
R. Brychta, "Wavelet analysis of autonomic and cardiovascular signals," PhD Dissertation. Vanderbilt University (Aug. 2006).
M. Aminghafari, N. Cheze, J.-M Poggi, "Multivariate de-noising using wavelets and principal component analysis," Computational Statistics & Data Analysis, 50, pp. 2381-2398 (2006).
Aharon, M. Elad and A. Bruckstein, "K-SVD: An Algorithm for Designing Overcomplete Dictionaries for Sparse Representation," IEEE Transactions on Signal Processing, vol. 54, No. 11, pp. 4311-4322 (Nov. 2006).
Chouakri S.A., et al. ECG signal smoothing based on combining wavelet denoising levels. Asian Journal of Information Technology vol. 5, pp. 667-677. 2006.
Inan, O.T.; Giovangrandi, L.; Kovacs, G.T.A.; Robust Neural-Network-Based Classification of Premature Ventricular Contractions Using Wavelet Transform and Timing Interval Features , IEEE Transactions on Biomedical Engineering vol. 53 , Issue: 12 , pp. 2507-2515.
L. Smith, A tutorial on Principal Components Analysis.
Akinori Ueno, et al. Capacitive sensing of electrocardiographic potential through cloth from the dorsal surface of the body in a supine position: a preliminary study. IEEE Transactions on Biomedical Engineering, vol. 54, No. 4, Apr. 2007, pp. 759-766.
K. Oweiss , A. Mason , Y. Suhail , A. Kamboh and K. Thomson, "A Scalable Wavelet Transform VLSI Architecture for Real-Time Signal Processing in High-Density Intra-Cortical Implants", IEEE Trans. Circuits Syst. I, vol. 54, No. 6, pp. 1266-1278 (Jun. 2007).
K. Todros and J. Tabrikian, "Blind Separation of Independent Sources Using Gaussian Mixture Model," IEEE Transactions on Signal Processing, vol. 55, No. 7, pp. 3645-3658 (Jul. 2007).
R. Sameni, M. Shamsollahi, C. Jutten and G. Glifford, "A Nonlinear Bayesian Filtering Framework for ECG Denoising," IEEE Transactions on Biomedical Engineering , vol. 54, No. 12, pp. 2172-2185 (2007).
X. Li, X. X Yao, J. Fox, and J. Jefferys, "Interaction Dynamics of Neuronal Oscillations Analysed Using Wavelet Transforms," Journal of Neuroscience Methods 160, pp. 178-185 (2007).
R Schimpf, Ch Antzelevitch, D Haghi, C Giustetto, A Pizzuti, F Gaita, Ch Veltmann, Ch Wolpert and M Borggrefe. Electromechanical coupling in patients with the short QT syndrome: Further insights into the mechanoelectrical hypothesis of the U wave. Heart Rhythm. Feb. 2008 ; 5(2): 241-245.
Sarkar S, Ritscher D, Mehra R. A detector for a chronic implantable atrial tachyarrhythmia monitor. IEEE Trans Biomed Eng. Mar. 2008;55(3):1219-24.

(56) References Cited

OTHER PUBLICATIONS

M. Malik, K. K Hnatkova, T. Novotny, G Schmidt Subject-specific profiles of QT/RR hysteresis. Am J Physiol Heart Circ Physiol 295:H2356-H2363, 2008.

Akturk, A. and Goldsman, N. (2008) "Electron transport and full-band electron phonon interactions in graphene" J. of Applied Physics 103.

S. Paredes, T. Rocha, P. de Carvalho, and J. Henriques, "Atrial Activity Detection through a Sparse Decomposition Technique," vol. 2, pp. 358-362, 2008 International Conference on BioMedical Engineering and Informatics, 2008.

R. Sameni, C. Jutten and M. Shamsollahi, "Multichannel Electrocardiogram Decomposition Using Periodic Component Analysis," IEEE Transactions on Biomedical Engineering, vol. 55, No. 8, pp. 1935-1940 (Aug. 2008).

O. Adeyemi, et. al., "QA interval as an indirect measure of cardiac contractility in the conscious telemeterised rat: Model optimisation and evaluation," Journal of Pharmacological and Toxicological Methods. 60, pp. 159-166 (2009).

H. Li, R. Li, F. Wang. Multiresolution Subband Blind Source Separation: Models and Methods. Journal of Computers, vol. 4, No. 7 (2009), 681-688.

Afonso, V.X.; Tompkins, W.J.; Detecting ventricular fibrillation. IEEE Engineering in Medicine and Biology Magazine, vol. 14, Issue: 2, pp. 152-159.

Dash S, Chon KH, Lu S, Raeder EA. Automatic real time detection of atrial fibrillation. Ann Biomed Eng. Sep. 2009;37 (9):1701-9. Epub Jun. 17, 2009.

M. Hassan, J. Terrien, B. Karlsson, and C. Marque, "Spatial Analysis of Uterine EMG Signals: Evidence of Increased in Synchronization With Term," Conf Proc IEEE Eng Med Biol Soc, vol. 1, pp. 6296-6299 (Sep. 2009).

R. Yang, Y. Qin, C. Li, G. Zhu, Z. Lin Wang, "Converting Biomechanical Energy into Electricity by a Muscle-Movement—Driven Nanogenerator," Nano Letters, vol. 9, No. 3, pp. 1201-1205 (2009).

J. Piccini, et al, Predictors of sudden cardiac death change with time after myocardial infarction: results from the Valiant trial. European Heart Journal (2009).

J. Lipponen, M. Tarvainen, T. Laitinen, T. Lyyra-Laitinen, and P.A. Karjalainen, "Principal Component Regression Approach for Estimation of Ventricular Repolarization Characteristics," IEEE Trans Biomed Eng., vol. 57, No. 5, pp. 1062-1069 (2010).

S. Hadei, M. Iotfizad. A family of adaptive filter algorithms in noise cancellation for speech enhancement. International Journal of Computer and Electrical Engineering, vol. 2, No. 2, Apr. 2010. 1793-8163.

Allen, M., Tung, V., Kaner, R. (2010) "Honey Carbon: A Review of Graphene" Chem. Rev. 110:132-145.

Attila S. Farkas. et. al. Biomarkers and endogenous determinants of dofetilide-induced torsades de pointes in α1-adrenoceptor-stimulated, anaesthetized rabbits. British Journal of Pharmacology. vol. 161, Issue 7, pp. 1477-1495, Dec. 2010.

HJ van der Linde, B Van Deuren, Y Somers, B Loenders, R Towart and DJ Gallacher, The Electro-Mechanical window: a risk marker for Torsade de Pointes in a canine model of drug induced arrhythmias, British Journal of Pharmacology (2010) 161 1444-1454.

Daubechies I., et al. Synchrosqueezed wavelet transforms: an empirical mode decomposition-like tool. Applied and Computational Harmonic Analysis, vol. 30, Issue 2, Mar. 2011, pp. 243-261.

M. Brockway and R Hamlin, "Evaluation of an algorithm for highly automated measurements of QT interval," Journal of Pharmacological and Toxicological Methods, vol. 64, pp. 16-24 (2011).

http://www.physionet.org/physiobank/database/#ecg.

http://www.physionet.org/physiobank/database/mitdb/.

B. Widrow, et al., "Adaptive noise cancelling: principles and applications," IEEE Proc., vol. 63, No. 12, pp. 1692-1716, Dec. 1975.

H. Boudoulas, YH. Sohn, W. O'Neill, R. Brown, AM. Weissler. The QT greater that QS2 syndrome: a new mortality risk indicator in coronary artery disease. American Journal of Cardiology, vol. 50 (6) pp. 1229-1235 (1982).

G. Moody, W. Muldrow, and R. Mark, "A noise stress test for arrhythmia detectors," Computers in Cardiology, pp. 381-384 (1984).

K. R. Rao and P. Yip, "Discrete Cosine Transform: Algorithms, Advantages, Applications," San Diego, CA: Academic (1990).

J. Woods. Subband Coding, Kluwer Academic Press (1990).

K. Ball, L. Sirovich, and L. Keefe, "Dynamical Eigenfunction Decomposition of Turbulent Channel Flow," International Journal for Numerical Methods in Fluids, vol. 12, Issue 6, pp. 585-604 (Apr. 1991).

NV Thakor and YS Zhu, "Applications of adaptive filtering to ECG analysis: noise cancellation," IEEE Transactions on Biomedical Engineering, vol. 38, No. 8, pp. 785-794 (Aug. 1991).

S. Mallat and W. L.-Hwang, "Singularity Detection and Processing with Wavelets," IEEE Transactions on Information Technology (38), pp. 617-643 (1992).

S. Mallat and S. Zhong, "Characterization of Signals from Multiscale Edges," IEEE Trans. Pattern Anal. Mach. Intell. 14, 7 (Jul. 1992).

Vaidyanathan, Multirate Systems and Filter Banks, Prentice Hall, 1993.

Y. Pati, R. Rezaiifar and P. Krishnaprasad, "Orthogonal Matching Pursuit: Recursive Function Approximation With Applications to Wavelet Decomposition," in Asilomar Conference on Signals, Systems and Computers, vol. 1, pp. 40-44 (Nov. 1993).

S. Mallat and Z. Zhang, "Matching Pursuits with Time-Frequency Dictionaries," IEEE TSP(41), No. 12, pp. 3397-3415 (Dec. 1993).

P. Comon, "Independent component analysis, a new concept?," Signal Process. Special Issue on Higher Order Statistics, vol. 36, No. 3, pp. 287-314 (Apr. 1994).

Donoho, D.L., I.M. Johnstone (1994), "Ideal spatial adaptation by wavelet shrinkage," Biometrika, vol. 81, pp. 425-455.

Y. Xu, J. Weaver, D. Healy, Jr. and J. Lu, "Wavelet Transform Domain Filters: A Spatially Selective Noise Filtration Technique," IEEE Transactions on Image Processing, vol. 3, No. 6, pp. 747-758 (1994).

D. L. Donoho, "Denoising by Soft-Thresholding," IEEE Trans. on Inf. Theory, vol. 41, No. 3, pp. 613-627 (May 1995).

A.Bell and T. Sejnowski, "An Information-Maximization Approach to Blind Separation and Blind Deconvolution," Neural Computation, 7:1129-1159. (1995).

M. Haugland and T. Sinkjaer, "Cutaneous Whole Nerve Recordings Used for Correction of Footdrop in Hemiplegic Man," IEEE Transactions on Rehabilitation Engineering, vol. 3, No. 4. pp. 207-317 (Dec. 1995).

V. Afonso, W. Tompkins, T. Nguyen, K. Michler and S. Luo, "Comparing Stress ECG Enhancement Algorithms," IEEE Engineering in Medicine and Biology, pp. 37-44 (May/Jun. 1996).

J._Francois Cardoso, "Infomax and Maximum Likelihood for Source Separation," IEEE Letters on Signal Processing, vol. 4, No. 4, pp. 112-114 (Apr. 1997).

M. L. Hilton, "Wavelet and Wavelet Packets Compression of Electrocardiogram," IEEE Transactions on Biomedical Engineering, vol. 44, No. 5, pp. 394-402 (May 1997).

A.Hyvärinen, "New Approximations of Differential Entropy for Independent Component Analysis and Projection Pursuit," In Advances in Neural Information Processing Systems, vol. 10, pp. 273-279, MIT Press. (1997).

W. Sweldens. The lifting scheme: A construction of second generation wavelets. SIAM J. Math. Anal., 29(2):511-546, 1997.

American National Standard ANSI/AAMI EC57:1998, Testing and Reporting Performance Results of Cardiac Rhythm and ST Segment Measurement Algorithms.

Testing and reporting performance results of cardiac rhythm and ST-segment measurement algorithms ANSI/AAMI EC57:1998.

L. Torres-Pereira, et. al. "A Biotelemetric Heart Sound Monitoring System," in Proceedings of the 14th International Symposium on Biotelemetry. Marburg, 1998.

A. Hyvärinen, "Fast and Robust Fixed-Point Algorithms for Independent Component Analysis," IEEE Transactions on Neural Networks, vol. 10, No. 3, pp. 626-634 (May 1999).

J.-F. Cardoso, "High-Order Contrasts for Independent Component Analysis," Neural Comput., vol. 11, No. 1, pp. 157-192 (1999).

(56) References Cited

OTHER PUBLICATIONS

S. Chen, D Donoho, and M. Saunders, "Atomic Decomposition by Basis Pursuit," SIAM J. Scientific Computing, vol. 20, No. 1, pp. 33-61 (1999).

Q. Pan, L. Zhang, G. Dai and H. Zhang, "Two Denoising Methods by Wavelet Transform," IEEE Trans. on SP, vol. 47, No. 12, pp. 3401-3406 (Dec. 1999).

G. Michaud, Q. Li, X. Costeas, R. Stearns, M. Estes, and PJ Wang, "Correlation waveform analysis to discriminate monomorphic ventricular tachycardia from sinus rhythm using stored electrograms from implantable defibrillators," PACE. Aug. 1999; 22(8):1146-51 (1999).

S. Mallat, "A Wavelet Tour of Signal Processing," Academic Press, 1999.

Langley, P.; Di Bernardo, D.; Murray, A.; Comparison of three measures of QT dispersion. Computers in Cardiology 1999 pp. 69-72.

Goldberger AL et al. PhysioBank, PhysioToolkit, and PhysioNet: components of a new research resource for complex physiologic signals. Circulation 101(23): e215-e220, 2000 (Jun. 13)

Z. Lu, D. Kim, and W. Pearlman, "Wavelet Compression of ECG Signals by the Set Partitioning in Hierarchical Trees Algorithm," IEEE Transactions on Biomedical Engineering, vol. 47, No. 7, pp. 849-856 (Jul. 2000).

M. Marcellin, M. gormish, A. Bilgin and M. Boleik, "An Overview of JPEG-2000," Proc. of IEEE Data Compression Conference, pp. 523-541 (2000).

L. K. Saul and J. B. Allen, "Periodic component analysis: An eigenvalue method for representing periodic structure in speech," in NIPS, [Online],, pp. 807-813 (2000). Available: http://www.cs.cmu.edu/Groups/NIPS/00papers-pub-on-web/SaulAllen.pdf.

C. Taswell, "The What, How, and Why of Wavelet Shrinkage Denoising," Computing in Science and Engineering, vol. 2, No. 3, pp. 12-19 (2000).

J. S. Richman and J. R. Moorman, Physiological time-series analysis using approximate entropy and sample entropy Am. J. Physiol. 278, H2039 (2000).

K. Sayood, "Introduction to Data Compression," Academic Press 2000.

Malik M, Batchvarov VN. Measurement, interpretation and clinical potential of QT dispersion. J Am Coll Cardiol. Nov. 15, 2000;36(6):1749-66.

A. Hyvärinen and E. Oja, "Independent Component Analysis: Algorithms and Applications," Neural Networks, 13(4-5), pp. 411-430 (2000).

R. Mayerburg. Sudden cardiac death: exploring the limits of our knowledge. Journal of Cardiovascular Electrophysiology, vol. 12, No. 3, Mar. (2001).

M. Brennan, M. Palaniswami, and P. Kamen. Do Existing Measures of Poincaré Plot Geometry Reflect Nonlinear Features of Heart Rate Variability? IEEE Transactions on Biomedical Engineering, vol. 48, No. 11, Nov. 2001.

D. Donoho and X. Huo, "Uncertainty Principles and Ideal Atomic Decomposition," IEEE Transactions on Information Theory, vol. 47, No. 7, pp. 2845-2862 (Nov. 2001).

M. Zibulevsky and B. Pearlmutter, "Blind Source Separation by Sparse Decomposition in a Signal Dictionary," Neural Computation. vol. 13, pp. 863-882 (2001).

Oweiss, K.G. Anderson, D.J. "MASSIT—Multiresolution Analysis of Signal Subspace Invariance Technique: a novel algorithm for blind source separation", Conference on Signals, Systems and Computers Publication Date: 2001 vol. 1, pp. 819-823 vol. 1.

M. Costa, A. L. Goldberger, and C.-K. Peng, Multiscale Entropy Analysis of Complex Physiologic Time Series, Phys. Rev. Lett. 89, 6, (2002).

B. U. Kohler, C. Hennig, R. Orglmeister. The principles of software QRS detection. IEEE Engineering in Medicine and Biology Magazine, vol. 21, No. 1. (2002), pp. 42-57.

Ghasemi, M, SadAbadi, H "A Semi-Automated QT Interval Measurement Based on Wavelet and Energy Analysis," http://physionet.org/challenge/2006/papers/.

Aminghafari, Mina, Cheze, Nathalie, Poggi, Jean-Michel, "Multivariate Denoising using Wavelets and Principal Component Analysis," Computational Statistics and Data Analysis. vol. 50 , pp. 2381-2398, 2006.

SadAbadi H, Ghasemi M, Ghaffari A, "A mathematical algorithm for ECG signal denoising using window analysis," Biomed Pap Med Fac Univ Palacky Olomouc Czech Repub. Jun. 2007;151(1):73-8.

* cited by examiner

Example of atrial activity extraction in an ECG with atrial flutter using an MDSP embodiment Example of Atrial Activity Extracted from an ECG with Atrial Fibrillation Example of Background Noise Removal from a PNA Signal QRS detection performance of an MDSP embodiment on a challenging ECG Example of respiration signal derived from an ECG Three-dimensional ECG image created as an intermediate step in data compression ECG Remote Monitoring System and Rhythm Strip Evaluation Process

PHYSIOLOGICAL SIGNAL DENOISING

RELATED PATENT DOCUMENTS

This patent document is a continuation under 35 U.S.C. §120 of U.S. patent application Ser. No. 12/938,995 filed on Nov. 3, 2010 (U.S. Pat. No. 8,632,465), which claims the benefit under 35 U.S.C. §119 of U.S. Provisional Patent Application Ser. No. 61/257,718 filed on Nov. 3, 2009, and of U.S. Provisional Patent Application Ser. No. 61/366,052 filed on Jul. 20, 2010; each of these patent documents is fully incorporated herein by reference.

FIELD OF INVENTION

Various aspects of the present invention relate to the processing of physiological signals, and more particular aspects relate to removing noise and extracting and compressing information.

BACKGROUND

Implantable and external devices are used to monitor physiologic signals of human and animal subjects. These devices may incorporate various types of sensors and can measure and record signals from those sensors for processing by a system or monitoring center located remote from the subject, or in other cases, the device may perform some or all of the desired signal processing and forward the resulting information to a remote system for display, recording, or further processing.

The signal processing is performed to extract information from the signal in order to assess the physiological condition of the monitored subject and often to evaluate the response of the subject to a therapy or experimental protocol. For example, devices that measure ECG and blood pressure are routinely used to assess cardiovascular function. Clinicians can use this information to make therapy decisions and researchers can use this information to assess the safety and utility of experimental therapies. This information is also used for closed loop control of therapy delivery. In other examples, measurements of peripheral nerve activity (PNA), respiration, blood oxygen, blood glucose, EEG, EMG, heart sounds and blood flow signals are processed to extract information for clinical or research purposes.

There is an increasing reliance on automatic processing to extract information in order to reduce labor and costs and to more consistently and accurately evaluate the condition of the subject. In therapeutic devices automatic extraction of this information is often essential for feedback control. However, accurate automatic extraction of information is often challenging or is compromised by the presence of noise.

In some physiologic signal processing applications, automated analysis is complicated by the fact that measured signals are the result of activity of multiple sources, referred to as multi-source signals. An example of a multi-source signal is ECG measured on the surface of the body where electrical activity is sensed from both the atria and ventricles as well as skeletal muscles. It is useful, for example, to observe atrial activity independent of ventricular activity in order to improve the detection of atrial arrhythmias. Current techniques for providing signal source extraction of multi-source signals, such as independent component analysis (ICA), assume independence of sources and performance is compromised when this assumption is invalid, such as is the case when separating atrial and ventricular activity in an ECG. In addition, ECGs are often recorded from ambulatory subjects using a small number of sensing leads, further complicating signal source extraction due to the mixing of sources inherent in a small number of leads.

Other signals, such as peripheral nerve activity (PNA) and brainstem auditory response, have proven difficult to analyze because of very low signal-to-noise ratio (SNR). Visual analysis of these signals is often inadequate to detect important features and obtain a quantitative evaluation.

Many physiological signal processing techniques have been difficult to successfully implement under certain conditions, particularly when processing signals from ambulatory subjects where the signals are often quite noisy. For example, measurements of ECG parameters such as heart rate, QT interval, PR interval, as well as systolic and diastolic blood pressure may contain errors as a result of the presence of noise. Detection of ventricular and atrial arrhythmias in ECG may have excessive incidence of false positives due to the inability of a signal processing algorithm to provide accurate detection, particularly in the presence of noise. Likewise, the presence of noise may result in inaccurate and inconsistent evaluation of cardiac pathologies that are reflected in ECG morphology. Because of lack of confidence in the accuracy of results, human review has often been used to confirm results or correct errors made by automated analysis algorithms.

Inaccuracies in performance can also result in excess telecom costs when monitoring ambulatory subjects. For example, some types of ambulatory ECG monitoring devices employ on-board signal processing to detect arrhythmias and forward the detected arrhythmias to a monitoring center where they are further processed and reviewed by a human being using a data review system. Because of limitations in existing algorithms, there is a high rate of false positive arrhythmia detections in the ambulatory device that results in a high volume of data transmitted from the patient to a monitoring center. This results in excessive telecommunications expense, the need for additional memory in the ambulatory monitoring device, and additional expense to manually review the data received at the monitoring center.

Various methods of data compression are also limited in their ability to provide high levels of compression with minimal signal distortion in part due to the presence of noise. More efficient data compression can reduce the volume of data that must be stored in memory on an ambulatory monitoring device as well as reduce the volume of data transmitted from the monitored subject. In certain applications, this can result in a reduction in telecom expense and a reduction in power consumption in the ambulatory monitoring device, leading to a reduction in the device size and extension of battery life.

The presence of noise in physiological signals can be a limiting factor in providing accurate and consistent computerized evaluations and extraction of information, but the removal of noise has been complicated by the fact that the noise often has spectral content that falls within the bandwidth of the signals of interest (referred to as in-band noise). For example atrial signals can be contaminated by electrical activity of the ventricle, and ECG signals can be contaminated by EMG from the skeletal muscles. The plethora of signal sources contained within a limited number of channels measured in a surface ECG, with each channel containing mixed interdependent signals, renders problematic the independent observation of the sources of these multisource signals. This problem is further complicated when signals are acquired from closely spaced electrodes and are contaminated by noise, as is usually the case when monitoring patients outside a clinic or hospital. This characterization is not only common to electrocardiogram (ECG) signals acquired with surface or subcutaneous leads but is also common to electrograms (EGM) measured with intracardiac leads, blood pressure signals, pulse oximetry signals, peripheral nerve activity (PNA) recordings, signals representing non-invasive measurements of intracranial pressure, and other physiologic signals collected from ambulatory subjects. Current filtering techniques such as bandpass filtering are effective in removing noise without distorting the signal when the spectral content of the noise and signal are separated in the frequency domain. Many filtering techniques capable of removing in-band noise, such as independent component analysis require that noise and signal content are uncorrelated and independent, an inaccurate assumption for most physiological signals.

Removing at least some of the in-band noise, or denoising, of physiological signals can be useful in the improvement of accuracy of computerized evaluations and has been an objective of many prior efforts. However, the success of many prior efforts has been limited. Various techniques have also been limited in their ability to report characteristics of information derived by an algorithm relative to noise, artifact, or signal morphology changes. These and other matters have presented challenges to the design and implementation of devices, systems and methods for processing physiological signals.

SUMMARY

Various aspects of the present invention are directed to devices, methods and systems involving physiological signal processing, in a manner that addresses challenges and limitations including those discussed above.

In accordance with various example embodiments, a physiological signal is denoised. In various implementations, denoising is carried out using techniques including those referred to herein as Multi-Domain Signal Processing (MDSP), for which a multitude of exemplary embodiments are described. The captured signal is received in a first domain and is decomposed into subcomponents in a second domain of higher dimension than the first domain. The resulting subcomponents in the second domain are processed based upon the spatial distribution of the subcomponents using, for example, spatially selective filtering or principal component analysis to identify those subcomponents that are primarily associated with noise in a time segment. Subcomponents identified as primarily associated with noise are removed and the remaining subcomponents are combined to reconstruct a denoised signal in the first domain.

Another example embodiment is directed to a method for computing a denoised physiological signal from an input signal including a desired physiological signal and noise. The input signal is decomposed from a first domain into subcomponents of the input signal in a second domain of higher dimension than the first domain. From the decomposed subcomponents, target subcomponents of the input signal that are associated with the desired physiological signal are identified based upon the spatial distribution of the subcomponents. A denoised physiological signal is constructed in the first domain from at least one of the identified target subcomponents.

Another example embodiment is directed to a method for reducing the power of an undesired signal in a recording of a quasi-periodic mammalian physiological signal containing desired components and undesired components. A transform is used to decompose the physiological signal into subcomponents representing the signal in a time-frequency domain. At least two time windows are identified in a cycle of the signal, each time window having a different band of frequencies associated with desired components of the signal. In the at least two time windows, ones of the subcomponents associated with the desired signal components are identified as subcomponents having spectral content overlapping a band of frequencies associated with desired signal components within said at least two time windows. A denoised physiological signal is constructed using at least one of the identified subcomponents within each of the at least two time windows.

In another aspect of the present invention, a dynamic signal-to-noise ratio is computed as the ratio of power contained in the subcomponents primarily associated with signal and subcomponents primarily associated with noise.

In another aspect of the present invention, the subcomponents associated with a signal wave of a physiological signal are denoised and are combined to form a denoised emphasis signal of the signal wave. The emphasis signal is subsequently evaluated to identify feature points of the signal wave.

In another aspect of the present invention, feature points of signal waves are evaluated to detect clinically significant events and signal morphology characteristics.

In another aspect of the present invention, a validity metric, computed as a function of a dynamic signal-to-noise ratio and signal morphology characteristics, is used to assess the accuracy, consistency, and validity of feature points, morphology characteristics, and detected events.

In yet another aspect of the present invention, the denoised signal or its subcomponents and detected features are used to facilitate signal compression to reduce stored and communicated data volume.

In yet another aspect of the present invention, signal compression and feature and event detection improvements are used to implement a device of reduced size and enhanced performance.

The above summary is not intended to describe each embodiment or every implementation of the present disclosure. The figures and detailed description that follow more particularly exemplify various embodiments.

BRIEF DESCRIPTION OF THE DRAWINGS

The invention may be more completely understood in consideration of the following detailed description of various embodiments of the invention in connection with the accompanying drawings, in which:

FIG. 3 shows scatter plots, in which

Figure 1:
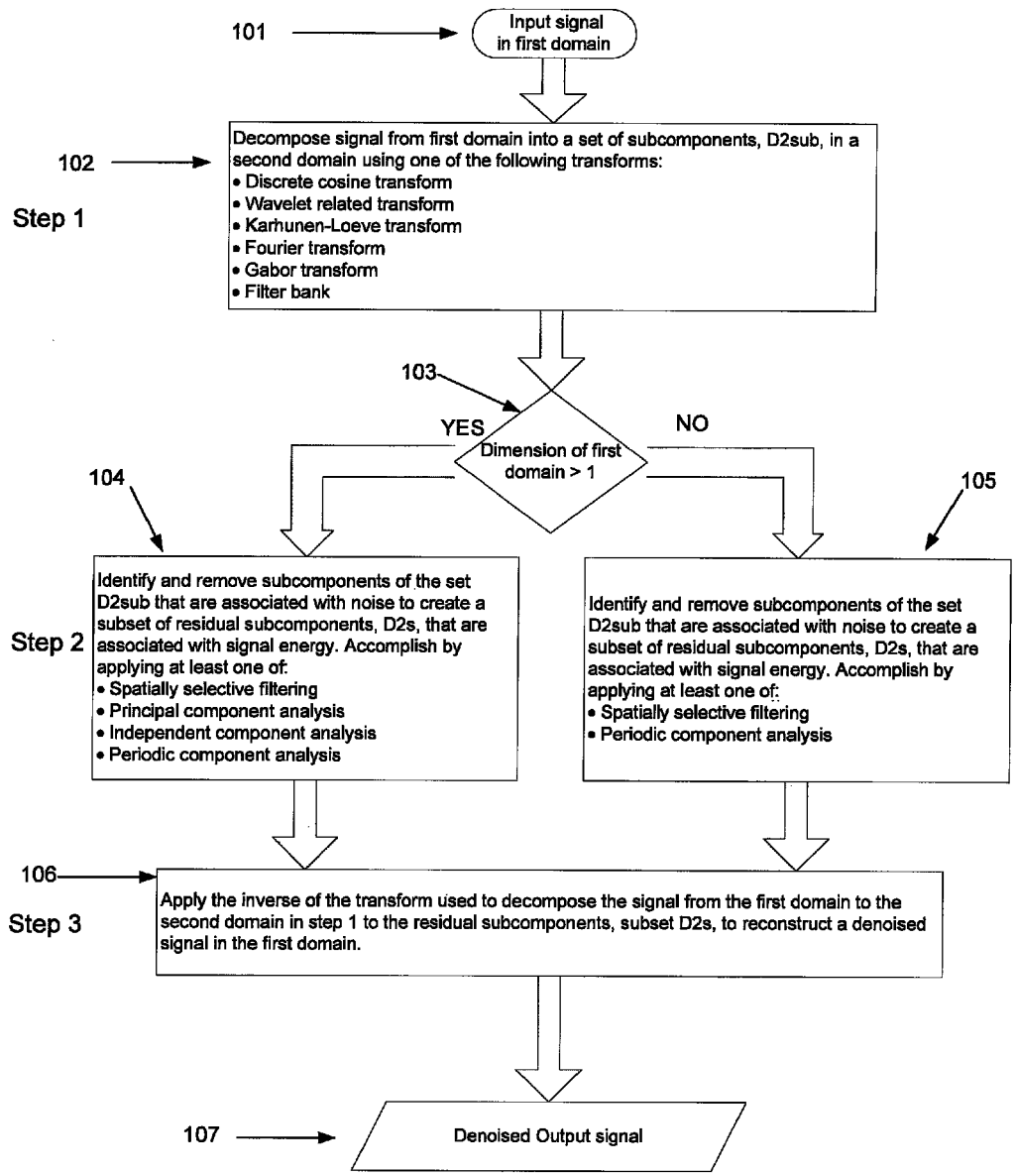
FIG. 1 shows a data flow diagram of Multi-Domain Signal Processing applied to denoising a captured signal, consistent with an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the invention including aspects defined in the claims.

DETAILED DESCRIPTION

Various example embodiments of the present invention relate to the processing of physiological signals, and in many implementations, to reduce noise, extract information, characterize signals, and/or compress the volume of data. While the present invention is not necessarily limited to such applications, various aspects of the invention may be appreciated through a discussion of examples using this context.

Many embodiments described here are broadly referred to as including an approach referred to as "Multi-Domain Signal Processing" (MDSP), for which many different embodiments are described by way of example. In connection with various embodiments, the term Multi-Domain Filtering (MDF) is used herein to refer to embodiments that use one or more MDSP-based embodiments to denoise physiologic signals. Various embodiments are also directed to processing a broad range of physiological signals including but not limited to signals corresponding to ECG, blood pressure, respiratory, heart sounds, EEG, peripheral nerve activity, atrial activity, temperature, photoplethysmography, tissue impedance, blood glucose, and EMG. Different embodiments are further directed to one or more of: improving the accuracy and consistency of information provided under a broad range of use scenarios, extending battery life of monitoring devices, providing a desirably-sized monitoring device (e.g., a reduced, or small size), and improving and/or reducing the need for human review of analysis results and the associated expense of doing so.

In the following discussion, reference is made to cited references listed in a numbered order near the end of this document, which are fully incorporated herein by reference. These references may assist in providing general information regarding a variety of fields that may relate to one or more embodiments of the present invention, and further may provide specific information regarding the application of one or more such embodiments.

According to an example embodiment, physiological signals of a subject are captured by an implantable or external device. This device can be implemented as a part of a system that measures, processes, and evaluates physiological data from animal or human subjects for research, therapy titration, diagnosis, or delivery of medical care. The device may temporarily store the processed signals for later transmission to a system remote from the subject for further processing, display, and reporting to a medical care provider or researcher. The processed signals may be transmitted in real time or they may be used within a therapy delivery device as part of a system to control or advise administration of a therapy. In yet another embodiment, unprocessed or partially processed signals may be transmitted to a device or system located outside the body of the subject for processing, display, review, reporting, or retransmission to another system.

In many applications, physiological signals processed in accordance with the embodiments discussed herein are multisource signals, meaning that the signal observed by electrodes or leads includes components that are the result of many physiological processes and sources that are often interdependent. For example, an ECG signal measured at the surface of the body may include signals emanating from sources such as the atria, ventricles, electrical noise (e.g., from sources outside the body), noise from muscular electrical activity, signals resulting from pathologies such as conduction defects, scars in tissue from myocardial infarction, ischemia resulting from reduced blood flow to a region of the heart, and other representative examples. In these and other contexts, various embodiments of the present invention are directed to addressing challenges relative to the analysis of ECG signals, such as those that benefit from independent analysis for denoising and evaluation of cardiac function.

The terms "quasi-periodic", "signal wave", "feature point", "parameter", and "event" are used in connection with the discussion of various embodiments as follows. The term quasi-periodic refers to a periodic signal with a period and with a cycle length that varies with time, and a signal wave is a particular portion or aspect of a period of a physiological signal. For example, an ECG signal may include signal waves referred to as P, Q, R, S, T and U waves. Another example signal wave is the QRS complex portion of an ECG (e.g., the portion of an ECG signal corresponding to the depolarization of the left and right ventricles). In an arterial pressure signal, the dicrotic notch is a signal wave.

Regarding the term "feature point," many physiological signals can be characterized as having features and parameters. A feature point is an identified point within a physiological signal, which may be useful for characterizing the signal and related characteristics of the signal's source. For instance, in heart-related signals, such as ECG, arterial pressure, and blood flow, most cardiac cycles have a feature point or points of interest. Examples include a point corresponding to the onset of the Q-wave (e.g., Q-wave onset) or offset of the T-wave (e.g., T-wave offset) in an ECG or systole in an arterial blood pressure signal. Each of these feature points is described by time of occurrence and amplitude, and consecutive feature points can be combined to form a feature signal.

With respect to the term "feature point," it is sometimes useful to combine feature points over a predetermined period of time, referred to as a feature signal, to compute a parameter. For example, systole feature points can be combined to compute a mean systolic pressure. Computing a parameter can have the effect of reducing or eliminating short-term physiological fluctuations (e.g., changes with respiration) in the feature signal that are not of interest to the user.

Regarding the term "event," physiological signals may include information that can be used for identifying the onset and offset of an event, or simply the fact that an event occurred. For example, when monitoring the ECG of a subject it may be useful to know that an arrhythmic event such as ventricular tachycardia or atrial fibrillation has occurred. In additional embodiments, information is combined from multiple signals to compute features and parameters. For example, the QA interval (the time difference between Q-wave onset and the upstroke of an arterial pressure wave) can be used as a surrogate for cardiac contractility, and employs both a pressure and an ECG signal from a subject. QA interval feature points are computed for a cardiac cycle, can be used to create a feature signal, and averaged over a predetermined period of time to create a QA parameter.

Regarding the terms referring to a "desired physiological signal," such a signal refers to a signal that is to be extracted. This signal may correspond, for example, to a physiological signal within an input signal that includes the physiological signal and noise. In this context, the noise may also include a physiological signal that is not the desired physiological signal. For instance, where a desired physiological signal is an ECG signal from a subject's heart, other physiological signals included with an input signal, such as a respiratory signal, are not desirably extracted.

A "captured signal" is a signal that is sensed and recorded (e.g., digitized), and may also be conditioned. Conditioning of the signal may involve amplification and the application of a filter to remove much of the noise that is outside the bandwidth of the signal. Following digitization, additional filtering may be applied to further remove noise from outside the signal bandwidth, typically using linear filtering techniques such as a finite impulse response filter. A "denoised" signal is a captured signal that has been processed to remove noise, such as by removing undesirable signal components or subcomponents having spectral content within a bandwidth of a selected (e.g., target or desired) signal, or in-band noise. Denoising can be useful for rendering clarity to the desired signal as a result of suppression of undesired signal components (e.g., noise), hence making the desired signal more suitable for analysis.

In accordance with other example embodiments of the present invention, in-band noise of a physiological signal is reduced using a technique involving a multi-domain filtering-type of approach, referred to in connection with various embodiments as MDF. Resulting signals are thus denoised, in the context that at least some noise components in the physiological signal have been removed, relative to the resulting signal (e.g., as re-generated from components of the physiological signal, in a different domain). In one embodiment, signals captured in a first domain are decomposed into subcomponents in a second domain of higher dimension than the first domain. To remove in-band noise from the captured physiological signal, the subcomponents in the second domain are processed based on their spatial distribution using, for example, spatially selective filtering or principal component analysis to identify those subcomponents that are primarily associated with noise at an instant in time. Those subcomponents that are identified as primarily associated with noise are removed and the residual subcomponents (those not having been removed) are combined to reconstruct a denoised signal in the first domain. A subcomponent occurring in a time window within a cycle of the pseudo-periodic signal is said to be associated with a signal if it contains frequencies within a band that has previously been characterized as being present in the signal. A subcomponent within a time segment is considered to be primarily associated with noise if the energy associated with the signal is attributed primarily (e.g., more than half) to noise. In some embodiments, a larger tolerance for noise is set, to permit signals with larger noise content to be processed without distorting the signal (e.g., where a desired signal is expected to include a substantial portion of noise). Under such conditions, processing of the detected signal can be carried out with the understanding that noise forms a majority of the power in the subcomponent. In some implementations, a signal is treated as primarily associated with noise when at least about 60% of the signal's energy at that time segment is noise energy. Likewise, a subcomponent within a time segment is considered to be primarily associated with signal if at least half or more (e.g., 60%) of its energy is within the band of frequencies characterized as being present in the signal.

In the context of various embodiments, references to the removal of subcomponents may not involve any removal or modification of the subcomponents, but rather involve a selective combination of those subcomponents that have been determined to be desirable. For example, for a physiological signal having various subcomponents, certain components can be identified as likely representing components of a signal corresponding to a particular physiological characteristic that is to be analyzed. These identified (desirable) components can be selectively combined, leaving behind other subcomponents. In this context, undesirable subcomponents are not necessarily removed, but rather, have not been used when forming a recombined signal corresponding to a received physiological signal.

The subcomponents that result from decomposition in Multi-Domain Signal Processing (MDSP) embodiments are also used in other aspects of physiologic signal processing, for various embodiments. A characteristic of MDSP is that a signal wave in a multisource physiological signal can be represented using a small number of subcomponents that contain most of the energy of the signal wave. For example, in an ECG decomposed using a discrete wavelet transform, a group of 3 subcomponents may contain most of the energy found in the P-wave of an ECG while most of the energy of a QRS complex may be contained in 4 subcomponents. A subcomponent or its time segment containing a significant amount of energy of a signal at that time segment is said to be associated with the signal at that time segment. As applicable here, a significant amount of energy of a subcomponent is an amount of energy, corresponding to the time segment, that is at least half of the total energy of the signal during the time segment. In various implementations, a subcomponent may be associated with more than one signal wave.

Subcomponents or their time segments associated with a signal wave can be identified, isolated, and used to construct a signal wave independent of other signal waves in a multisource signal. For example, subcomponents associated with a P-wave of an ECG can be identified within the second domain independent of ventricular electrical activity, and used to reconstruct a denoised signal representative of atrial activity. Another group of subcomponents is associated with the T-wave of an ECG, and are used in the extraction of repolarization activity. Signal source extraction of the signal subcomponents in a multisource signal can lead to more accurate analysis and evaluation of certain physiological functions. Another embodiment involving signal source extraction is directed to the extraction of fetal ECGs from ECG signals captured from a pregnant female. Yet another example embodiment is directed to extracting an oxygen saturation signal from a photoplethysmography signal.

Subcomponents can also be used to compute a denoised emphasis signal that exaggerates the features of particular signal waves to facilitate the identification and detection of feature points. For example, subcomponents associated with the T-wave of an ECG can be identified and used to compute a denoised emphasis signal that exaggerates the T-wave relative to other ECG signal waves to facilitate accurate and consistent detection of T-wave offset.

In some embodiments, physiological signal subcomponents are used to compute a dynamic signal-to-noise ratio (dSNR) that represents the ratio of signal energy relative to noise energy on a sample-by-sample basis, or longer period of time such as for one or more cardiac cycles of an ECG. The dSNR can be used for computing a validity signal for assessing the accuracy and reliability of information derived from the captured physiological signal. In some embodiments, the dSNR is used to directly assess the accuracy and reliability of derived information. If dSNR for a cardiac cycle or a portion of a cardiac cycle is low, for example, certain information derived from the ECG for that cardiac cycle may not be accurate and, if it is very low, a cardiac cycle may be uninterpretable.

MDF denoising and other aspects of one or more MDSP-based embodiments are directed to facilitating the efficient compression of physiological signals, which can be used to reduce the volume of data corresponding to sensed signals. Reducing the amount of data (e.g., by eliminating or omitting noise) serves to help the efficient storage of data, and also to reduce the amount of data needed in communications which can be helpful, for example, to simplify wireless transmission protocol. For example, various MDSP-based embodiments involve compressing ECG signals at compression rates of 15:1 to 20:1 (e.g., relative to an original physiological signal prior to denoising) with minimal signal distortion. An MDSP approach is used to achieve accurate identification of cardiac cycles of a denoised ECG, and significantly reduce in-band noise. These identification and denoising approaches are used in connection with one or more of a variety of compression algorithms, in accordance with various embodiments, together with identified redundancies in adjacent cardiac cycles to achieve efficient compression.

In some embodiments, an MDF-based approach is used to remove noise from peripheral nerve activity (PNA) signals and facilitate the accurate quantification of PNA. In these and/or other embodiments, an MDSP-based approach is used across a broad range of physiological signal processing applications with related processing without necessarily relying upon assumptions regarding the independence of signal and noise sources, and/or based upon an assumption (for processing) that physiological signals being processed are quasi-periodic signals.

In the following discussion, reference is made to various documents or other references listed near the end of this patent document, by numerals within square brackets. The information in the documents/references to which these numerals refer may be implemented in connection with one or more example embodiments, and are fully incorporated herein by reference.

Various embodiments are directed to processing signals from ambulatory subjects under conditions in which noise is common and measurements are often obtained using a limited number of closely-spaced electrodes, or a single cannulation of a vessel, such as in the case of blood pressure measurements. Such signals often include aspects of signals emanating from multiple sources that are generally interdependent. For example, heart activity in an atrial chamber usually initiates activity in a ventricular chamber. Statistically, this situation is characterized by mutual dependency of signal sources contaminated by noise. This violates a central assumption of independence of sources that is fundamental to successful application of many current techniques used to separate signal source and noise in multisource signals, such as independent component analysis (ICA) [1]. Various embodiments are directed to processing related signals, without necessarily assuming such independence, to obtain a denoised signal for a desired signal (i.e., a signal corresponding to a characteristic to be detected). The problem of extracting source signals from the multisource physiological signals contaminated with noise can be expressed mathematically as:

$$x(t) = As(t) + n(t) \quad (1)$$

where $s(t) = (s_1(t), \ldots, s_P(t))$ is a vector of source signals that are mixed together by an unknown mixing matrix A of size M×P, where M is a number of observed signals and P is a number of source signals and additive noise $n(t) = (n_1(t), \ldots, n_P(t))$. The extraction of source signals is achieved by estimating the inverse of a mixing matrix A and computing the denoised and separated signals $s(t) = (s_1(t), \ldots, s_P(t))$ from the observed signals $x(t) = (x_1(t), \ldots, x_M(t))$ according to the formula $s(t) = A^{-1}x(t) - A^{-1}n(t)$. When the number of leads M is less than the number of sources P, which is most often the case in physiologic monitoring, the mixing matrix $A_{M \times P}$ is underdetermined. In addition, the sources that make up multisource physiological signals are often not independent. In this situation the matrix $A_{M \times P}$ is not invertible, rendering it difficult to estimate an inverse of the M×P mixing matrix and recover unmixed sources from mixed observations, as is the case when using ICA techniques.

Figure 2:
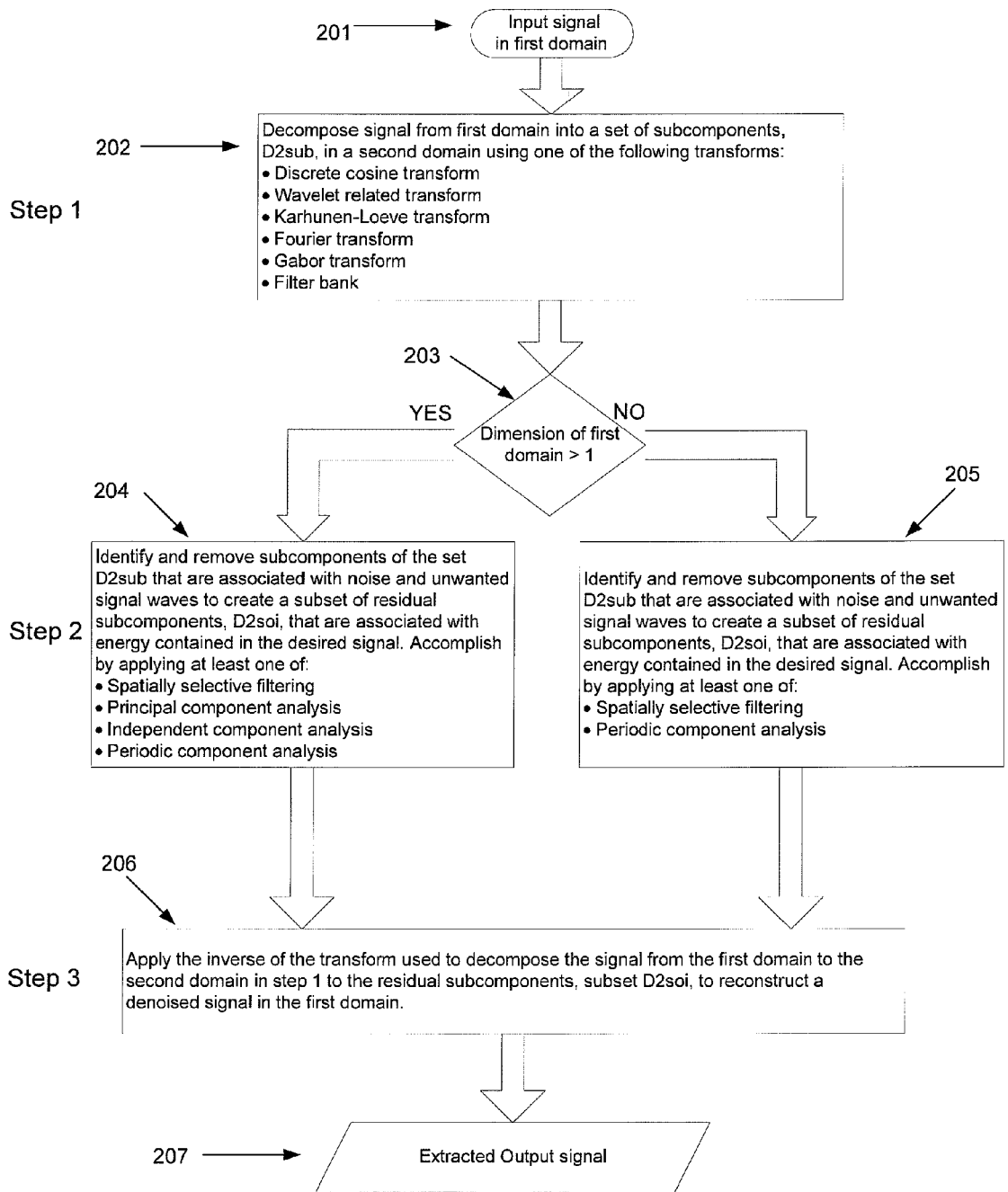
FIG. 2 shows a data flow diagram of Multi-Domain Signal Processing applied to extraction of a signal from a captured physiological signal, consistent with an example embodiment of the present invention.

Turning now to the figures, FIGS. 1 and 2 show signal denoising and signal source extraction, as carried out in a three-step process in accordance with another example embodiment of the present invention. The first step, 102 and 202 in FIGS. 1 and 2 respectively, involves decomposing an input signal 101 and 201 into subcomponents in a second domain of larger dimension than the first domain. Decomposition steps 102 and 202 are performed using one of a variety of transforms that is used for accurate signal reconstruction. Such transforms may involve using, for example, a discrete cosine transform, a wavelet related transform, a Karhunen-Loeve transform, a Fourier transform, a Gabor transform, or a filter bank. In FIGS. 1 and 2, the set of subcomponents resulting from the decomposition steps 102 and 202, respectively is referred to as D2sub. The dimension of the first domain is defined by the number of observed, or captured, signal channels. The dimension of the second domain is defined by the number of channels multiplied by the number of subcomponents in each channel. The second step involves the identification of signal and noise subcomponents in the second domain followed by removal of unwanted subcomponents, including noise.

Referring to FIG. 1, to denoise a desired signal, subcomponents of the set D2sub that are primarily associated with noise are identified and removed to create a subset D2s of residual denoised subcomponents. Referring to FIG. 2, if signal source extraction is performed, such as when an atrial activity signal is extracted from a surface ECG, the subcomponents associated with the signal sources to be extracted are identified and the other subcomponents are removed to create a subset D2soi containing energy associated with the desired signal. In certain embodiments involving both denoising and signal source extraction, subcomponents to be removed are identified based upon their spatial distribution using, for example, Spatially Selective Filtering (SSF) or Periodic Component Analysis (πCA). At decision steps 103 and 203 in FIGS. 1 and 2, the signal is processed at either 104, 204 if the dimension of the first domain is greater than 1, or at block 105/205 if the dimension of the first domain is not greater than one.

If the dimension of the first domain is greater than 1, then SSF, πCA, Principal Component Analysis (PCA), and Independent Component Analysis (ICA) can be used in combination (e.g., as in blocks 104 and 204). If the dimension of the first domain is equal to 1, then SSF or PCA can be used to evaluate the spatial distribution of the subcomponents, as in 105 and 205. Once the subcomponents associated with noise are identified they are effectively removed by setting them to zero. Following removal of the subcomponents associated with noise, the subcomponents are said to be denoised. In the case of signal source extraction, those subcomponents associated with noise and those not associated with a signal source to be extracted are identified and effectively removed by setting them to zero.

In steps 106 and 206, the denoised signal subcomponents, referred to as subset D2s, are reconstructed in the first domain to provide denoised output signal 107 by performing the inverse of the transform used to decompose the signal. If signal source extraction is performed only those subcomponents not removed and identified as associated with the desired signal sources, referred to as subcomponent subset D2soi, are reconstructed into the extracted desired signal 207 in FIG. 2.

Various embodiments directed to MDSP approaches use a mathematical representation of physiological signals as a linear combination of basis functions. Each of these basis functions is chosen to fit a prominent feature, or signal wave, of a signal source. For example, a basis function might represent a type of QRS complex contained in an ECG signal. In one embodiment, decomposition is achieved by representing the observed signals as a linear combination of basis functions, $$s_i(t) = \sum_{k=1}^{K} \varphi_k(t) d_{ik}, i = 1:P, x_i(t) = \sum_{k=1}^{K} \varphi_k(t) c_{ik}, i = 1:M \quad (2)$$

where $d_{ik}$ and $c_{ik}$ are decomposition coefficients or subcomponents. In some embodiments, the elements $\phi_k$ may be mutually dependent and form an overcomplete set referred to as a "dictionary" D. The elements are selected to provide a sparse representation of the signal sources, meaning that most of the decomposition coefficients $d_{ik}$ and $c_{ik}$ in equation (2) are close to or equal to zero. A combination of basis functions or elements of the dictionary forms the second domain.

Higher sparsity provides for greater statistical independence of signal source and noise subcomponents. This property of sparse decomposition is used to facilitate effective identification and extraction of signal source subcomponents and removal of noise. Sparse decomposition, for example, can result in a concentration of signal energy in a relatively small number of large decomposition coefficients while noise is spread out across many basis functions and represented by small decomposition coefficients as described in equation (2).

The sparsity criteria can be used to choose a dictionary that provides for sparse decomposition of the signal sources and hence improved signal source extraction and denoising. In certain embodiments it may be advantageous to choose an over-complete dictionary D in order to increase the degree of sparsity of the decomposition. The examples of dictionaries that are relevant to this embodiment include eigenfunctions [2], wavelet related transforms, including wavelet packets and shift-invariant or stationary wavelets [3], cosine transform [4], Fourier basis [5] or Gabor basis and their combinations [6]. A custom dictionary that achieves a higher degree of sparsity can also be designed by a number of methods for finding basis functions that represent building blocks of the signal [7]. The examples of these methods are matching pursuit [5], orthogonal matching pursuit [8], basis pursuit [9], K-SVD [10], bounded error subset selection [11] or orthogonal subspace pursuit. In general, the dictionary design methods use a representative set of training signals, to find a dictionary that leads to the best representation for each signal wave in this set, under strict sparsity constraints:

$$\min_{D,c}\{\|x - Dc\|_F^2\} \text{ subject to } \|c\|_0 \leq T$$

where $\|.\|_0$ is a $1^0$ norm, counting the nonzero entries of a vector, T is a constraint on the maximum number of non-zero elements allowed, and $\|.\|_F^2$ is a Frobenius norm. For example, a representative set of training signals can be a set of ECG recordings with a broad range of morphologies that include normal sinus rhythm, conduction abnormalities, pathologies, arrhythmias for a particular species. The set should include a sample of each morphology that the algorithm may experience during analysis of an ECG recording of the species. In one embodiment, the custom dictionary is built using the following iterative procedure. A vector is selected from the training set and is represented as a sparse linear combination of initial dictionary elements. This can be accomplished, for example, by finding elements that are maximally correlated with the vector. This subset of elements form a subspace that is decorrelated from the rest of the training set (e.g., by using singular value decomposition (SVD)). The decorrelated subset is added to the dictionary and the elements of the training set that lie in this subspace are removed from the training set. The process is repeated until an error threshold is reached or an allowed number of iterations is exhausted.

In another embodiment decomposition into the second domain is achieved by applying an adaptive filter that automatically selects the frequency bands, or subbands of wavelet filters or a filter bank, in which subcomponents of the signal sources are most independent. Then each subcomponent $x_i$(t), i=1:M, can be represented as a sum of subband signals $$x_i(t) = x_{i,1}(t) + \ldots + x_{i,K}(t) \quad (3)$$

where K is the number of chosen subbands. The filter coefficients can be adaptively tuned to reduce and/or minimize the mutual information and increase independence between the filter outputs as described by Zhang, et al. [12]

In an embodiment involving a wavelet-related transform decomposition, the first decomposition step for an observed signal with M channels into a wavelet-related dictionary D can be formally described as iterative multiplication of the observed signal by an operator matrix $W^j$ with each iteration step j making up a decomposition level. In this embodiment, the operator matrix $W^j$ is a Toeplitz matrix with the entries formed by a wavelet impulse response. The size of the matrix operator $W^j$ is N×N where N is the number of samples of the observed signal. N is greater than both the number of sources P and the number of observed signals M. Wavelets may be used to generate subcomponents having characteristics of both sparse and subband decomposition. In some implementations, a wavelet decomposition is computed via iterative convolution with wavelet filters or filter banks as described by Vaidyanathan[13].

Referring again to FIGS. 1 and 2, another example embodiment is implemented at step 2, for an MDSP-based approach. The statistical independence of at least some subcomponents related to signal sources and noise is leveraged to identify those subcomponents associated with signal sources and those associated with noise. For example, in case of wavelet decomposition, the equation (1) becomes $$W_x^j = A_j W_s^j + W_n^j, j=1:NL+1 \quad (4)$$

where NL is the number of decomposition levels or subbands. The mixing matrix A is indexed by j, denoting that the sources are mixed differently in each subband according to their spectral distribution.

The subcomponents associated with signal sources can be identified based on spatial distribution of subcomponents in time using one of several techniques, many of which involve finding the mixing matrices $A_j$ and then inverting them to calculate the signal source subcomponents. Examples of techniques that are applicable to identification of subcomponents associated with noise and subcomponents associated with signal sources include principal component analysis (PCA), independent component analysis (ICA), periodic component analysis (πCA) techniques and spatially selective filtering as shown in blocks 104 and 105 of FIG. 1 and blocks 204 and 205 of FIG. 2. These techniques can be used separately or in combination to achieve acceptable performance.

When using the PCA technique to identify subcomponents associated with signal sources, an inverse of the mixing matrix $A_j$ is estimated [14, 15] using singular value decomposition or eigenvalue decomposition of the covariance matrix of signal subcomponents.

This PCA approach involves rotating and scaling the data in order to orthogonalize independent subcomponents. The orthogonalized subcomponents with low signal power are often associated with noise and can be removed to achieve denoising. PCA can be used as a preliminary step prior to applying ICA technique.

Figure 3A:
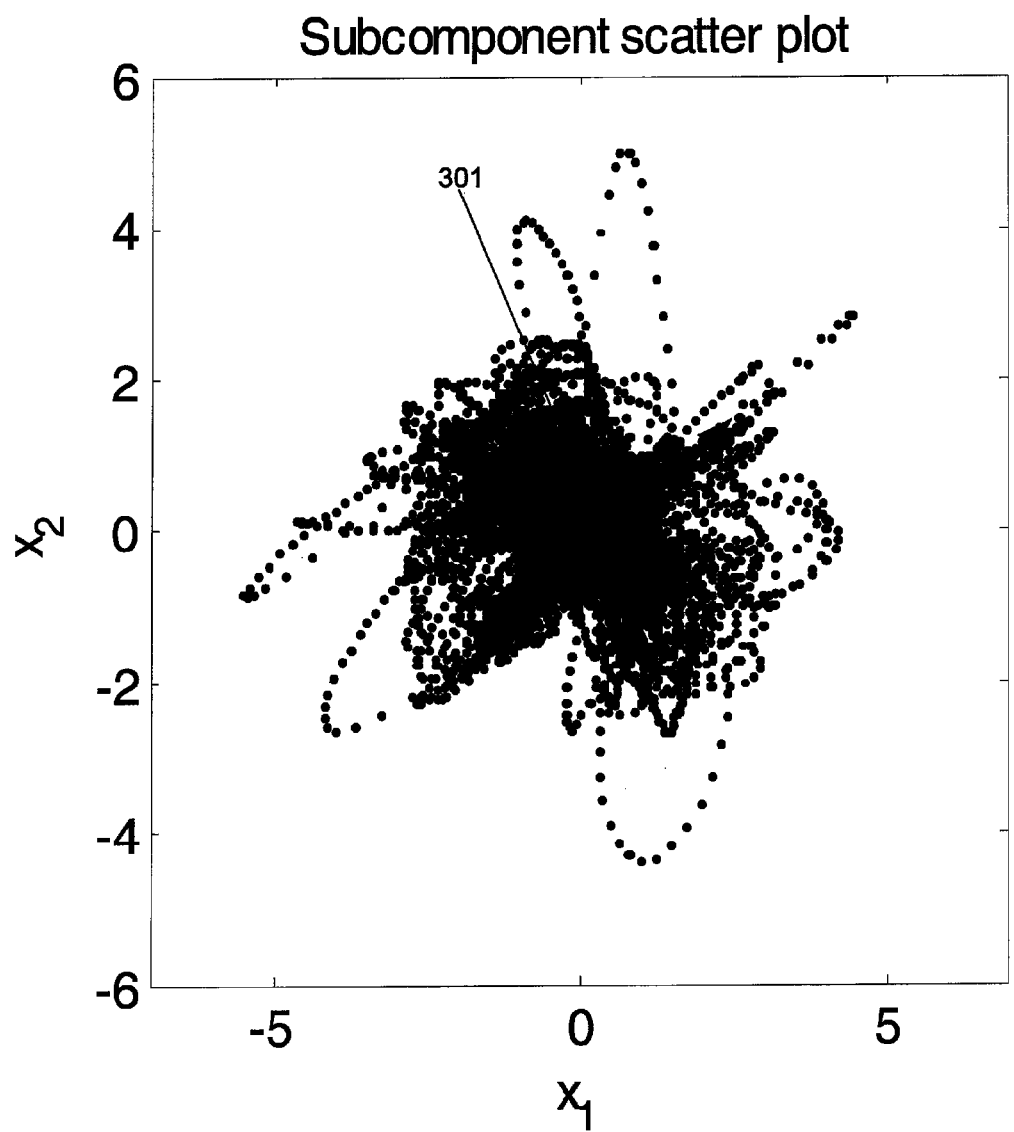
FIG. 3a shows a scatter plot of subcomponents of a noisy signal before application of PCA and ICA.
Figure 3B:
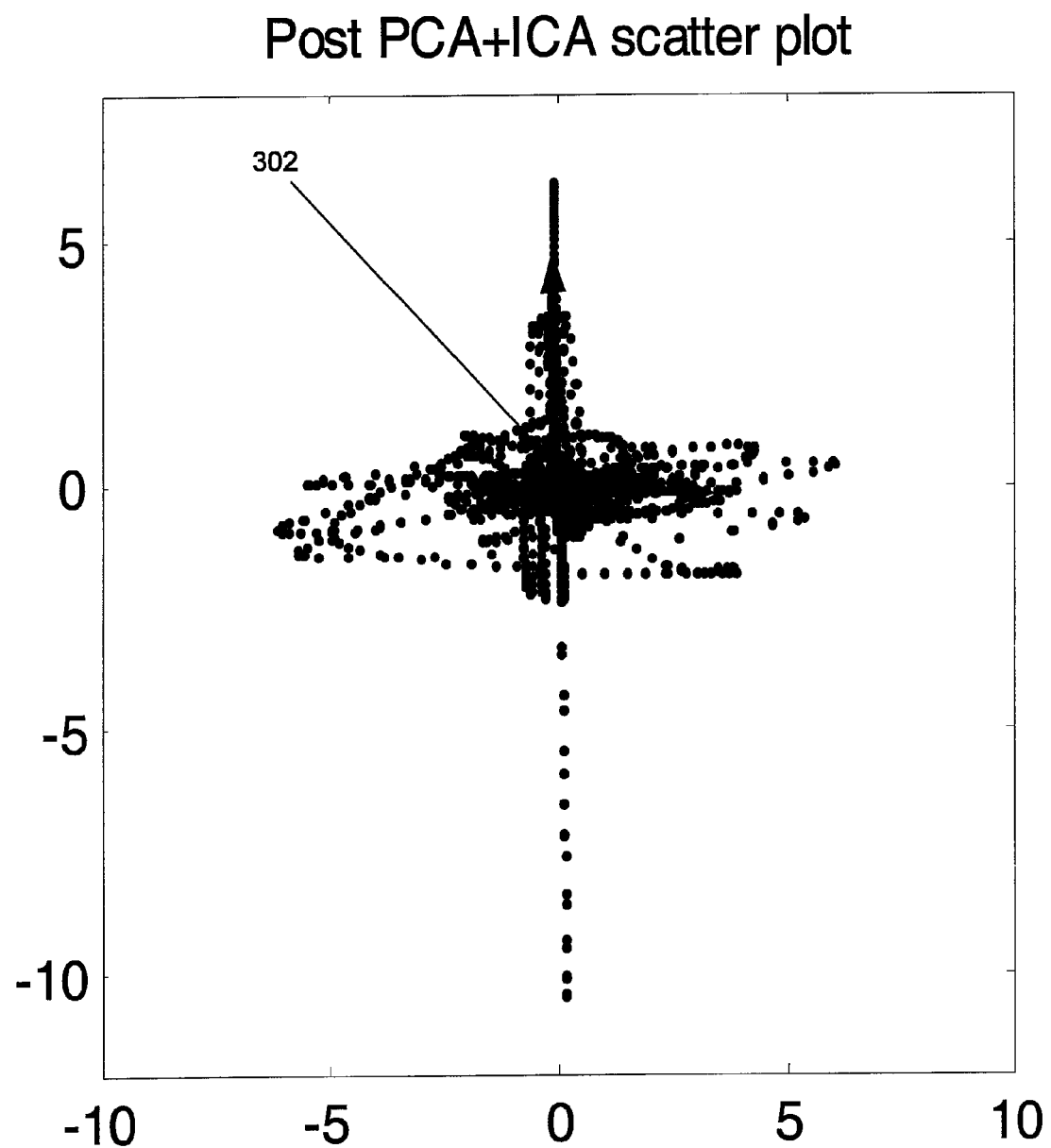
FIG. 3b shows a scatter plot of subcomponents of the same noisy signal of FIG. 3a after application of PCA and ICA, according to another example embodiment.

In various embodiments involving the use of an ICA technique to identify subcomponents associated with signal sources, an inverse of the mixing matrix $A_j$ is estimated [4,16] as a solution of an optimization problem that maximizes independence between the signal sources. For example, ICA techniques can use either higher-order statistics of signal components [17, 18] or information-theoretic criteria to maximize independence. Information theoretic criteria that can be applied include maximization of negentropy or its approximation [19], minimization of mutual information [19], maximum likelihood estimation [20, 21], maximum a posteriori probability [22], or expectation-maximization of Gaussian mixture models of sources [23]. These solutions can be approximated via efficient numerical methods, such as FastICA [24] and JADE [19] algorithms. The FIG. 3a provides a scatter plot image of subcomponents in the second domain prior to the application of PCA and ICA in the denoising process. FIG. 3b demonstrates an example result of denoising and subcomponent separation achieved by applying a combination of PCA and ICA techniques. Note that application of PCA and ICA has achieved a decorrelation of the subcomponents and alignment along the coordinate axis 302 of the scatter plot, indicating a large degree of independence has been achieved between the subcomponents (e.g., relative to alignment within coordinate axis 301 FIG. 3a). This high degree of independence between subcomponents that occurs as a result of the denoising process facilitates efficient removal of noise and signal source extraction.

In embodiments involving the use of πCA technique to identify signal sources, an inverse of the mixing matrix $A_j$ is estimated as a solution of an optimization problem that separates subcomponents based on their periodicity or quasi-periodicity [25, 26]. Instead of diagonalizing and inverting the covariance matrix as is done with PCA, the πCA technique jointly diagonalizes the covariance matrix and an autocorrelation matrix. The autocorrelation matrix is calculated as an average of autocorrelation matrices computed over time lags corresponding to period lengths.

In one embodiment, a quasi-periodic signal can be phase-wrapped by mapping the period length to a linear phase ϕ(t) ranging from −π to +π assigned to each sample. The autocorrelation matrix can then be calculated in the polar coordinates in which cardiac cycles are phase aligned. The technique involves extracting most pseudo-periodic subcomponents corresponding to a desired physiologic signal. The technique is efficient at identifying signal source and noise subcomponents but relies on accurate detection of cycles such as cardiac or respiratory cycles. It can be used in combination with spatially selective filtering (SSF), a technique that facilitates better cycle detection.

In another embodiment, referring to FIG. 2, signal sources are identified and separated in the second step, blocks 204 and 205 as discussed above using spatially selective filtering. Spatially selective filtering [27, 28, 29, 30] techniques detect signal-related features and pass them across the subcomponents while blocking features inherent to noise. The technique relies on the differences of noise and signal distributions between subcomponents. In one embodiment, spatially selective filtering is facilitated by a decomposition whereby signal energy is concentrated in a small number of large subcomponent coefficients while noise is spread out across many decomposition levels and is represented by small coefficients. Techniques similar to wavelet thresholding [31] can be used to remove this noise. This may result in a slight degradation of signal morphology.

In another embodiment, spatially selective filtering is used to exploit the fact that most noise subcomponents are confined to decomposition levels that represent high frequencies. In this embodiment the locations of signal features are identified by examining subcomponents corresponding to lower frequency or correlation between subcomponents. For example, QRS wave location can be identified as high amplitude peaks and valleys that occur simultaneously across multiple subcomponents associated with lower frequencies. The rest of the ECG waves (P, T, U) have lower frequency content.

Figure 20:
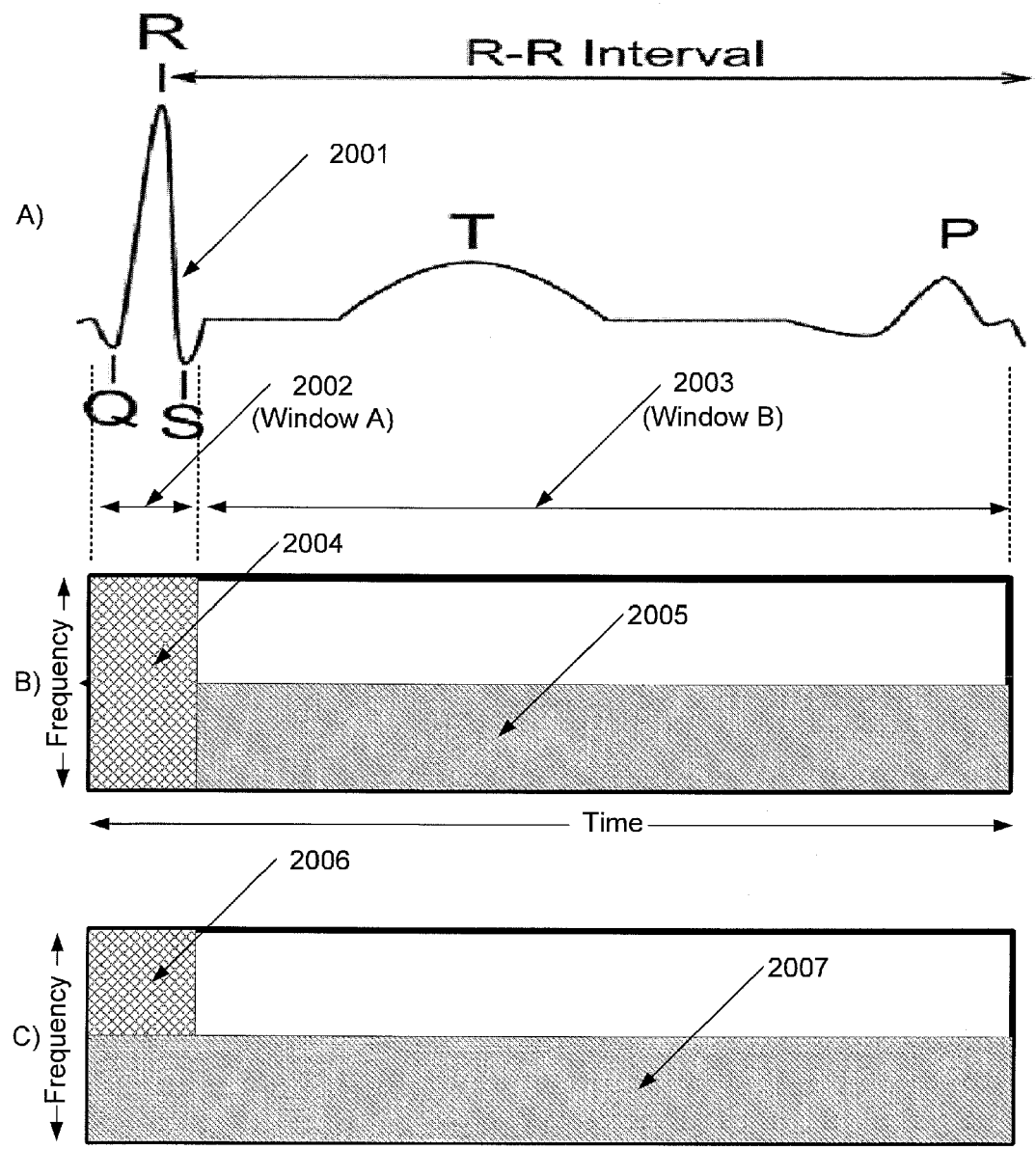
FIG. 20 illustrates an approach for spatially selective filtering, and partitioning of a cardiac cycle of an ECG signal, according to another example embodiment of the present invention.

Referring to FIG. 20, a cardiac cycle of an ECG is partitioned into time windows 2002 and 2003: 2002 containing the QRS complex and 2003 spanning the remainder of the cardiac cycle. The subcomponents associated with both low and high frequencies, represented by region 2004, are preserved within the time window 2002 containing the identified QRS complex. The low-frequency subcomponents associated with the desired signal, present in window 2003 and represented by region 2005, are preserved and subcomponents associated with high frequencies are removed. In another embodiment, subcomponents associated with low-frequencies, represented by region 2007, are preserved throughout the cardiac cycle and subcomponents associated with high frequencies are preserved in a time window represented by region 2006. In another embodiment, in signals with low amplitude subcomponents that are associated with high frequency such as PNA, high amplitude EMG noise can be detected as large peaks present in subcomponents corresponding to high frequency. The EMG noise can then be removed by zeroing subcomponents in the time window where the large peaks were detected. In another embodiment, the high amplitude noise or artifact is detected by identifying undesired peaks in subcomponents that correspond to frequencies that do not overlap the band of frequencies associated with the desired signal. For example, a blood pressure signal can be denoised using this approach.

In some embodiments the spatially selective filtering is combined with one or more of PCA, ICA, or πCA. For example, the subcomponents that were identified as noise at the PCA stage can be further filtered to remove only some segments that have spatial and temporal characteristics of noise. In another example, the subcomponents that were identified as signals at the PCA stage can be further filtered to remove additional time segments from subcomponents that have spatial and temporal characteristics of noise.

The choice of a technique for identification of subcomponents for denoising or signal source extraction depends upon signal and noise characteristics of the physiologic signal, spatial distribution of its subcomponents and the signal acquisition and processing environment. For example, it may be useful to process multi-channel signals with PCA and ICA techniques and their combinations with spatially selective filtering. When processing ECG signals obtained from an implanted single lead device spatially selective filtering or πCA may be applied, as in blocks 105 and 205 in FIGS. 1 and 2, respectively.

In some embodiments, step three as shown in blocks 106 and 206 of FIGS. 1 and 2, respectively, involves reconstructing the subcomponents remaining following denoising and signal source extraction, s(t)=(s₁(t), . . . , s_P(t)) in the first domain. This is accomplished by an inverse transform of extracted signal sources or denoised signal sources. If wavelet-based decomposition is employed, the reconstruction step can be formally described as iterative multiplication by an inverse of the operator matrix $W^j$ with each iteration step j corresponding to a reconstruction level.

Figure 4:
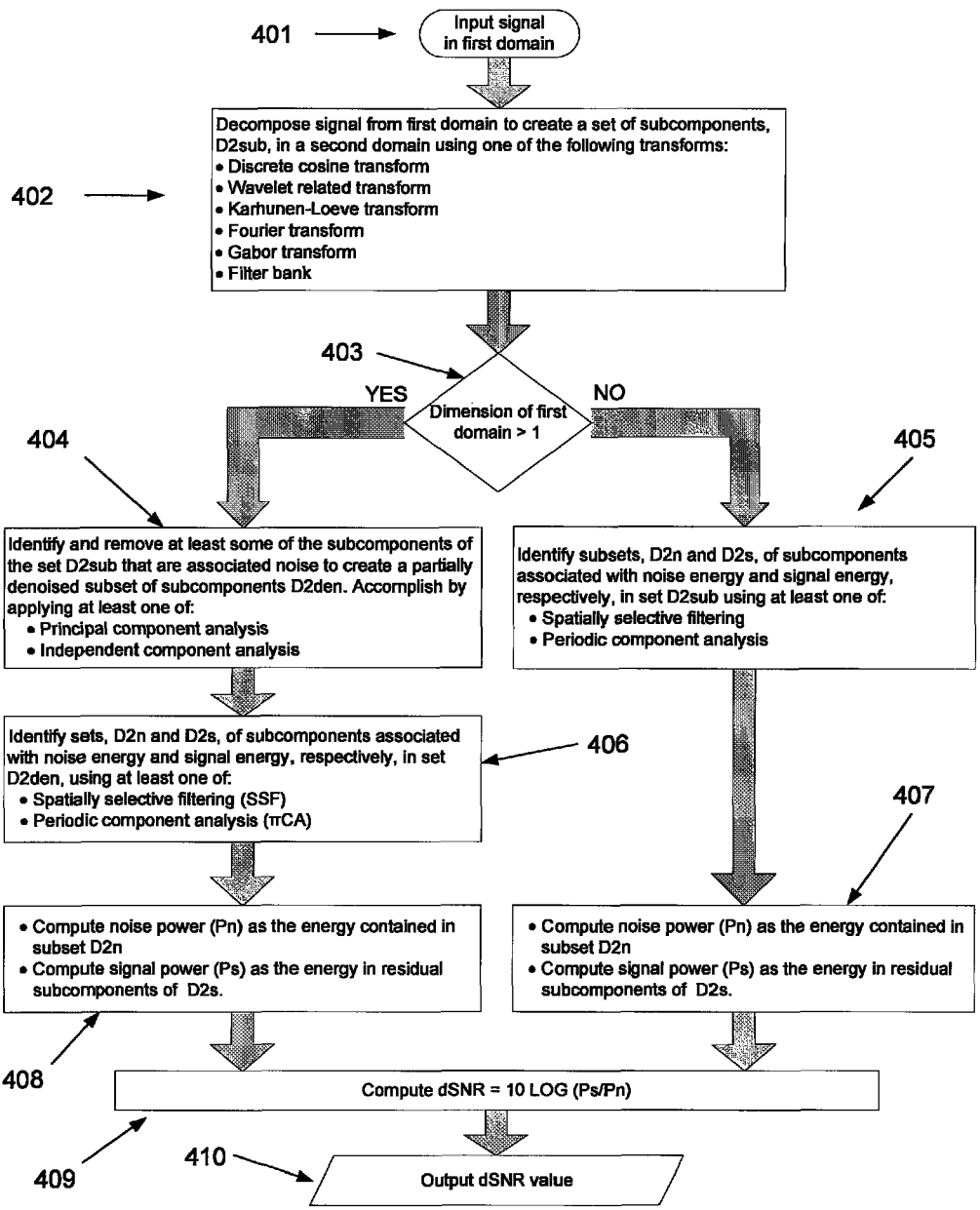
FIG. 4 illustrates a data flow diagram for computing a dynamic signal-to-noise ratio, according to an example embodiment of the present invention.

Referring to FIG. 4, other example embodiments involve computing a dynamic signal-to-noise ratio (dSNR) in a manner that can be updated on a sample-by-sample basis. dSNR can be used to assess the accuracy and reliability of information derived from the physiological signal and, in some embodiments, can be combined with other signal information such as ECG arrhythmic event information to compute a validity metric to assess the validity of information extracted from a signal. If dSNR for a cardiac cycle is low, for example, information derived from the ECG for that cardiac cycle may not be accurate.

A dynamic signal-to-noise ratio (dSNR) can be computed as the ratio of the energies in signal and noise subcomponents. In one embodiment, referring to FIG. 4, an input signal 401 in a first domain is decomposed in process 402 into subcomponents, referred to as set D2sub, in a second domain of higher dimension. At decision point 403, the signal processing flow proceeds according to the dimension of the first domain. If the dimension of the first domain equals 1, then subcomponents primarily associated with noise, referred to as set D2n, are identified in process 405 using SSF or πCA. Subcomponents of set D2n are combined to compute an estimate of noise energy and residual subcomponents, referred to as set D2s, are combined to compute an estimate of signal energy in process 407. The SNR is then computed in process 409 to create output dSNR value 410 according to formula:

$$SNR_{dB} = 10\log_{10}\left(\frac{P_{signal}}{P_{noise}}\right) = 20\log_{10}\left(\frac{A_{signal}}{A_{noise}}\right)$$

Where $P_{signal}$ and $P_{noise}$ are respective signal and noise energy and $A_{signal}$ and $A_{noise}$ are respective signal and noise amplitude.

If the dimension of the first domain is larger than one, a PCA or ICA technique can be used in process 404 for initial subcomponent denoising. The noise subcomponents extracted at this initial denoising step can be discarded and the residual noise and signal subcomponents can be identified using SSF or πCA in process 406. In process 408, the noise subcomponents identified at this stage, D2n, are used to calculate an estimate of noise energy and the residual subcomponents, D2s, are used to compute an estimate of signal energy. The SNR is then computed in process 409 (e.g., as described above).

In other embodiments, a signal-to-noise ratio is estimated using conventional approaches following denoising of the signal using an MDSP embodiment. In one embodiment, the noise is measured between signal waves by computing the peak amplitude and density of zero crossings or variability of signal in a segment between signal waves. In other embodiments, a signal-to-noise ratio is estimated by computing a spectral distribution of the denoised signal. For example, in an ECG signal, peaks in the spectral distribution are evaluated to determine the relative power in the spectrum that occurs within and outside of the normal range of the QRS complex, T-wave, and P-wave.

In one embodiment dSNR is updated for each cardiac cycle. Alternative implementations may update dSNR more or less often. For example, it may be useful in some embodiments to compute a value of dSNR for a window of two to ten cardiac cycles and use this value in calculation of the validity metric for all cardiac cycles within the window.

Figure 5:
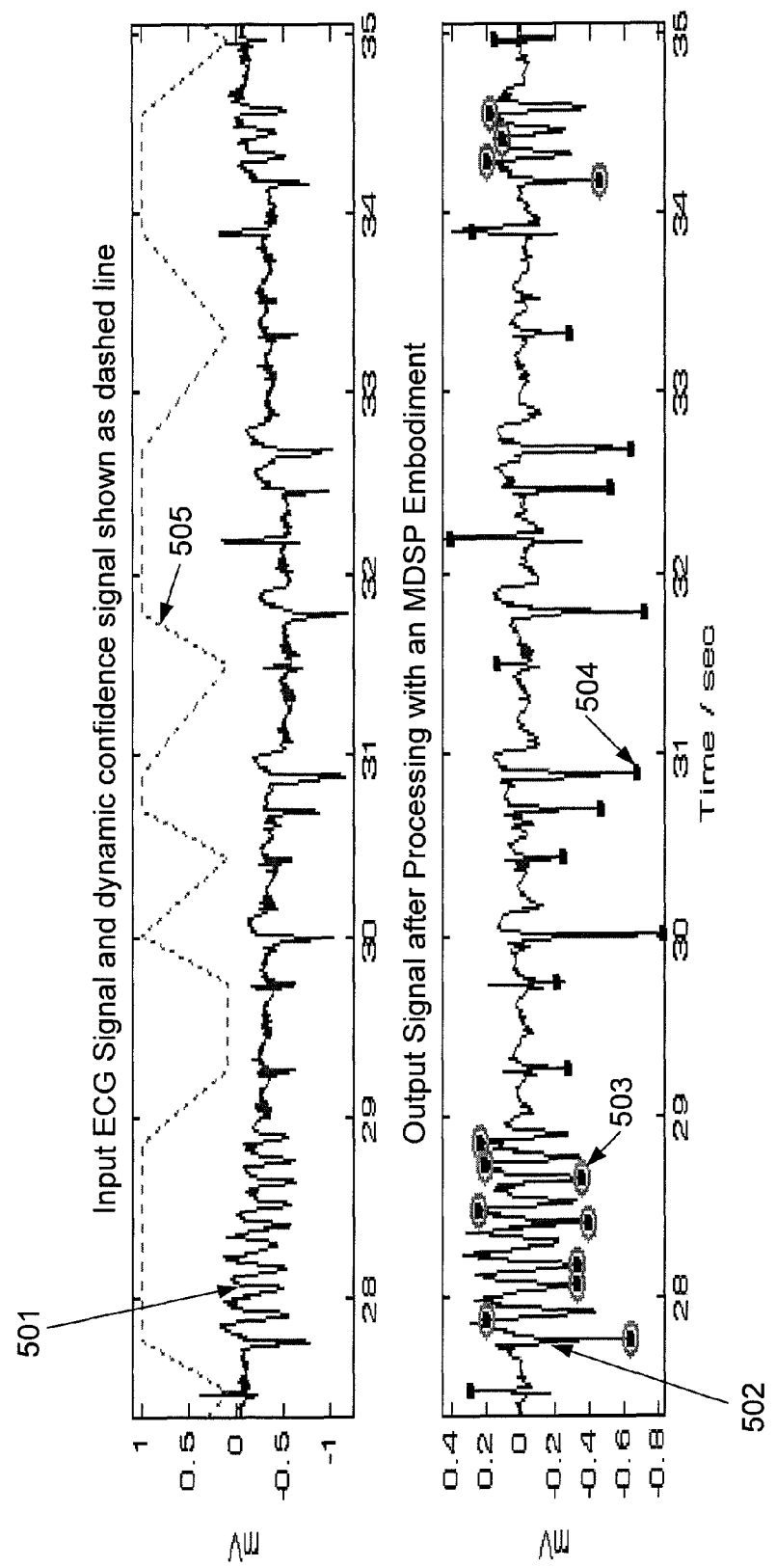
FIG. 5 shows an example of denoising performance and QRS detection in a rabbit ECG with non-sustained ventricular tachycardia and illustrates a dynamic signal-to-noise ratio updated for every cardiac cycle, according to an example embodiment of the present invention.

FIG. 5 provides an example of a dynamic confidence signal (dCS) derived from dSNR computed for a rabbit ECG signal 501, with dCS shown in the dashed line 505 in the top plot, and the bottom plot showing automatic marking of QRS complexes (squares as 504) and detected VT (circles as 503), in accordance with another example embodiment. The dynamic confidence signal 505 (dashed) is updated for each cardiac cycle. The dCS is updated every cardiac cycle and the value of dCS reflects changes in signal amplitude relative to the level of noise in the recording. Despite the low signal-to-noise ratio, all QRS complexes (as indicated by the squares 504 marking bottom ECG trace) and non-sustained episodes of ventricular tachycardia (marked by circles 503 marking bottom ECG trace) are detected.

In various embodiments, MDSP-based approaches as discussed herein are used to denoise and extract information from a physiologic signal acquired in a low SNR environment. For example, a collar or spring-loaded clip placed on the neck of an animal with embedded ECG electrodes can be used to collect ECG signals in animals non-invasively. While such an approach may result in a low SNR, denoising approaches such as discussed herein can be used to glean meaningful data from the ECG signals. Another embodiment is directed to placing a collar or spring-loaded clip on the neck of an animal, or a collar placed around the tail or limb, which can house light emitting diode transmitters and light receiving sensors to collect photoplesythmography signals. In one embodiment, the collar or clip includes two pairs of light transmitters and receivers placed at different locations on the neck of the animal in order to achieve redundancy and improved noise suppression. In another embodiment a cage floor having ECG sensors is used to collect ECG signals from the animal feet. These applications are exemplary of many applications characterized by low SNR, for which denoising approaches as discussed can be used to render the applications viable for analysis.

In the following examples, performance aspects are discussed as may be relevant to various embodiments illustrated and analyzed, many of which involve the analysis of ECG and PNA signals that can be challenging to carry out using other approaches. In many of the examples discussed here, the signal sources are contaminated with noise and the number of sources is larger than the number of observed signals. Although embodiments of the present invention can be used with a broad range of physiological signals, exemplary performance is illustrated with ECG and PNA signals that are problematic for traditional signal processing approaches because of contamination with in-band noise that could not be substantially reduced without distorting signal morphology. Such embodiments are applicable to the use of MDSP-based approaches as discussed herein, to achieve certain performance-related conditions or characteristics, which can be measured or relatively characterized in manners as discussed herein. Accordingly, various embodiments are directed to approaches to achieving such things as levels or degrees of noise reduction, signal quality, cardiac (or other signal) event detection accuracy and more, as facilitated using aspects of the invention as described herein.

Various MDSP-based embodiments are directed to denoising a physiological signal while preserving the morphology of a desired signal within the physiological signal (e.g., as recorded). Quality of signal reconstruction (QSR) is a metric commonly employed to assess the ability of a noise removal technique to preserve morphology of the desired signal in signals with moderate to high signal to noise ratio. QSR is defined as the mean squared error between the original signal $x_{cl}$ and denoised signal $x_{den}$ calculated sample-by-sample as a percentage of the original signal variance.

$$QSR = 100\% * \left(1 - \frac{\sum_i (x_{cl}^i - x_{den}^i)^2}{\sum_i (x_{cl}^i)^2}\right)$$

QSR of a denoised signal would be close to 100% if the original recording is contaminated with minimal noise and if distortion introduced into the desired signal by denoising was very small.

Figure 6:
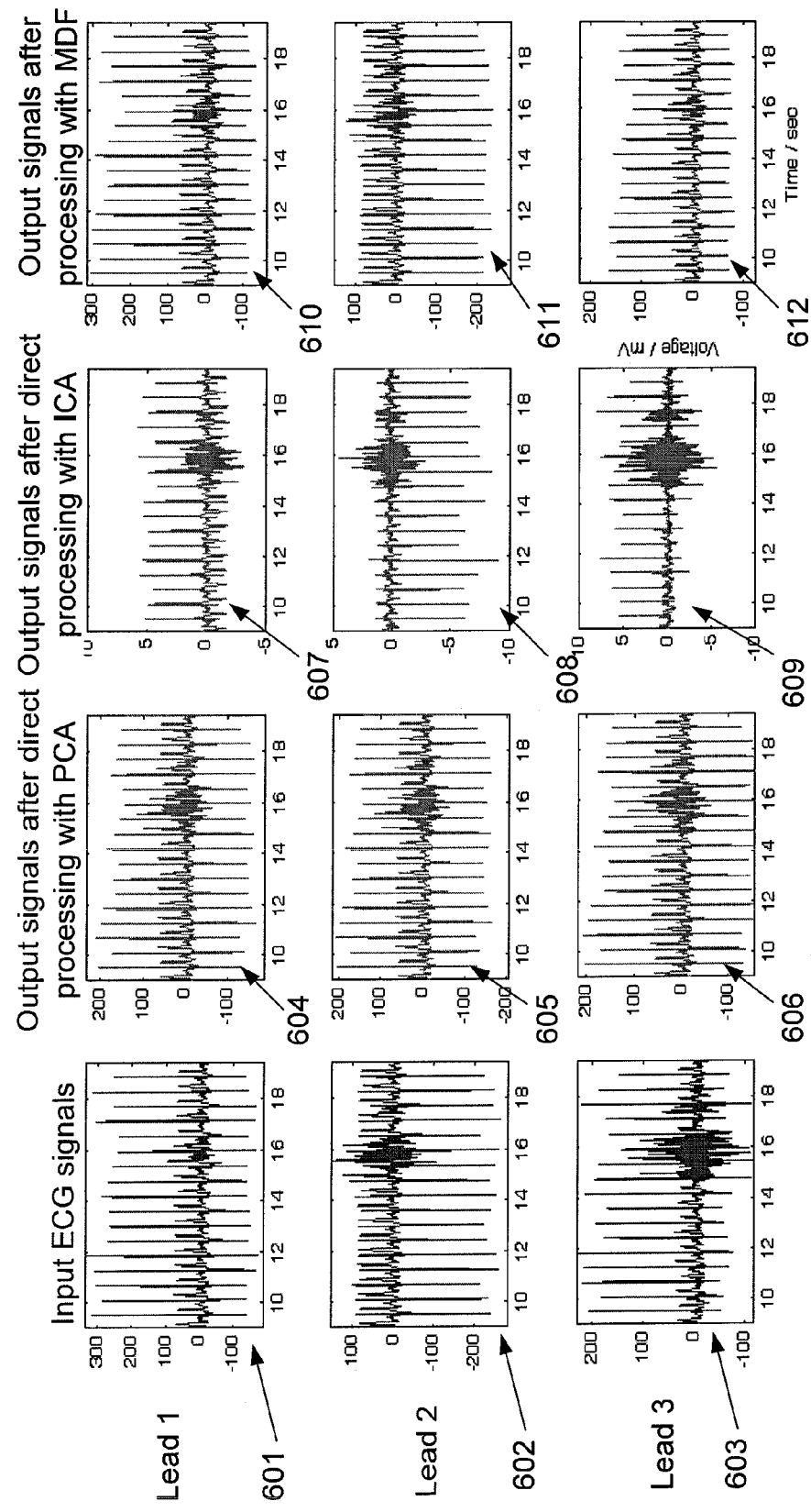
FIG. 6 shows an example of denoising performance on 3-lead ECG signals using PCA, ICA, and MDSP, according to another example embodiment of the present invention.

FIG. 6 shows plots characterizing an example MDF-based embodiment directed to removing noise from input 3-lead ECG signals 601, 602, and 603 from a PhysioNet [32] database. Results of ICA and PCA applied directly to the signal are also shown for comparison. The ECG recordings of FIG. 6 represent signals with portions that are relatively noise free (601) and portions that are noisy (602 and 603), demonstrating the removal of noise with an MDF-type approach as discussed herein while also preserving morphology. In such a short recording, the character of the denoising technique, whether MDF, ICA, or PCA, is relatively consistent throughout the duration. Evaluating QSR for the portion which is relatively noise free, therefore, provides an indication of a technique's ability to preserve morphology while a visual inspection of the noisy portion provides for a qualitative assessment of the ability of a particular technique to suppress noise. For the relatively noise free portion, the MDF-based approach shows QSR values of 98%, 99%, and 92% for the top 610, middle 611, and bottom 612 traces, respectively, indicating that distortion was negligible. The PCA approach shows QSR values of 83%, 68%, and 71%, for the top 604, middle 605, and bottom 606 traces, respectively, indicating significant distortion of signal content. The ICA approach shows QSR values of 2%, 1%, and 4%, for the top 607, middle 608, and bottom 609 traces, respectively, indicating very significant distortion of signal content. Accordingly, various MDSP-based embodiments are directed to processing signals to address challenges relating to such QSR values that may be insufficient, if processed otherwise.

Figure 7:
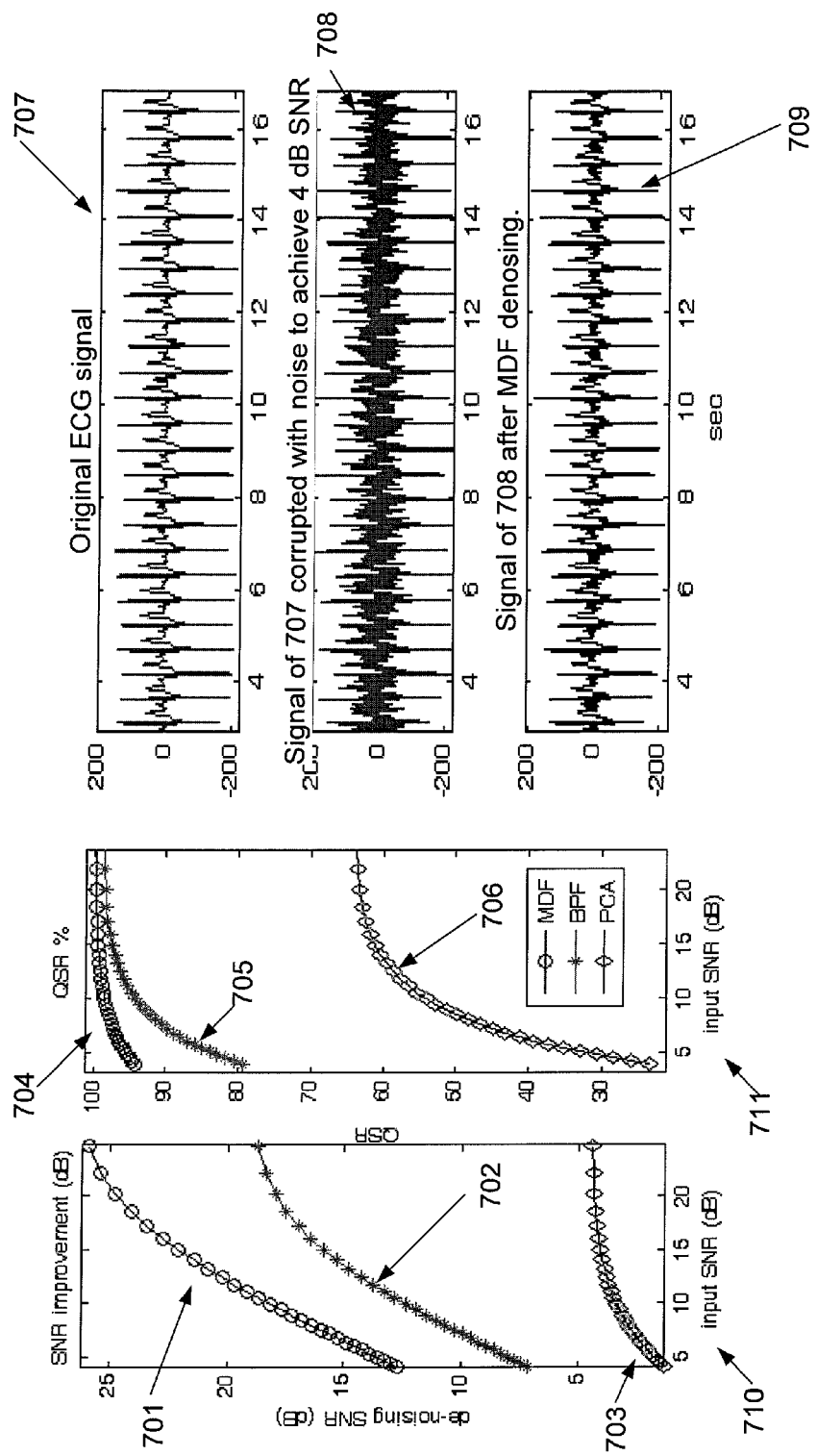
FIG. 7 shows results representing denoising performance of MDSP, PCA, and bandpass filtering, in connection with another example embodiment of the present invention.

FIG. 7 shows characteristic results of denoising using an MDF-type approach (in accordance with an example/experimental-type embodiment), Butterworth bandpass filtering (BPF) with a pass-band of 1 to 60 Hz, and PCA. A relatively noise-free ECG from the PhysioNet Long-Term ST database (record s30661) is corrupted with increasing levels of band-limited (0.05 to 70 Hz) white noise, and processed in accordance with an example embodiment. The denoising results are quantified measuring QSR and input and output signal SNR according to the formula:

$$SNR_{dB} = 20\log_{10}\left(\frac{\sigma_{signal}}{\sigma_{noise}}\right)$$

where $\sigma_{signal}$ and $\sigma_{noise}$ are respective clean-signal and noise standard deviations.

Referring to the plots 710 and 711 of FIG. 7, SNR and QSR versus input signal SNR achieved by MDF, PCA, and BPF are illustrated. Plot 710 illustrates the SNR improvement by comparing input SNR (on x-axis) to denoised signal SNR (on y-axis). Plot 711 illustrates the corresponding QSR for the same range of input SNR. For example, as illustrated in plot 710, an input signal with 4 dB SNR is denoised with an MDF-based approach, a 9 dB SNR improvement is achieved. Referring to the plot 711, 95% of the original clean signal content is preserved following MDF denoising of an input signal with 4 dB SNR. With increasing input SNR, QSR performance for the MDF-based embodiment quickly approaches 100% with an approximately linear denoising characteristic as measured by SNR on a logarithmic scale. Similar processing with a two-lead ECG generates similar results observed for an MDF-based embodiment. As shown in the FIG. 7 the PCA and BPF results can be improved upon using various embodiments as discussed herein.

Referring to the ECG tracings 707, 708, and 709 of FIG. 7, these three tracings illustrate an input noise-free signal 707; signal 708 corrupted with band-limited white noise to reduce SNR to 4 dB, and signal 709 denoised with an MDF-based approach. Adding band-limited white noise to achieve a 4 dB SNR renders the T and P waves indiscernible, as indicated in the middle tracing, while application of MDF restores the P and T waves.

Figure 8:
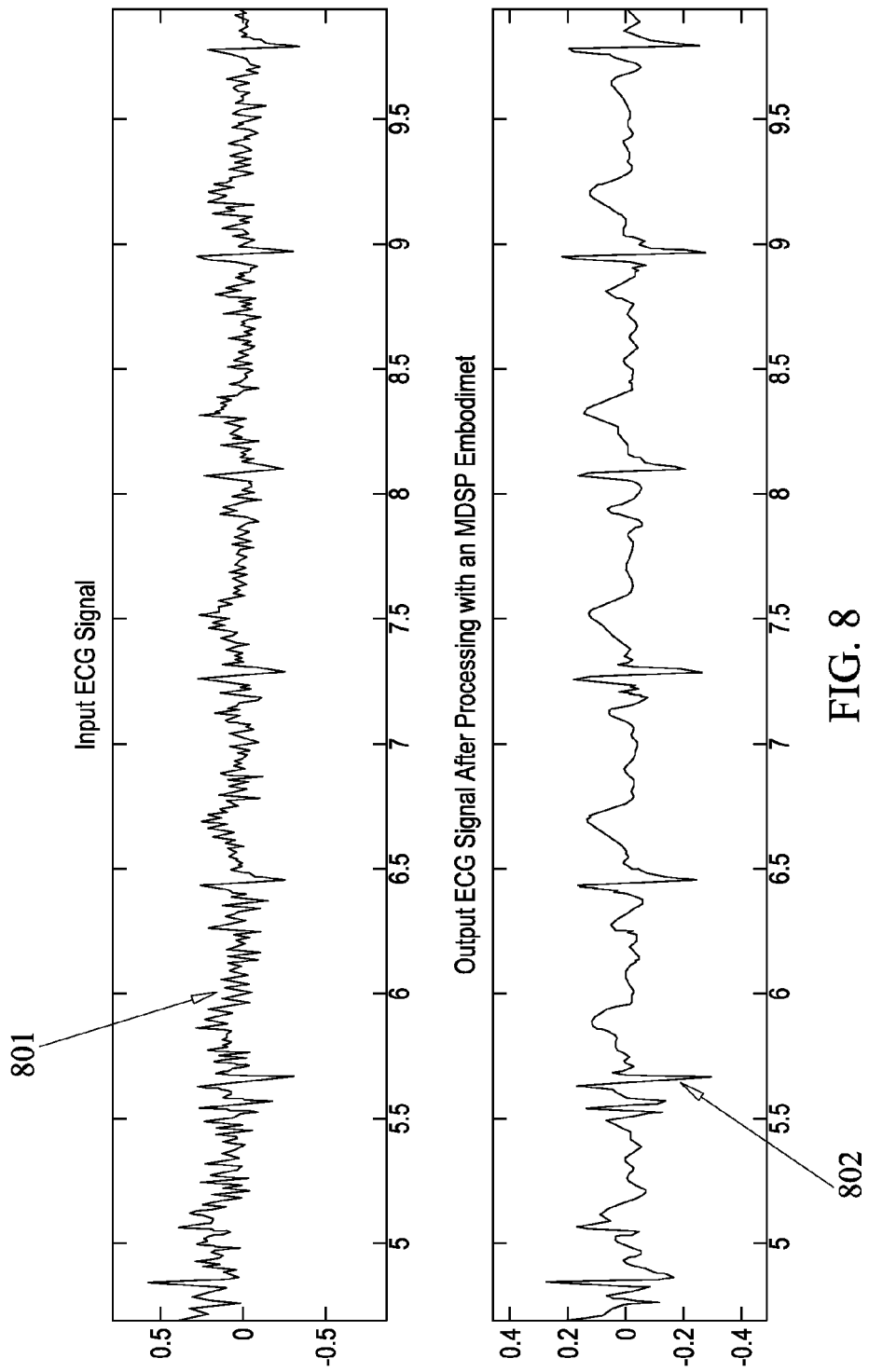
FIG. 8 shows an example of denoising performance on a single channel noisy ECG signal, in connection with an example embodiment of the present invention.

FIG. 8 shows another example embodiment, involving the use of MDF to suppress noise while preserving morphology for a single-channel ECG. Plot 801 is an input ECG recording corrupted with noise, and plot 802 shows the result of applying MDF filtering. The noise present in the input signal has similar characteristics (frequency content and amplitude) as QRS complexes which would result in QRS detection errors without denoising. The application of MDF is used to avoid potential QRS detection errors, and can remove most of the noise while preserving morphology of QRS, P, and T waves, allowing for high accuracy detection of all ECG features, including QRS complex, P, and T-waves.

The embodiments shown in FIGS. 6, 7, and 8 characterize an example use of MDF to suppress in-band noise while substantially preserving signal morphology, in accordance with various embodiments. This combination of attributes is useful for a multitude of applications, including clinical diagnosis and research involving the measurement and analysis of physiological signals. Waveform morphology is preserved for a variety of applications, such as for detecting abnormalities in cardiac function from an ECG, evaluating respiratory function from a respiratory signal, evaluating a signal from a photoplethysmography sensor for measuring oxygen saturation, evaluating sleep stages from an EEG, and other applications. For example, preserved QRS morphology is used in diagnosing bundle brunch block or ventricular hypertrophy, T-wave morphology is used in measuring repolarization abnormalities in clinical care and drug toxicity studies, and ST segment changes are used when diagnosing ischemia, electrolyte imbalance, and Brugada syndrome. In another example, the ability to preserve P wave and QRS complex morphology facilitates the analysis of time correspondence of P wave and QRS complex to diagnose AV block.

In another embodiment, an MDSP-based approach is used for denoising and signal source extraction for monitoring a fetal ECG. In this embodiment, an ECG is recorded by placing sensing leads on the surface of the skin of the mother, typically in the lower abdomen. In one embodiment, individual sources that make up a fetal ECG are separated from the remaining subcomponents in the second domain by applying ICA signal source extraction techniques in step 2 of the MDSP embodiment. In another embodiment the fetal ECG is extracted from the other subcomponents by spatially selective filtering, periodic component analysis, or their combination (e.g., in step 2 as shown in FIGS. 1 and 2 above). In this embodiment, the undesired sources, such as maternal ECG, are treated as noise and removed, leaving the denoised fetal ECG.

In another embodiment, an MDSP-based technique is used for measuring a degree of synchronization of uterine contractions of a pregnant female for predicting and detecting labor. In this embodiment, an electrohysterogram (EHG) is collected from the female abdomen. In one embodiment, an MDF-based approach as discussed herein is used to remove ECG artifacts from the EHG signal. In one embodiment, the degree of synchronization of contractions in denoised EHG signal is measured by amplitude correlation via linear or nonlinear regression and the frequency relationship measured as coherence, or the amplitude and phase synchronization in the time-frequency domain. In another embodiment, a cross wavelet coherence function is used to measure amplitude correlation between two contraction bursts [33, 34]. In another embodiment, an envelope of a multi-channel EHG signal is calculated using a Hilbert transform or low-pass filtering of a rectified EHG signal to measure amplitude of a contraction wave and its spatial synchronization.

In other embodiments, a MDSP approach as discussed herein is used for detecting atrial arrhythmias in an ECG. In these embodiments, atrial activity can be extracted by applying ICA, SSF, PCA, πCA, or their combination, as part of step 2 (process 204 and 205) as shown in FIG. 2. In this embodiment, step 2 can involve removing noise as well as the subcomponents associated with ventricular activity or segments of the subcomponents as identified by SSF.

Figure 9:
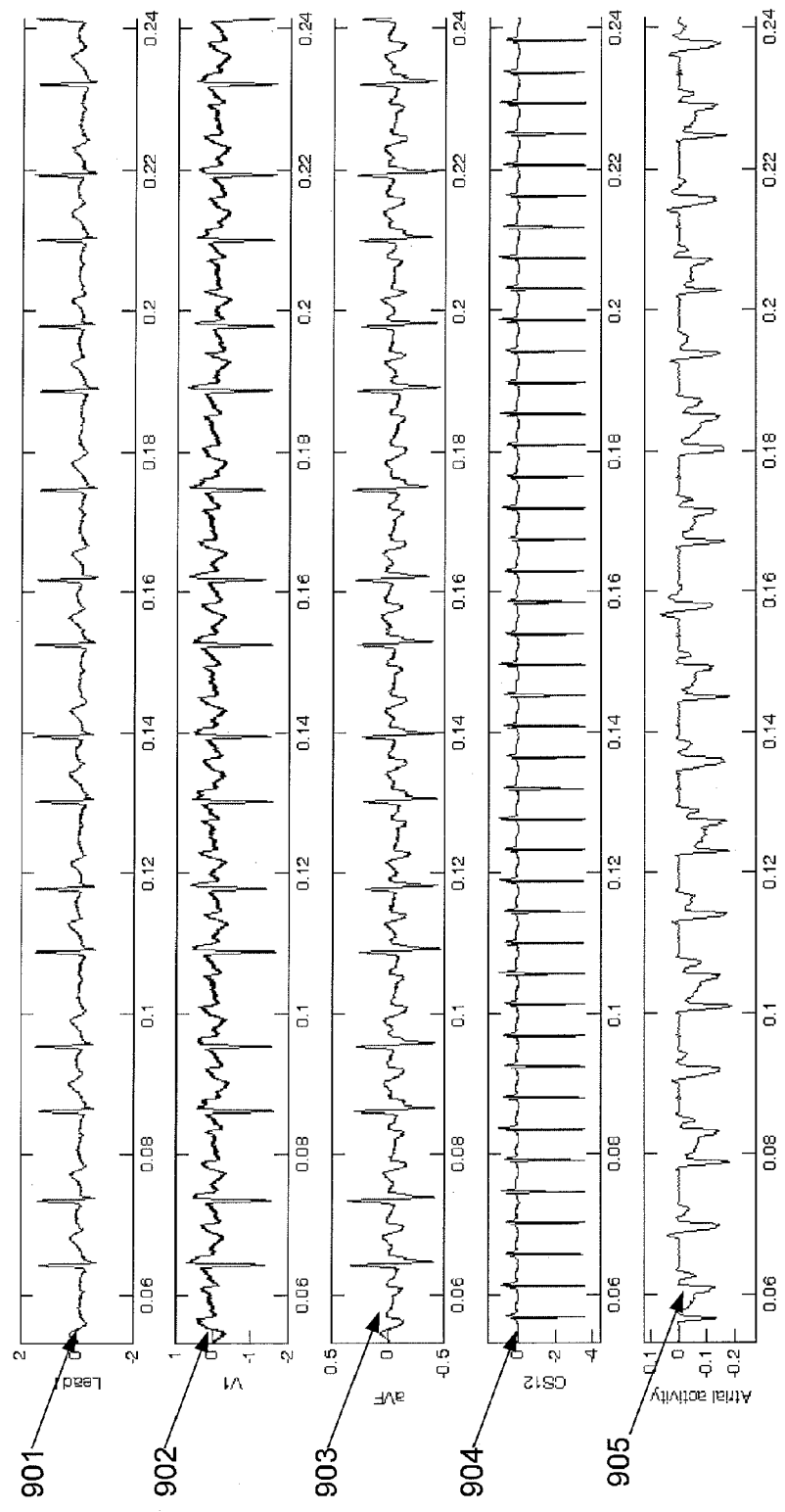
FIG. 9 shows an example of atrial activity extraction from a surface ECG signal containing atrial flutter, in connection with another example embodiment of the present invention.

In FIG. 9, the results of atrial activity extraction are illustrated on an atrial flutter recording from the PhysioNet database [32]. Plots 901, 902, and 903 show ECG recorded from surface leads. Plot 904 is a recording from an intracardiac catheter located near an atrial free wall. The intracardiac recording is shown as an exemplary benchmark of atrial activity. Plot 905 shows the atrial activity separated from the surface ECG recordings using an MDSP-based embodiment. Note that the locations of P-waves on the plot 905 of extracted atrial activity matches locations of atrial depolarizations recorded from intracardiac lead shown in 904. The gaps in atrial activity coincide with ventricular depolarizations (i.e., QRS complexes) and repolarizations (T-waves). Analysis of the separated atrial activity can significantly improve the accuracy of atrial flutter detection.

Figure 10:
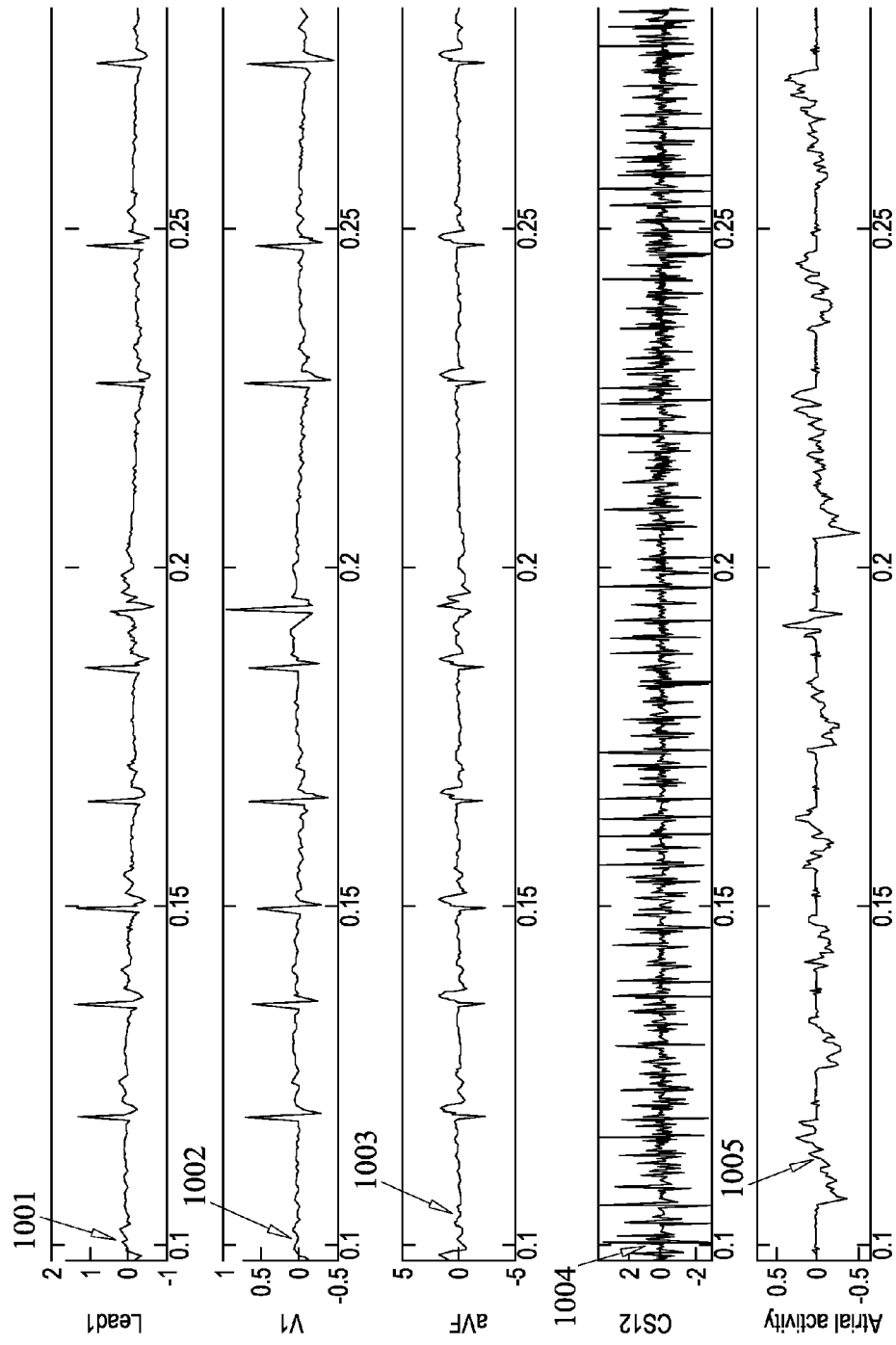
FIG. 10 shows an example of atrial activity extraction from a surface ECG signal containing atrial fibrillation, in connection with another example embodiment of the present invention.

In FIG. 10, the results of atrial activity extraction are illustrated on an atrial fibrillation recording from the PhysioNet database [32]. During atrial fibrillation the P-waves often degenerate into more fractionated and variable f-waves which are barely visible in surface recording traces 1001, 1002, and 1003 shown in FIG. 10. Despite that, the atrial activity signal 1005 extracted using an MDSP embodiment clearly shows the f-waves that coincide with the atrial depolarization trace 1004 recorded using an intracardiac lead. The only gaps are when atrial activity coincides with ventricular depolarizations (i.e., QRS complexes) and repolarizations (T-waves).

FIGS. 9 and 10 demonstrate that various MDSP-based embodiments are capable of extracting atrial activity from ECG recordings. There are a number of ways that extracted atrial activity can be used to improve the accuracy of atrial flutter and fibrillation detection and discrimination. For example, spectral analysis of the extracted atrial activity signal can be used to quantify P-wave regularity and frequency and discriminate between atrial fibrillation and flutter. In one embodiment, atrial rate can be estimated by spectral analysis. In another embodiment, extracted subcomponents corresponding to atrial activity can be analyzed in the second domain to estimate the atrial rate. In another embodiment, a P-wave similarity measure is used to detect and discriminate between atrial fibrillation and flutter. In another embodiment, zero crossings can be used to estimate atrial rate in the segments where atrial activity is present. The analysis of atrial activity can be combined with analysis of cardiac cycle variability and regularity as well as PR interval variability to further improve the accuracy of atrial fibrillation and flutter detection.

In other embodiments an MDSP-based approach is used for separating ventricular depolarization and repolarization activity. This may be useful for assessing repolarization activity for the risk stratification of sudden cardiac death. Once repolarization activity is extracted, it can be used to assess T-wave alternans and morphology, ST elevation in ischemia, and other cardiac abnormalities that can be useful for assessing cardiovascular risk.

Figure 11:
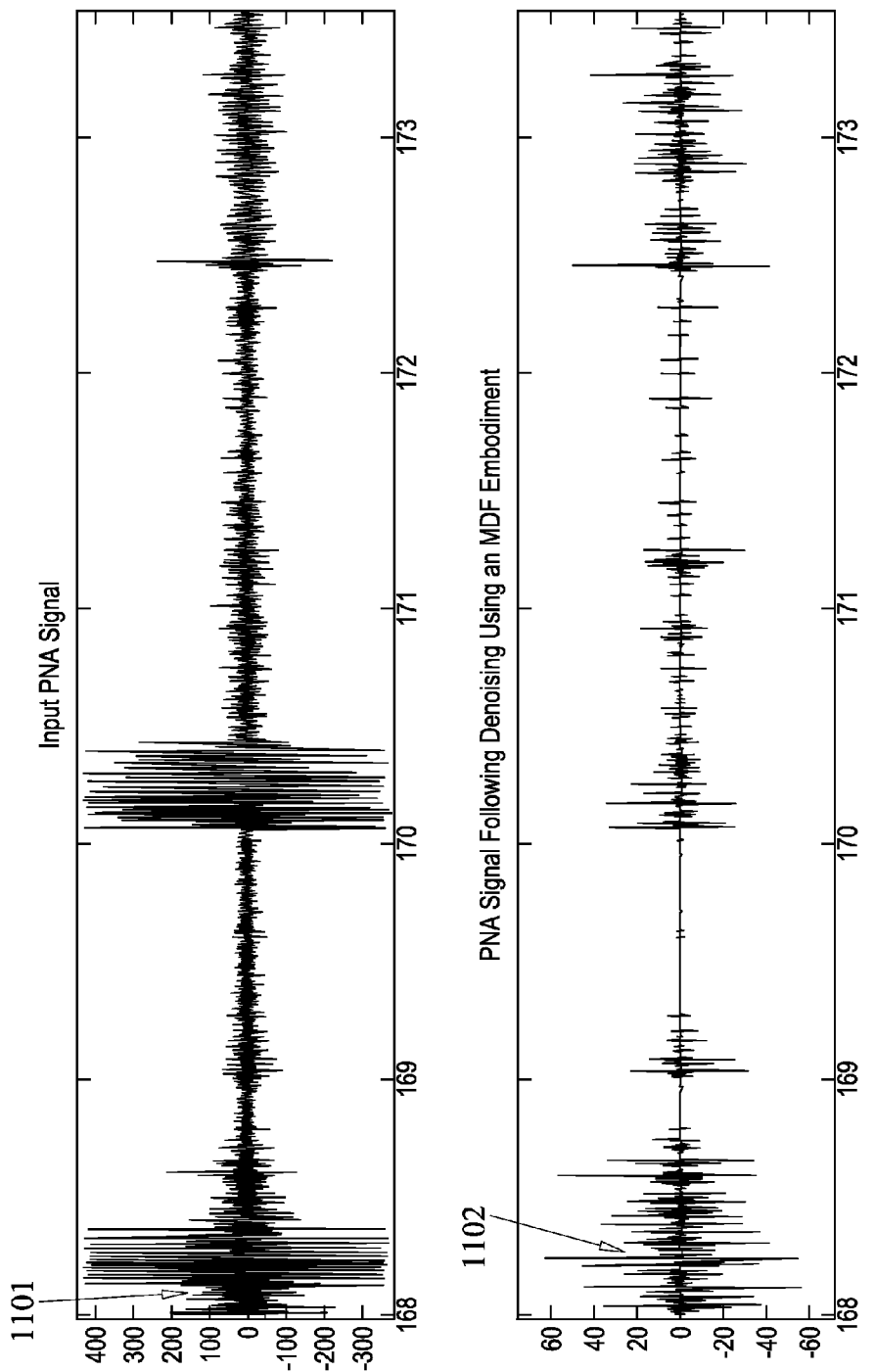
FIG. 11 shows an example of denoising performance on single channel peripheral nerve activity (PNA) recording corrupted with noise, in connection with another example embodiment of the present invention.

Another embodiment is directed to using MDF for removing high amplitude noise from PNA signals. In particular, this is useful when removing high amplitude noise from PNA recordings such as those from the vagal nerve, sympathetic nerves, or motor nerves. In this embodiment, the high amplitude noise or artifact is detected by identifying undesired peaks in subcomponents that do not overlap the band of frequencies associated with desired signal. In FIG. 11 exemplary performance of an MDF embodiment is illustrated on a single channel PNA input signal 1101 with high amplitude EMG noise. Plot 1101 is a PNA recording from a rat renal nerve while plot 1102 is the denoised signal following application of MDF. The MDF embodiment extracts the signal source from a very low SNR acquired signal while preserving PNA information. It removes nearly all noise and artifacts from the recording including myoelectric artifacts (EMG), electrical, and other noises while preserving information regarding the underlying PNA. An MDF embodiment could be used to extend the life of preparations where PNA is recorded by improving the ability to extract accurate information from PNA signals with low SNR. In PNA recording preparations for research in animal models, it is also common to dose the subject with a drug that shuts down PNA so that baseline noise can be measured and subsequently subtracted from the neural signal. This procedure can be dangerous for the subject and is labor intensive and cumbersome for the researcher. The MDF embodiment removes background noise automatically and eliminates the need for such an intervention.

In connection with another example, embodiment, PNA is quantified from recordings such as discussed above, via the computation of integrated sympathetic nerve activity. In one embodiment for computing a PNA envelope, an orthogonal component of the denoised PNA signal is computed using a transform such as a Hilbert transform, or similar transform. An envelope is computed as the square root of the sum of the squared denoised PNA signal and its orthogonal denoised component. This provides an accurate representation of neural activity without the phase delays inherent in conventional approaches. The neural activity represented by the signal envelope has a much lower frequency content compared to the raw PNA signal and thus substantially reduces the bandwidth and sampling rate requirement of a system for measuring PNA activity.

Monitoring devices that transmit raw PNA signals as may be used in accordance with this or other embodiments, such as that available from Telemetry Research, Auckland, NZ, employs a sampling rate of about 8,000 Hz. By employing this embodiment to calculate an accurate PNA envelope, the sampling rate can be reduced to 100 Hz or less, resulting in a reduction of transmitted bandwidth of a factor of 80 and a reduction in current drain of a wireless transmitter used to transmit data from an ambulatory subject.

In another embodiment, an MDSP-based approach is used for removing noise and extracting signal sources from signals acquired as a result of programmed periodic stimulation, such as auditory brainstem response and in peripheral nerve stimulation therapies where evoked response is analyzed to titrate therapy or peripheral nerve recruitment. These signals are often characterized by low SNR and a limited number of observed channels. These signals can be segmented in the time domain based upon knowledge of timing of stimulation. Segmentation in the time domain allows for the creation of the equivalent of multiple channels from the observed signal, hence increasing the number of dimensions in the first domain. Following decomposition into the second domain of larger dimension than the first domain, one or more MDSP-based embodiments previously described can be applied for denoising and signal source extraction. For auditory brainstem response, an MDSP-based embodiment can be used to improve the accuracy of intracranial pressure estimation, such as with a system similar to that described in US Patent Application Publication 20080200832, and U.S. Pat. No. 6,589,189, which are fully incorporated herein by reference.

In the case of a peripheral nerve stimulation therapy, evoked responses can be analyzed to titrate therapy targeted at specific nerve fibers or monitor neuropathy progression. For example, in vagal nerve stimulation applied for cardiovascular therapy, the stimulation protocols are optimized to selectively recruit efferent smaller fibers that control heart function and block stimulation of efferent larger fibers and afferent fibers that could invoke pain or coughing reflex. Such approaches may be implemented in accordance with that described in U.S. Patent Application Publication 20080065158, which is incorporated herein by reference. A device employed for neural stimulation may incorporate a feedback control of stimulation by observing parameters of an evoked response. In this type of neural stimulation device, an MDSP-based embodiment could be applied to assess evoked response resulting from nerve stimulation targeted at a specific nerve fiber type. In some implementations, an MDF-based embodiment is used to achieve an accurate assessment of the response of particular nerve fibers to changes in programmed stimulation parameters such as timing, frequency, pulse width, pulse repetition, duty cycle and amplitude of stimulation in order to appropriately affect therapy.

In another embodiment, an MDSP-based embodiment is used to monitor neuropathy progression by measuring changes in nerve conduction velocity of small diameter axons. The changes in these axons can serve as an earlier marker of neuropathy development. An MDSP-based embodiment that involves segmenting the evoked response signal and denoising as described above is used to remove background noise and for measurement of evoked response amplitude and time. In many embodiments, this approach is used to facilitate the detection of changes in axons that can otherwise be challenging to detect due to low amplitude and phase cancellation of evoked response potentials.

Figure 12:
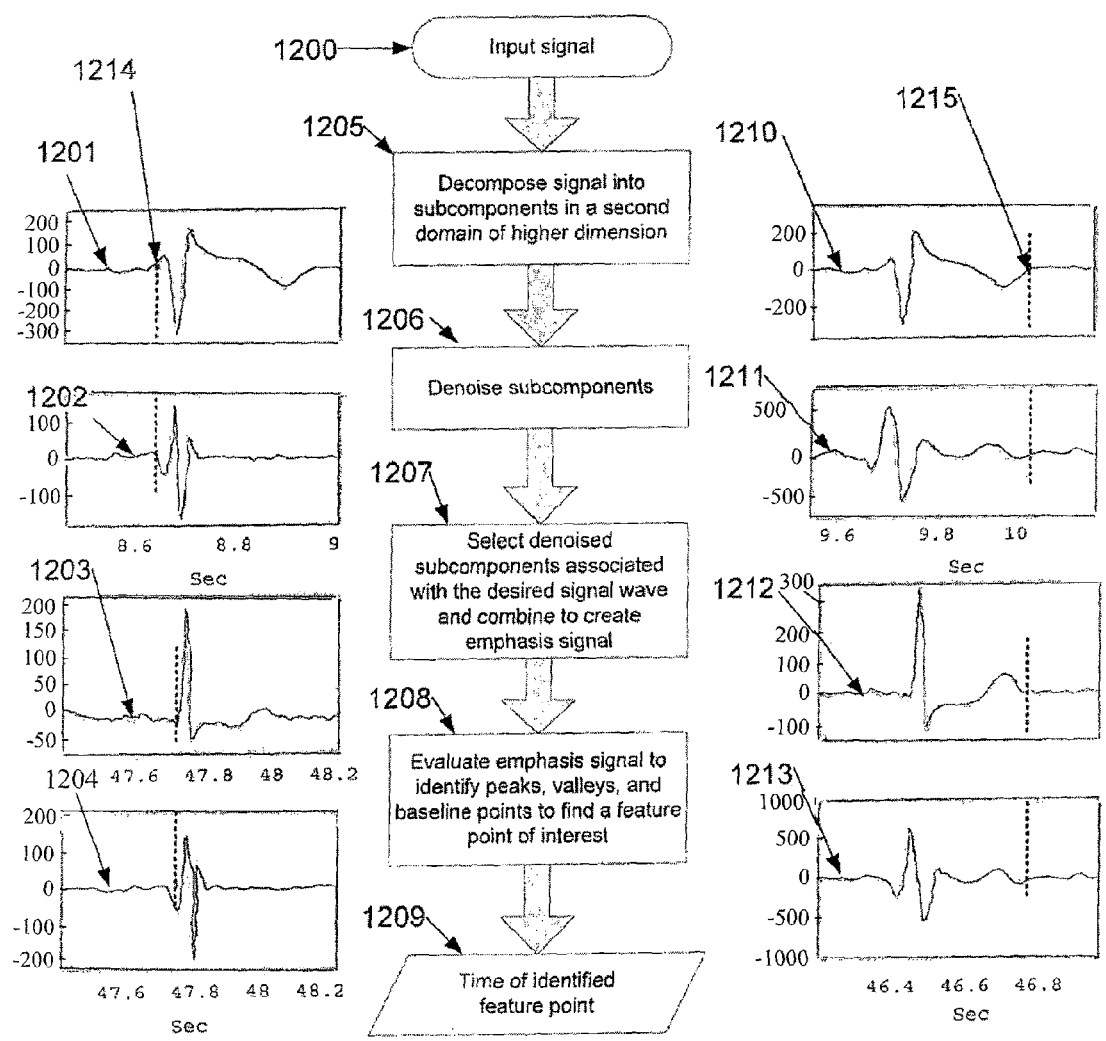
FIG. 12 shows a data flow diagram for computing an emphasis signal and finding a feature point in a signal waveform, and example signal waveforms and corresponding emphasis signals and feature point markers, according to another example embodiment of the present invention.

In another embodiment, MDSP is used for detecting feature points of a physiological signal such as a QRS onset, P-wave onset, or T-wave offset in an ECG signal or systole and diastole in an arterial blood pressure signal. Referring to FIG. 12, this feature point detection embodiment uses one or more selected denoised signal subcomponents to compute an emphasis signal that emphasizes a signal wave or feature point of interest, computed as a linear or non-linear combination of selected subcomponents that are associated with the signal wave of interest. In another embodiment, the emphasis signal is computed by performing the inverse of the transform used for decomposing the physiological signal on the selected subcomponents. In some embodiments it may be useful to differentiate the signal following the inverse transform.

Referring to FIG. 12, subcomponents used to compute the emphasis signal are generated as a result of the decomposition process 1205 of input signal 1200 using an MDSP embodiment, as described herein. The subcomponents that contain the majority of the energy of the signal waves are selected for the emphasis signal and are denoised in process 1206 using an MDSP embodiment. The emphasis signal computed in process 1207 may include frequency subbands matching the spectral energy of particular signal waves of interest or a subset of basis functions tuned to the signal wave or feature point of interest and its variations across a range of normal, perturbed, and pathological conditions. In another embodiment wavelet related subcomponents can be used to compute the emphasis signal in process 1207. The specific subcomponents used depend upon the decomposition technique used, sampling rate, and the species from which the physiologic signal was recorded. Example emphasis signals of an ECG are shown in 1202, 1204, 1211, and 1213 of FIG. 12, along with corresponding ECG waveforms 1201, 1203, 1210, and 1212. The vertical dashed lines in FIG. 12 show the point of feature point detection in each ECG waveform and corresponding emphasis signal.

The transition points of the emphasis signal are evaluated in process 1208 to detect feature points, shown by example in 1214 and 1215, of the physiologic signal to create output 1209 representing the time of the feature point. In one embodiment, the pattern of significant peaks, valleys, and zero crossings within the emphasis signal are used to detect feature points. In another embodiment, the feature points are detected by applying a threshold to the emphasis signal. In yet another embodiment, the feature points are detected by applying pattern or template matching.

The following illustrative example demonstrates exemplary performance of an embodiment involving the detection QRS complexes in an ECG. For QRS detection, an MDSP-based approach is used to compute an emphasis signal from a combination of denoised subcomponents that are algorithmically selected to include, for example, complexes that are wide, narrow, premature, fractionated, biphasic, monophasic, fibrillatory, tachycardic, or complexes that have been distorted as a result of a pharmacological agent.

Figure 13:
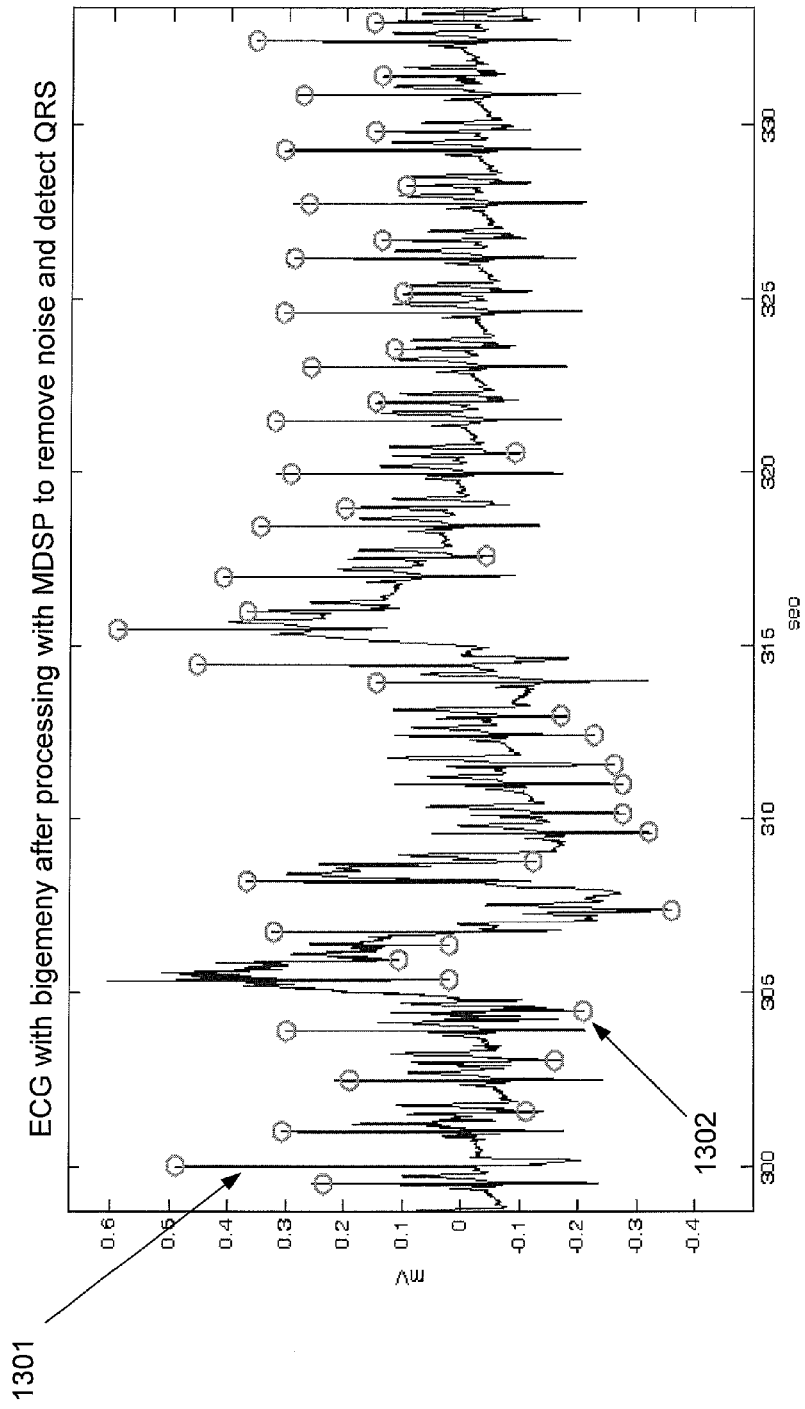
FIG. 13 shows an example of QRS detection performance for a challenging ECG recording, according to another example embodiment of the present invention.

FIG. 13 provides an illustration of an ECG signal 1301 that is processed in accordance with such an approach, to address problems that may relate to the presence of bigemeny, tall T-waves, and low QRS amplitude, in addition to rapid changes in QRS amplitude. An emphasis signal computed as described in this MDSP embodiment facilitates the detection of all QRS complexes, as shown by the circles as in 1302 of FIG. 13, with no false detection on T-waves. When tested on the MIT BIH Arrhythmia database [35], a QRS detection accuracy of 99.8% sensitivity and 99.8% positive predictive value can be achieved on single lead ECGs. Feature detection can be enhanced by using and analyzing multiple lead recordings, using an MDSP-based approach to leverage redundancies between the leads in a manner that is more efficient at removing noise.

Figure 14:
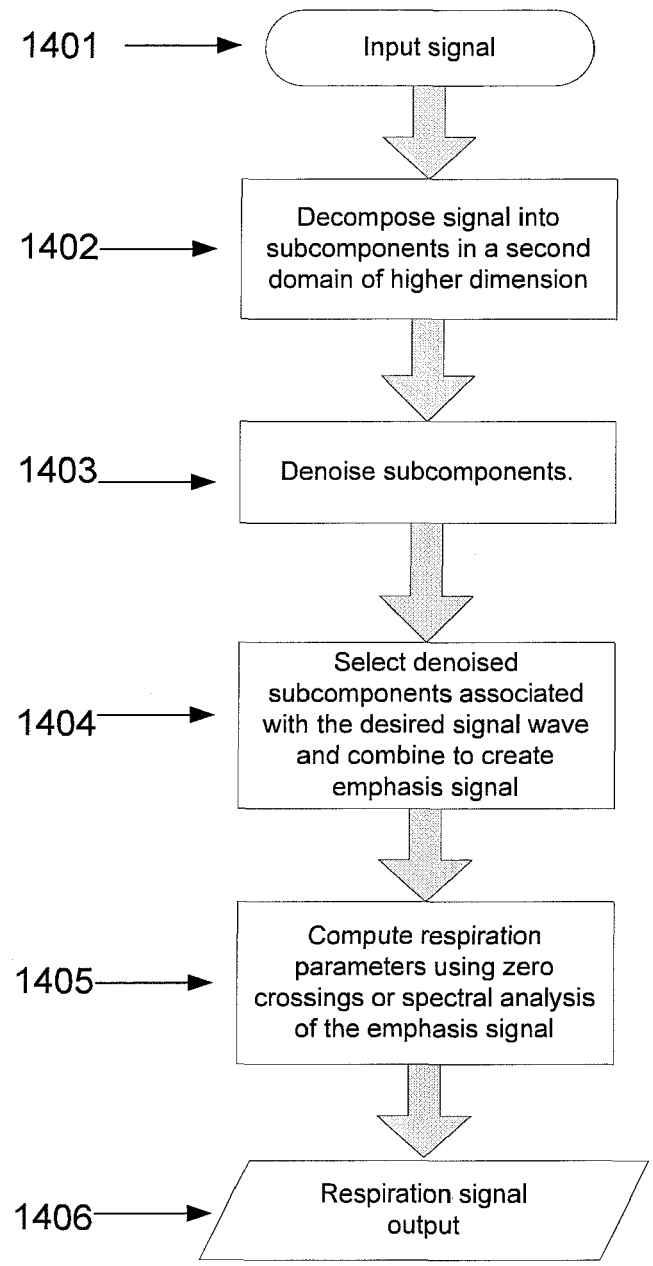
FIG. 14 shows a data flow diagram for computing an emphasis signal corresponding to a respiration pattern, according to an example embodiment of the present invention.

In another example embodiment, an MDSP approach is used for extracting a respiration signal from an ECG, blood flow, photoplethysmography, thoracic impedance, or an arterial blood pressure signal. FIG. 14 shows one such implementation, in which a respiration signal is extracted using one or more selected denoised signal subcomponents to compute an emphasis signal that is associated with a respiratory pattern. In some embodiments, the subcomponents are filtered with a low-pass filter to extract the low-frequency respiration signal.

In other embodiments, the emphasis signal is combined with a heart rate signal to improve the accuracy of computed respiratory parameters. For example, canines have pronounced respiratory sinus arrhythmia which is characterized by heart rate changes that correlate to respiration; these characteristics can be used in connection with these embodiments, for extracting, processing or otherwise using canine respiration signals.

Referring again to FIG. 14, subcomponents resulting from decomposition in process 1402 of input signal 1401 are used to compute an emphasis signal, using an MDSP approach such as described in connection with one or more example embodiments herein. Subcomponents are denoised in process 1403 using an MDSP embodiment as described herein. Subcomponents that contain a majority of the energy of the respiration pattern are selected and combined to create an respiratory emphasis signal in process 1404, also using an MDSP embodiment as discussed herein. The emphasis signal may include frequency subbands matching the spectral energy of particular signal waves of interest or a subset of basis functions tuned to the signal wave or feature point of interest and its variations across a range of normal, perturbed, and pathological conditions. The emphasis signal is processed in 1405 using zero crossings or spectral analysis to compute respiratory parameters.

In another embodiment (e.g., relative to FIG. 14), wavelet related subcomponents are used to compute an emphasis signal. The specific subcomponents that are used are selected relative to one or more of the decomposition technique used, sampling rate, and the species from which the physiologic signal was recorded.

In some embodiments, the noise level of an ECG is measured using an embodiment described above, and zero crossings that occur too frequently during noisy segments are discarded (or simply not used). In another embodiment, the emphasis signal can be low-pass filtered prior to measurement of respiration rate and tidal volume. The tidal volume can be extracted by measuring peak and valley amplitude between valid zero crossings. In another embodiment, the tidal volume is computed as a function of area under the curve between valid zero crossings.

Figure 15:
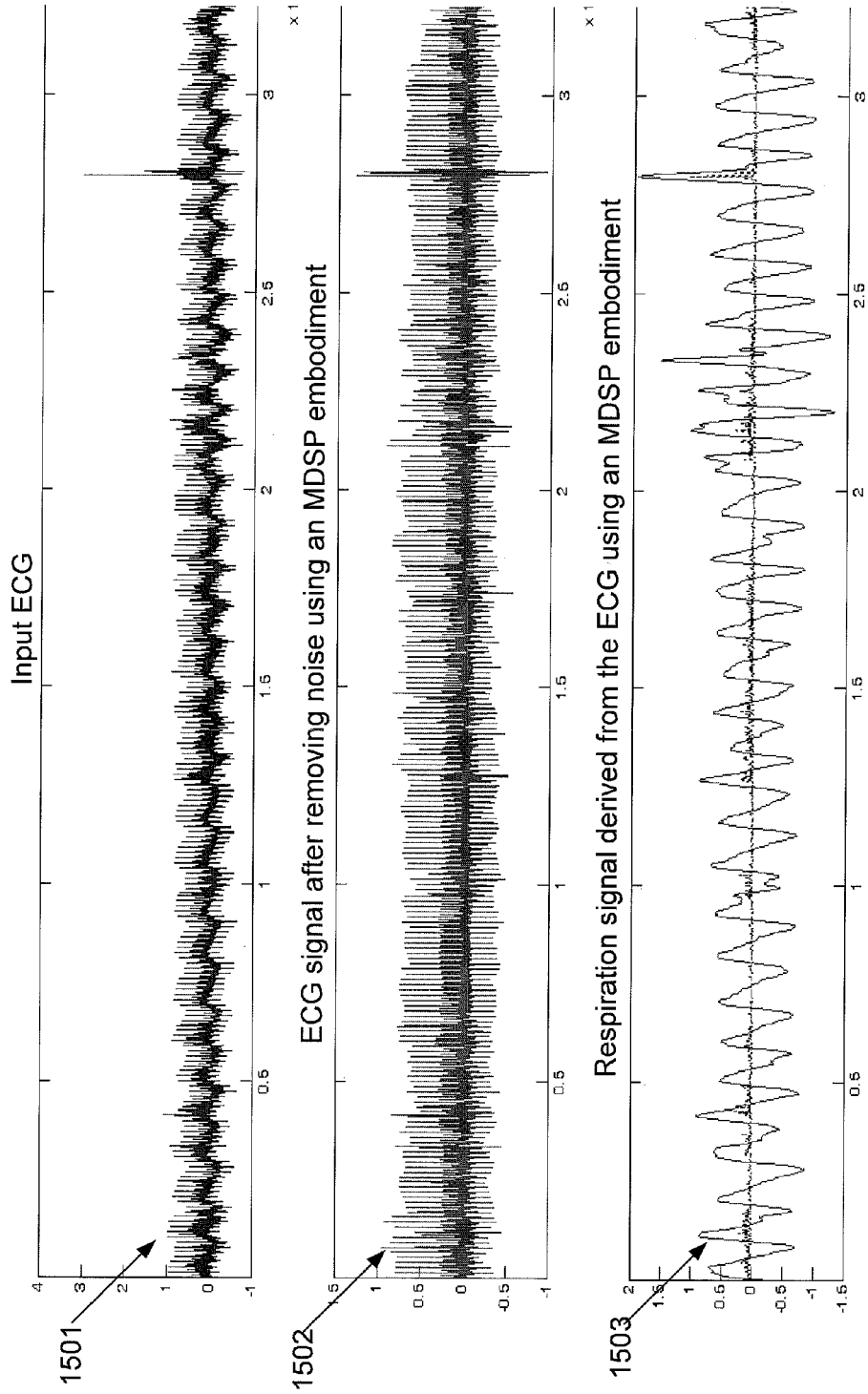
FIG. 15 shows an example of respiration signal extraction in an ECG recording, according to another example embodiment of the present invention.

FIG. 15 illustrates another example embodiment as directed to the processing of a primate ECG. Plot 1501 is a noisy input ECG, plot 1502 is an ECG denoised with a MDF-based approach as described herein, and plot 1503 is an extracted respiration emphasis signal. The residual noise level is measured and is shown on the bottom plot as a dotted line. This approach is used to assess the validity of the respiration signal. Zero crossings can be discarded or otherwise not used if the noise exceeds a predetermined threshold (e.g., as with the sample 23,500 in FIG. 15).

An additional MDSP embodiment is directed to detecting events in a physiological signal by combining aspects of feature point detection and signal source extraction as discussed herein, to detect cardiac abnormalities and arrhythmias of ventricular and atrial origin, such as ventricular fibrillation, tachycardia, bradycardia, atrial fibrillation and flutter, AV block and others. In one embodiment, the intervals between QRS complexes are computed to detect rate abnormalities indicative of tachycardia or bradycardia. In another embodiment, a transition to tachycardia and QRS complex morphology are evaluated to discriminate between sinus-, supra-ventricular or life-threatening ventricular tachycardia. In another embodiment, the ventricular rhythm statistics and separated atrial activity rate are evaluated to detect atrial fibrillation and flutter.

Figure 16:
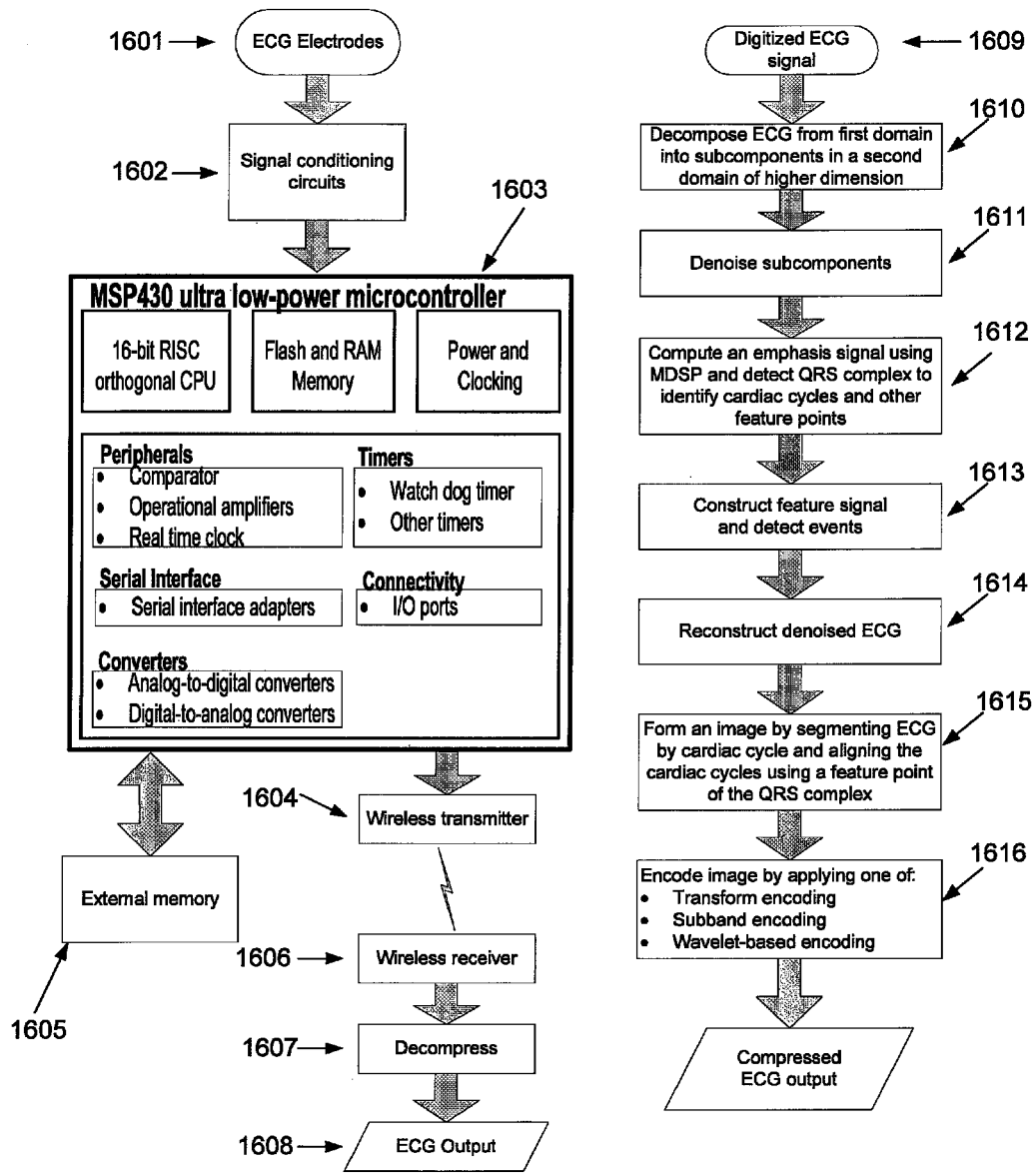
FIG. 16 illustrates an apparatus for efficient wireless communication of an ECG along with data flow diagrams for ECG signal compression, according to an example embodiment of the present invention.

Another embodiment of involving an MDSP-based approach is used to achieve efficient compression of quasi-periodic signals such as ECG signals, such as by suppressing noise while preserving signal morphology and providing accurate feature point detection. In one embodiment, arrhythmic events are detected and ECG traces corresponding to these events are compressed to reduce the data storage and transmission bandwidth required to communicate the signal to a location remote from the monitored subject. Referring to FIG. 16, an ECG signal sensed by electrodes 1601 is conditioned by signal conditioning circuits 1602. The digitized signal 1609 is decomposed in process 1610 and denoised in process 1611 using MDSP techniques described herein. An emphasis signal is computed and QRS complexes detected in process 1612 using an MDSP embodiment described herein. Cardiac events are detected in process 1613 using predefined thresholds for heart rate and morphology. The denoised ECG traces of detected arrhythmic events are reconstructed in process 1614. The ECG traces are segmented into cardiac cycles and are aligned using a feature point of the QRS complex in time to form an image in process 1615.

The two-dimensional (2D) image plot thus formed includes consecutive cardiac cycles in one dimension and the ECG signal of each cardiac cycle in the other dimension. An illustration of the 2D image is shown as a 3D plot by way of example in FIG. 17. Plot 1701 shows a 3D plot of sequential cardiac cycles with cardiac cycle length equalization (e.g., sequential RR intervals are padded by a constant value at the end of the cycle to ensure that all cardiac cycle lengths are equal). The redundancy between adjacent beats results in more efficient compression. However, due to physiologic factors such as respiration or rhythm disturbances the adjacent beat redundancy might be low. In the 3D ECG plot 1702, cardiac cycles are sorted by length (e.g., RR interval), resulting in smoother beat transitions that lead to more efficient compression. Accordingly, the image can be efficiently compressed by leveraging redundancies between adjacent cardiac cycles. In addition, redundancies across adjacent subbands or wavelet scales can be utilized by wavelet or cosine transforms of the image. Examples of techniques used in process 1616 that could be utilized to achieve efficient compression of the 2D image include transform, subband or wavelet based encoding techniques such as embedded zerotree wavelet (EZW) [36], set partitioning in hierarchical trees (SPIHT) [37], modified SPIHT [38] and embedded block coding with optimal truncation (EBCOT) encoding algorithms [39]. Compression ratios on the order of 15:1 to 20:1 with less than 5% distortion can be achieved using this technique on denoised ECG signals.

In another embodiment, a quasi-periodic signal is compressed by phase wrapping cardiac cycles and converting the source signals into a polar or cylindrical system of coordinates (38). Then the signal can be efficiently represented by a 3 dimensional plot of phase-aligned cardiac cycles and compressed.

In another embodiment a denoised ECG is compressed by computing a template QRS complex and subtracting it from detected normal QRS complexes. The residual signal has lower frequency content and can be compressed by a lossy compression technique that can include subsampling and quantization. The decompression technique makes use of lossless coding of the QRS template and QRS complex locations as well as lossy coding of the residual signal to reconstruct the ECG signal with small amount of distortion.

Figure 17:
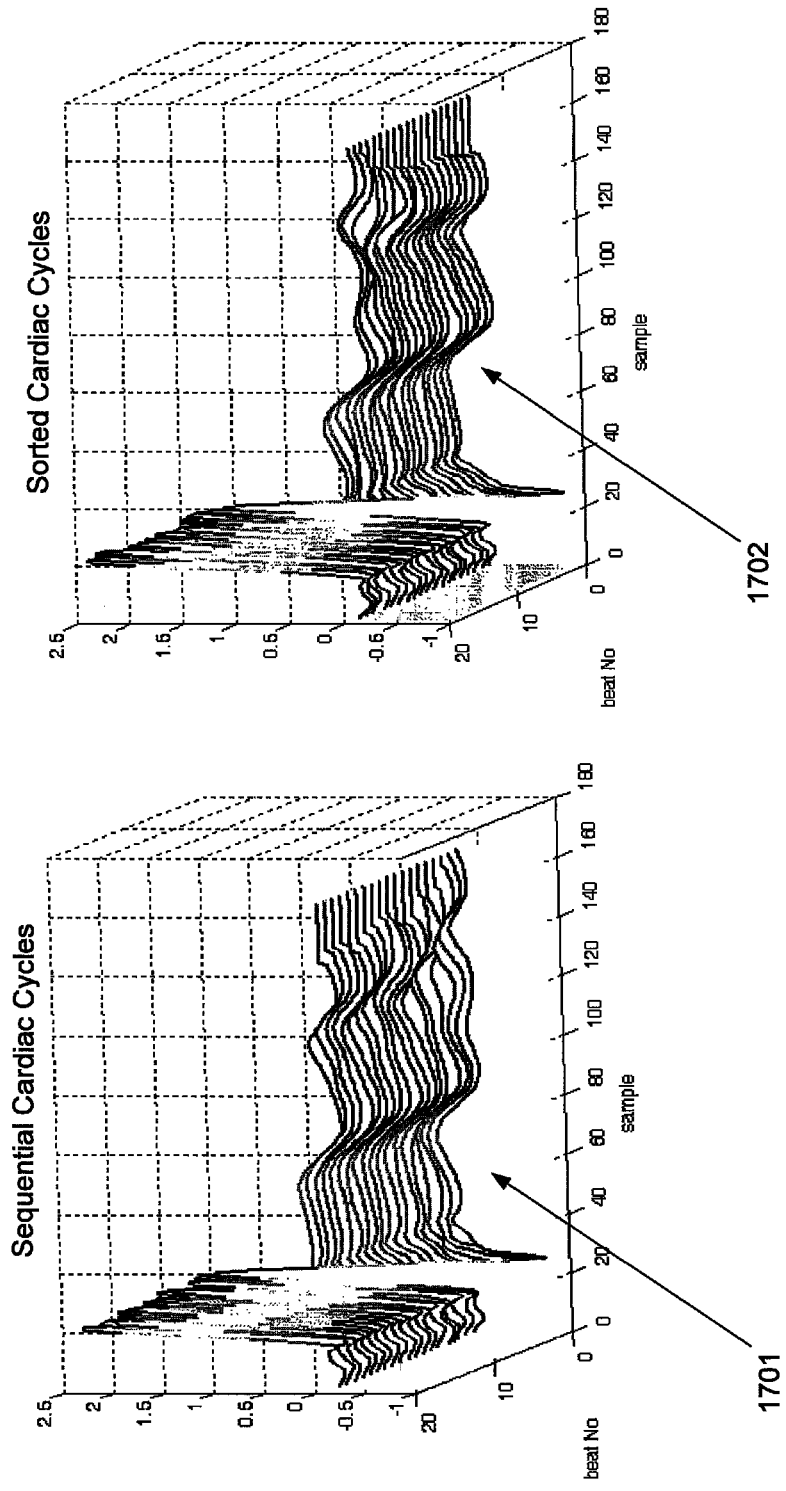
FIG. 17 shows an example of 3D ECG cycle plot as an intermediate step in ECG compression, in connection with another example embodiment of the present invention.

Other MDSP-based embodiments are used to compress blood pressure, pulse oximetry signals, respiration, heart sounds, and other pseudoperiodic signals. In order to achieve high levels of compression with any of these embodiments without introducing significant signal distortion, accurate QRS or cardiac cycle detection and effective noise suppression (denoising) are used. In some implementations, creating the intermediate representation of the signal that leverages redundancy between the cycles by sorting cycles by length, as in plot 1702 of FIG. 17, is used to achieve a high compression rate. Accurate cycle detection is used to mitigate the introduction of noise and artifacts into the reconstructed signal following compression and decompression.

Another embodiment is directed to an MDSP-based approach used to compress PNA signals and other non-quasi periodic signals, where the denoising provided by MDSP leads to a sparse signal as demonstrated in plot 1102 of FIG. 11. Note that the denoised signal is almost always near zero in the absence of a neural spike. The sparse signal is compressed using one or more compression schemes, such as direct time-domain coding or transform based coding [40]. In general, a compression scheme for a particular physiological signal is selected based upon the ability of a given scheme to leverage redundancies in the signal.

Figure 18:
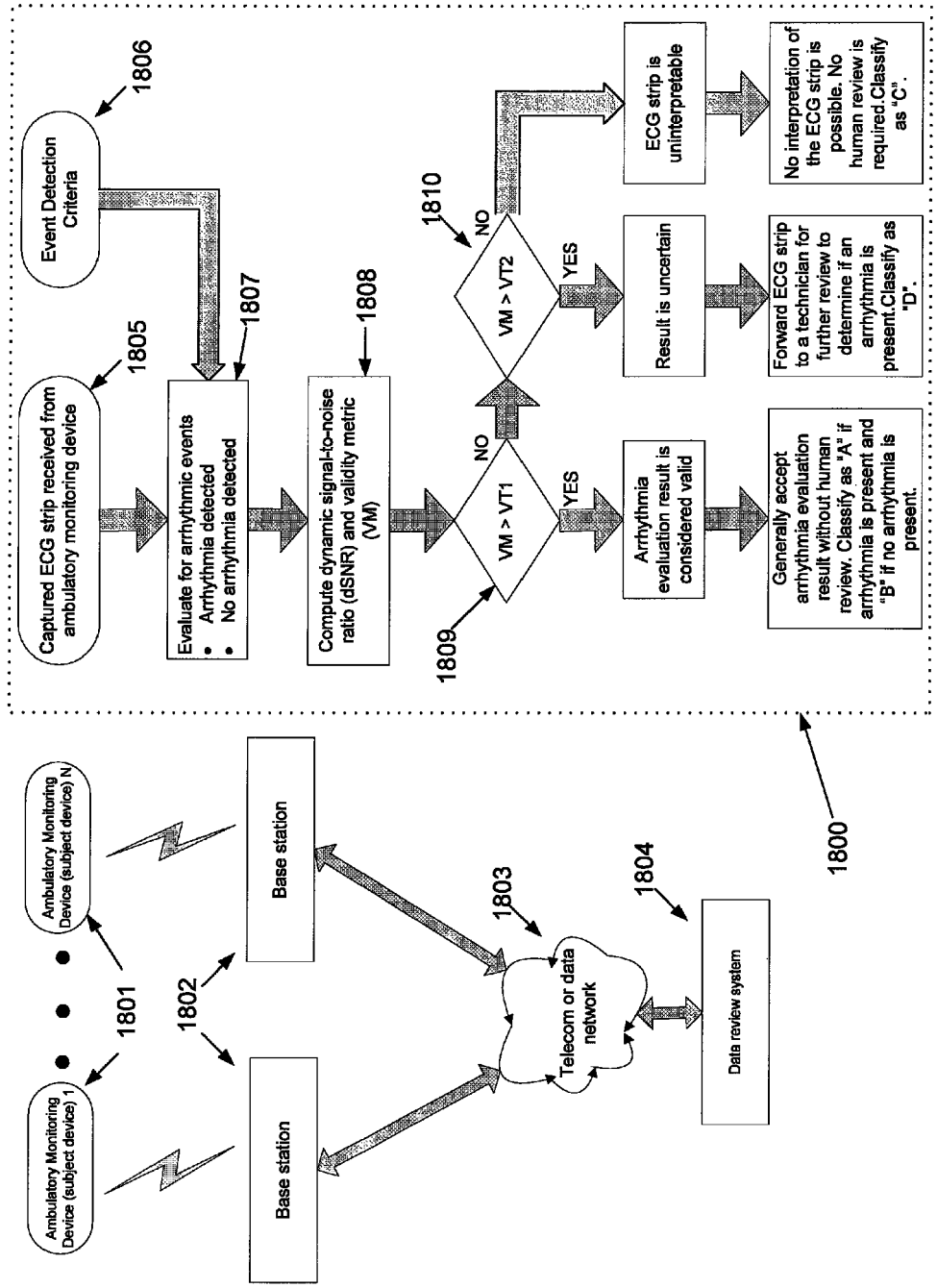
FIG. 18 shows a system for evaluating ECG strips captured by an ambulatory monitoring device along with data flow diagrams for determining if a strip contains an arrhythmia and assessing the validity of the result, according to an example embodiment of the present invention.

Referring to FIG. 18, another example embodiment is directed to using an MDSP-based approach to evaluate ECG strips captured by an ambulatory monitoring device 1801 with arrhythmic event detection capability. The captured ECG strips are forwarded to a data review system 1804 and evaluated using an MDSP-based algorithm 1800 implemented on a computing device in data review system 1804. Algorithm 1800 is used to evaluate the captured ECG strips 1805 and assign a classification to each strip. Each ECG strip is assigned one of four classifications using an MDSP-based approach for arrhythmia detection and validity, the classifications including: A) arrhythmia is present, B) no arrhythmia present, C) strip is uninterpretable, or D) uncertain (e.g., the ECG strip cannot be placed with confidence in classification A, B, or C). If an ECG is classified as D, an automatic indicator can be triggered to suggest human review to determine if an arrhythmia is present. For ECG strips falling in classifications B and C, no further review is needed. Depending upon the nature of the arrhythmia and the clinical care process, ECG strips falling in classification A may be reviewed by a person to assign a suggested diagnosis prior to forwarding to a decision maker. Using this approach and considering a relatively low percentage of the ECG strips evaluated requiring review, labor and costs associated with providing review services can be substantially reduced. In addition, the quality of review services can be improved, since an accurate computer-based algorithm can provide better consistency due to elimination of subjectivity.

The system shown in FIG. 18 includes ambulatory monitoring devices 1801, or subject devices, that are worn by patients being evaluated for a heart rhythm disorder or for research. Ambulatory monitoring device 1801 includes a computing circuit configured with an algorithm to evaluate the ECG signal from the patient and, if an arrhythmia is detected, capture an ECG strip containing the arrhythmia in memory. Such captured ECG strips may, for example, be one to five minutes in duration and stored in memory for later wireless communication to a base station 1802 (e.g., located in the patient's home), and from the base station 1802 to a data review system 1804 via telecom or data network 1803. The data review system 1804 may be located at a center where the received ECG strips can be reviewed, if necessary, to verify the presence of an arrhythmia or to suggest a diagnosis. The information derived from the ECGs is then packaged into a report which is forwarded to a researcher or clinician for use in decision making.

The results contained in a report may be provided to physicians, clinics, hospitals, or to organizations engaged in drug safety research, and can be delivered via a service provider system/review center that processes the resulting signals using data review system 1804, possibly in combination with trained healthcare personnel. Such a review center may provide services to a large number of clinics and physicians, or it may be housed within a clinic or a research facility and provide service to one or a small number of clinics or research groups or businesses.

In some embodiments, subject devices forward full-disclosure ECG recordings, and in yet other embodiments ECG strips of 10 second to 5 minutes are captured at regular intervals for analysis at the review center without regard to the content or nature of the ECG signal. In some embodiments, the subject device from which results are communicated as above is implanted in a patient. One type of implantable device is the Reveal XT from Medtronic of Minneapolis, Minn.

Flow chart 1800 in FIG. 18 shows an example embodiment directed to processing and evaluation of ECG strips received by data review system 1804. A captured ECG strip 1805 received at data review system 1804 is evaluated for the presence or absence of arrhythmias using an MDSP-based embodiment as described herein. Criteria 1806 input from a care provider or other decision maker is used by process 1807 to determine if an arrhythmia is present. Examples criteria 1806 include a heart rate above which a rhythm is considered to be a tachycardia, a heart rate below which a rhythm is considered to be a bradycardia, and a minimum duration atrial fibrillation (AF) episode required for an occurrence of AF to be reported as an arrhythmia. A dynamic signal-to-noise ratio (dSNR) is computed for the ECG strip in process 1808 as described herein. A validity metric (VM) may be additionally computed using the dSNR and signal morphology in process 1808. VM is compared to a Validity Threshold VT1 in decision point 1809. If VM exceeds VT1, the result is considered valid and captured ECG strip 1805 is classified "A" if process 1807 detected an arrhythmia and "B" if process 1807 did not detect an arrhythmia. If VM does not exceed VT1 at decision point 1809, then VM is compared to a threshold VT2 at decision point 1810 (VT2<VT1). If VM exceeds VT2, then the result is determined to be uncertain and the ECG strip is classified as "D" to indicate that review by a person should be carried out to determine whether an arrhythmia is present in the ECG strip. If VM does not exceed VT2, then the ECG strip is classified as uninterpretable ("C") and is considered uninterpretable because the noise level is too high to be evaluated by either human or by automated algorithm.

In some implementations, classifications A, B, and C are assigned with a degree of certainty, designated by the validity metrics VM1 and VM2, sufficiently high that any error in classification can be tolerated by the user (e.g., 90% likelihood). In some embodiments, the threshold of certainty of the classification, VM1 and VM2, is determined by the user. Captured ECGs assigned classification D (uncertain) generally include segments for which a computing circuit configured with executable software to carry out an MDSP-based processing approach is unable to make a determination of the rhythm as being classified as A, B, or C with a sufficiently high degree of certainty. Segments with classification D may, for example, contain a level of noise such that the denoised signal is not interpretable by the algorithm, but may be interpretable by a technician, or it may contain an unusual morphology that the software was unable to recognize.

The embodiments described here for analyzing physiologic signals may be implemented in a variety of platforms that include a logic circuit or computer, with reference made herein to a logic circuit or computing circuit being applicable to a variety of such circuits operating in accordance with one or more embodiments discussed herein. In one embodiment, a microprocessor (such as Pentium or Core microprocessors available from Intel of Santa Clara, Calif.) in a personal computer running an operating system such as Windows (available from Microsoft of Seattle, Wash.) or the Unix standard (set by The Open Group of San Francisco, Calif.) is used to execute programming to carry out MDSP-based functions as discussed herein. In another embodiment, a microcontroller suitable for low-power applications, such as the MSP 430 available from Texas Instruments of Dallas, Tex., is implemented to carry out MDSP-based functions as discussed herein. When a review center as described above is involved, a microprocessor may be used for simplicity of implementation and relatively low degree of concern about power consumption. Many implementations involving an MDSP-based approach in an ambulatory monitoring device employ a microcontroller (such as the MSP 430 above) to reduce/minimize power consumption. In other embodiments where power consumption and size are of high priority, implementation in a silicon-based state machine using a hardware description language such as VHDL may be useful.

Figure 19:
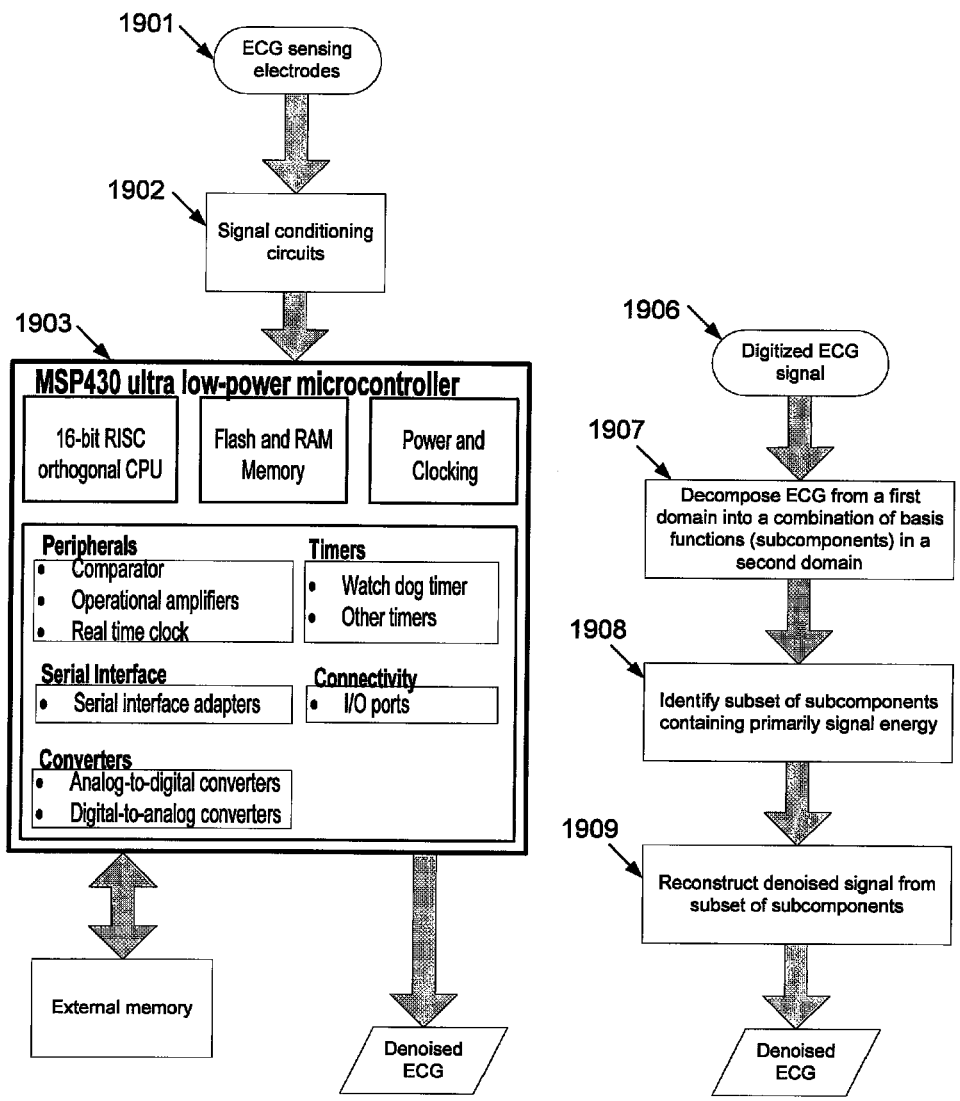
FIG. 19 illustrates an apparatus for improving the signal-to-noise ratio of an ECG signal and related flow chart for processing an ECG signal, according to an example embodiment of the present invention.

In some embodiments, referring to FIGS. 16 and 19, aspects of the present invention are implemented using a battery powered or passively-powered device (e.g., via radio frequency power) that is worn by or implanted within a human or animal subject. Depending upon the application and specific design requirements, referring to FIG. 18, various aspects of MDSP-based embodiments discussed herein may be partitioned between implementation within subject device 1801 and implementation within the data review system 1804.

Referring to FIG. 19, an apparatus for improving the signal-to-noise ratio of a physiological signal is shown, in accordance with another example embodiment. While referencing an ECG signal, the apparatus shown in FIG. 19 may be implemented with other signals such as blood pressure, respiration, photoplethysmography, blood glucose, blood flow, heart sounds, PNA, EMG, and EEG. In this example embodiment, ECG is sensed using either surface or implanted electrodes 1901. Signal conditioning circuits 1902 receives the signal from sensing electrodes 1901 and is conditioned to amplify and filter the signal to remove much of the noise outside the bandwidth of the ECG signal. Analog-to-digital conversion (ADC) is accomplished by an ADC on board a Texas Instruments MSP430 microcontroller 1903 (shown by way of example, and implementable with other processors).

Referring to the right side of FIG. 19, digitized signal 1906 is processed by computer instructions executed by a 16-bit RISC MCU of the MSP430 1903. The digitized signal 1906 is decomposed into a combination of basis functions (subcomponents) in a second domain of higher dimension than the first domain in process 1907. The dimension of the first domain is equal to the number of sensed ECG signals. Decomposition in process 1907 is performed using one of a discrete cosine transform, a wavelet related transform, a Karhunen-Loeve transform, a Fourier transform, a Gabor transform, and a filter bank. A subset of subcomponents containing primarily signal energy is identified using MDSP techniques (e.g., one or more of SSF, PCA, ICA, and πCA) in process 1908. In process 1909, a denoised signal is reconstructed from the subcomponents identified as primarily containing signal energy by performing the inverse of the transform used to decompose the signal. It should be noted that the concepts described here can also be applied to other MDSP-based embodiments beyond denoising, including feature point detection, event detection, and computing a dynamic signal-to-noise ratio to evaluate the accuracy of information extracted from a physiological signal.

Referring back to FIG. 16, another example embodiment involves using an MDSP-based approach for implementing a battery-powered apparatus capable of wirelessly communicating physiological signals. Referring to FIG. 18, this apparatus is one embodiment of subject device 1801. The example refers specifically to ECG signals, but a similar embodiment can be used for other pseudoperiodic physiological signals such as arterial blood pressure, respiration, blood oxygen saturation derived from PPG, heart sounds, and blood flow for example. In this example embodiment, ECG is sensed using either surface or implanted electrodes 1601. Signal conditioning circuits 1602 receive the signal from electrodes 1601 and amplify and filter the signal to remove much of the noise outside the bandwidth of the ECG signal. Analog-to-digital conversion (ADC) of the conditioned signal is accomplished by an ADC on board a Texas Instruments MSP430 microcontroller 1603.

Referring to the right side of FIG. 16, digitized signal 1609 is processed by computer instructions executed by the 16-bit RISC MCU of MSP430 1603. The MCU is in communication with offboard memory 1605 which may be used to provide additional data storage and for storage of computer instructions. The MCU is additionally in communication with wireless transmitter 1604 that can send compressed data to wireless receiver 1606 located remote from subject device 1801 of FIG. 18. Wireless receiver 1606 is further in communication with a logic circuit or computer that is configured to execute instructions to decompress the compressed signal in process 1607. In some embodiments the wireless transmitter 1604 and receiver 1606 may each be wireless transceivers capable of both sending and receiving data. An example of a wireless transceiver that may be used in connection with this embodiment is the CC2540 low-energy Bluetooth chip available from Texas Instruments (see above).

Referring to the data flow diagram on the right side of FIG. 16, digitized signal 1609 is decomposed in process 1610 into a combination of basis functions (subcomponents) in a second domain of higher dimension than the first domain. The dimension of the first domain is equal to the number of sensed ECG signals. Decomposition in process 1610 is performed using one of a discrete cosine transform, a wavelet related transform, a Karhunen-Loeve transform, a Fourier transform, a Gabor transform, and a filter bank. The subcomponents are denoised in process 1611 using MDSP techniques (e.g., one or more of SSF, PCA, ICA, and πCA) and a QRS emphasis signal is computed in process 1612 as a linear combination of a subset of denoised subcomponents containing QRS signal wave energy. The emphasis signal is evaluated to detect each QRS complex, as described herein, and a feature signal containing a series of feature points indicating the R-R interval of consecutive cardiac cycles is constructed in process 1613. The feature signal and morphology of the denoised ECG are evaluated in process 1613, as described herein, to detect arrhythmic events, such as bradycardia and tachycardia, and the denoised ECG strips containing arrhythmic events reconstructed in process 1614. The denoised ECG strips to be transmitted are compressed using processes 1615 and 1616. In process 1615, ECG strips are segmented by cardiac cycle and adjacent strips are aligned using a feature point of the QRS complex to form an image of a 3D plot similar to that shown in plot 1701 of FIG. 17. The image is subsequently encoded in process 1616 by, for example, applying transform encoding, subband encoding, or wavelet based encoding, after which the encoded image is saved in memory for later wireless transmission or it may be sent immediately.

In an alternate embodiment, instead of forming the image by aligning adjacent strips, the strips are arranged by cardiac cycle length, as in plot 1702 of FIG. 17. This results in additional redundancies in strips adjacent to each other in the image and hence results in more efficient compression.

In another embodiment a template QRS complex is computed and subtracted from detected normal QRS complexes. The residual signal is compressed by a lossy compression technique and the QRS template and QRS complex locations are compressed using lossless coding.

In order to meet power consumption requirements for implementation within a subject device for denoising and wireless communication, computer-executable instructions for carrying one an MDSP-based approach as discussed herein, stored as embedded code within the subject device, are configured to facilitate low-power implementation. In one embodiment, the computer instructions are optimized using integer or fixed point arithmetic and lifting or B-spline wavelet implementation [41] of a signal decomposition transform in order to reduce and/or minimize the number of clock cycles or machine states required. In such an embodiment, a portion of the computations required to analyze physiologic signals may be implemented within the subject device while others may be implemented in the data review system. In another embodiment, the subject device captures, denoises, and compresses the ECG of the subject and information is extracted from the ECG recording off-line in the data review system. The data review system may include a review function that facilitates human review of ECGs that were classified as uncertain by the algorithm.

Other embodiments are directed to a computer-based system or logic circuit, such as a computer operating using one or more processor circuits, which operate using executable modules. Each module (e.g., software-based module) is executable by a computer circuit to carry out one or more functions or processes as described herein. For instance, one such module may carry out MDSP computations upon input data such as ECG data, and transform the data into a denoised output. This transformation may involve, for example, the use of a software module that, when executed by a computer, carries out the steps as shown in FIGS. 1 and 2. Various other embodiments are directed to similar transformations, which may involve taking and processing one or more inputs to generate a transformed output useful for one or more of a variety of purposes, such as for detecting physiological conditions. Accordingly, the embodiments discussed herein may be carried out using such a system and/or computer circuit and related executable modules.

In one embodiment, and referring again to FIG. 19, a denoising function is implemented within a computerized apparatus configured to execute programming instructions. A digitized physiological signal 1906 is input to the computerized apparatus. The device computes a denoised output signal from the digitized input signal resulting in an improvement in SNR.

In one implementation, an input physiological signal sensed by ECG electrodes 1901 is a relatively noise-free single lead ECG recording from a human being or other mammal with a resting heart rate less than 150 BPM, contaminated with band-limited (0.5 to 100 Hz) white noise.

Following denoising in processes 1907, 1908, and 1909 using an MDSP embodiment, the SNR is improved by at least 5 decibels and the mean QRS amplitude for any 10 second interval of the recording is preserved within +/−10% of the mean QRS amplitude of the input signal for the same 10 second interval.

In this embodiment, the input ECG can be described as residing in a first domain having a dimension equal to the number of leads (e.g., channels) in the recording. For example, a recording consisting of a lead set (e.g., Leads I, II, and III), would have three dimensions. Referring to FIG. 19, the digitized input ECG 1906 is decomposed in process 1907 into a second domain of higher dimension than the first domain. Decomposition into the second domain results in generation of subcomponents that represent the information contained in the ECG signal. The dimension of the second domain is defined as the number of subcomponents representing each lead of the ECG multiplied by the number of leads. In one embodiment, decomposition performed in process 1907 is accomplished using a transform that largely achieves independence of the subcomponents. Independence of the subcomponents combined with qualification of the frequency content of each subcomponent facilitates a more precise identification of the association of a subcomponent or group of subcomponents with an aspect (e.g., T-wave) of the ECG signal.

In another embodiment, the subcomponents in the second domain are examined in process 1908, as described herein, based on their spatial distribution in time, to identify noise and other aspects of the ECG. In one embodiment, the spatial distribution is examined using spatially selective filtering, whereby aspects or waves of the ECG associated with wider frequency band, such as the QRS complex, are identified and preserved across the subcomponents. In this embodiment, subcomponents associated with high frequencies are preserved for a time window corresponding to the QRS complex, but are zeroed out in (or not used for) the time window corresponding to the remainder of the cardiac cycle. This allows the morphology of the QRS complex to be preserved, while removing the high frequency noise from the remainder of the cardiac cycle, where the primary signal content corresponds to lower frequencies. When the input signal is a multi-lead ECG, principal component analysis and independent component may be used in addition to spatially selective filtering to further enhance the independence of subcomponents.

In another example embodiment, referring to FIG. 20, spatially selective filtering is used to remove noise from an ECG. FIG. 20a (top) shows a cardiac cycle of an ECG waveform showing a P-wave, QRS complex 2001, T-wave, and U-wave, as processed in connection with this embodiment. The QRS complex is detected and, referring to FIG. 20b (middle), the time spanning the beginning of Q to end of S defines Time Window 2002. The remainder of the cardiac cycle is defined as Time Window 2003. Time Window 2002, containing the QRS complex, includes a wide range of frequencies ranging from low-frequencies to high-frequencies. For the ECG of a healthy human, this frequency range may span from 0.5 to 100 Hz. In order to preserve the morphology of the QRS complex, subcomponents in this frequency range are preserved and considered to be associated with a desired signal wave. In one embodiment, the beginning and end of Time Window 2002 are respectively defined by the onset of the Q-wave and the offset of the S-wave. In another embodiment, the beginning and end of Time Window 2002 are shifted somewhat earlier or later. Because the signal waves occurring in Time Window 2003 (e.g., P-wave, T-wave, U-wave) contain lower frequency components, the subcomponents comprising the low-frequencies, represented by region 2005, are preserved and the subcomponents comprising high-frequencies are removed since they are primarily are associated with noise.

In an alternate embodiment as shown in FIG. 20c, subcomponents associated with higher frequencies are removed in Time Windows 2002 and 2003 while retaining low-frequency components represented by region 2007. Those containing the higher frequencies are then added back during the time spanning Time Window 2002, as represented by region 2006, to restore the higher frequency components of the QRS complex. In some implementations, this approach is carried out to mitigate or avoid morphology distortion.

Figure 21:
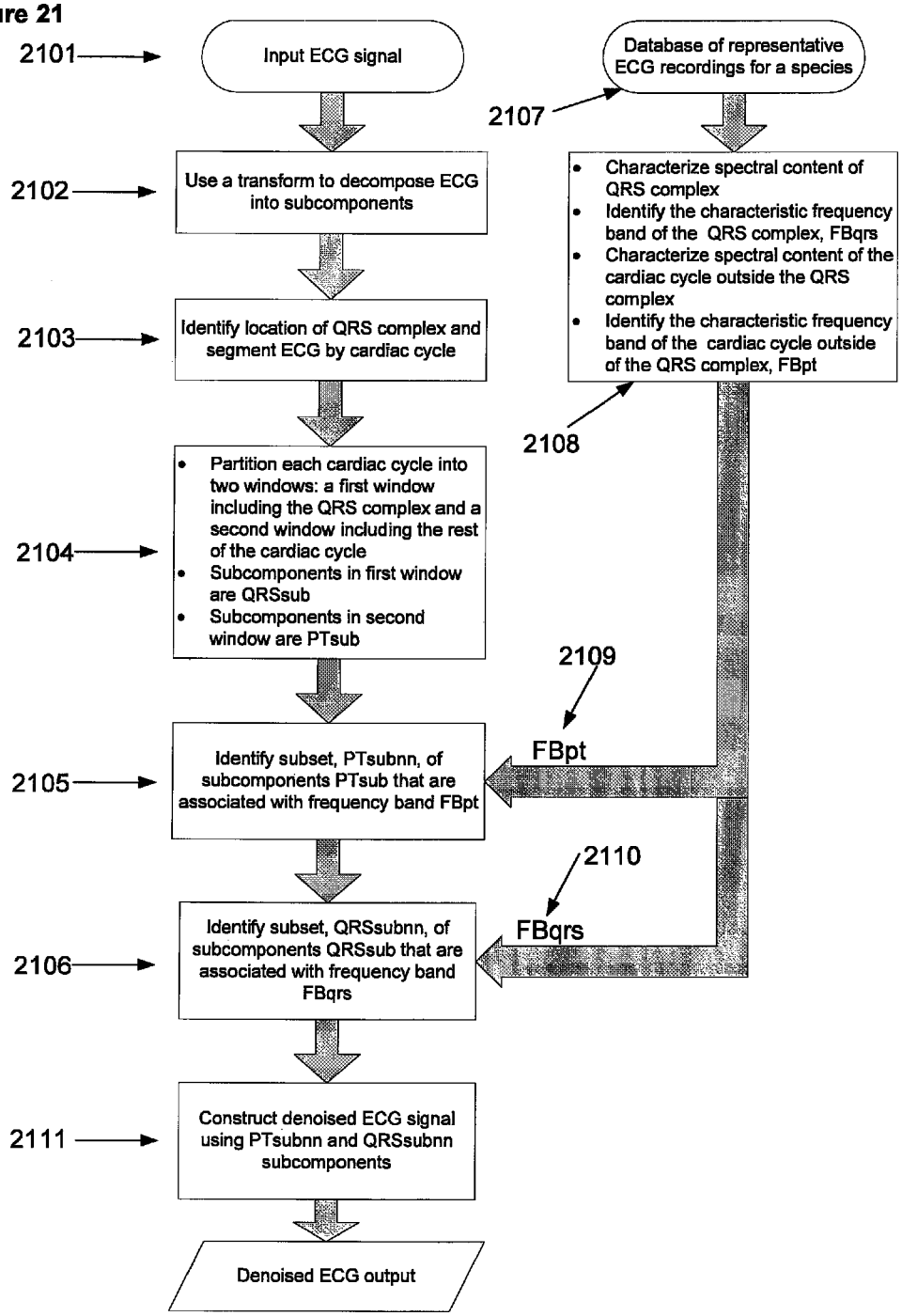
FIG. 21 illustrates a signal flow diagram for an embodiment of denoising applied to an ECG signal, according to another example embodiment of the present invention.

In one embodiment, and referring to FIG. 21, an input ECG signal 2101 is decomposed into subcomponents, as described herein, in process 2102. The QRS complex is identified in process 2103 using one of a number of techniques including thresholding, adaptive thresholding, and spatially selective filtering, as described herein. Following identification of the QRS complex the ECG is segmented by cardiac cycle using the QRS complex as a fiducial point. In one embodiment, each cardiac cycle is partitioned into two time windows in process 2104. Referring to FIG. 20, first time window 2002 begins at the onset of the Q-wave of the cardiac cycle and ends at the offset of the S-wave. The second time window 2003 begins at the offset of the S-wave and ends at the onset of the Q-wave of the next cardiac cycle. In other embodiments, the start and end times of windows 2002 and 2003 can differ somewhat from the above relative to the location of feature points of the QRS complex and some degree of overlap in the windows is also acceptable. In other embodiments, the cardiac cycle is partitioned into more than two time windows. For example, in an alternate embodiment a first time window includes the QRS complex, a second time window includes the T-wave, and a third time window includes the remainder of the cardiac cycle. The set of subcomponents present within time window 2002 are referred to as QRSsub and the set of subcomponents present in time window 2003 are referred to as PTsub.

In process 2105, subcomponents of the set PTsub are evaluated to identify subcomponent subset PTsubnn that overlaps the spectral content of (are associated with) a characteristic frequency band, FBpt, of the representative ECG signal present in window 2003. The value of a subcomponent represents the energy of the input ECG signal contained in a narrow range of frequencies and the subcomponent is said to be associated with this narrow range of frequencies.

Process 2105 relies on knowledge of the characteristic frequency band, FBpt, of the desired ECG signal in window 2003. FBpt is pre-identified using a database of representative ECG recordings for a species as described in process 2108.

In process 2106, subcomponents of the set QRSsub are evaluated to identify subcomponent subset QRSsubnn that overlaps the spectral content of (are associated with) a characteristic frequency band, FBqrs, of the representative ECG signal present in window 2002 of FIG. 20. In one embodiment, the input ECG signal is preprocessed to remove out-of-band noise in a signal conditioning circuit such as 1902 in FIG. 19, by a digital filter implemented in a computing or logic circuit, or a combination thereof. In one embodiment, where the energy of out-of-band noise in the input signal is negligible, the energy of the QRS subcomponents QRSsub and QRSsubnn essentially overlap.

Process 2106 relies on knowledge of the characteristic frequency band, FBqrs, of the desired ECG signal in window 2002. FBqrs is pre-identified using a database of representative ECG recordings for a species as described in process 2108.

The identification of the characteristic frequency bands for time window is performed by evaluating a database of representative ECG recordings for a species (input 2107). The database of representative ECG recordings is selected to represent a broad scope of ECG morphologies, heart rate, anomalies, noise characteristics, and pathologies. In the process 2108, the spectral content of the QRS complex is characterized and the characteristic frequency band of the QRS complex FBqrs is identified using spectral analysis techniques. The time window outside of the QRS complex in cardiac cycle is identified and the characteristic frequency band of the cardiac cycle outside of the QRS complex, FBpt, is identified using spectral analysis techniques. It should be noted that computing the characteristic frequency band is typically only performed once for the ECG sampled for a given species. Once FBpt and FBqrs are determined for a given species, they are used as parameters by the processes 2105 and 2106 and it is not necessary to recompute them.

In the process 2111 the identified target subcomponents contained in subset PTsubnn and subset QRSsubnn are combined and subjected to the inverse of the transform used in process 2102 to construct a denoised ECG signal.

Figure 22:
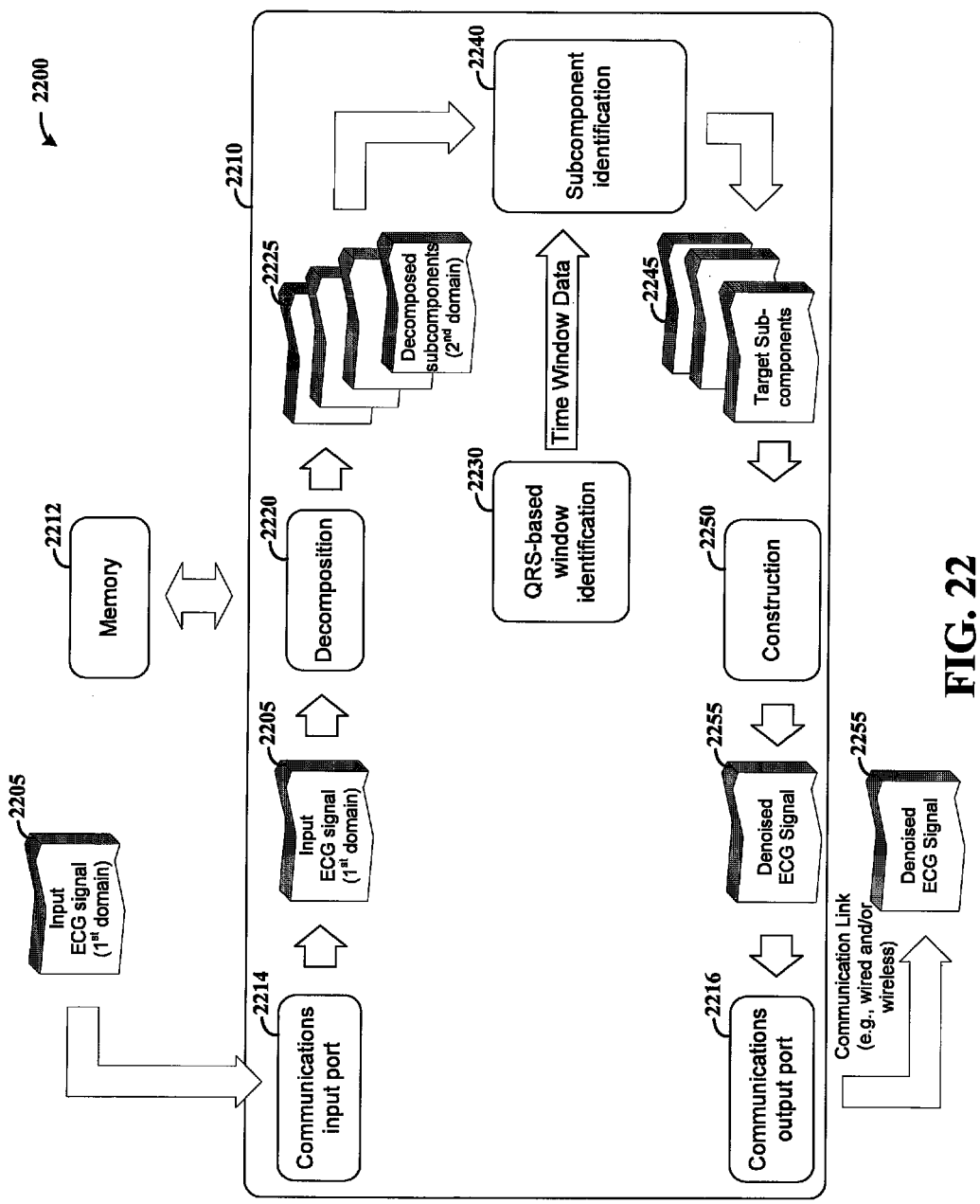
FIG. 22 illustrates a system for denoising an ECG signal, according to another example embodiment of the present invention.

FIG. 22 shows a system 2200 for computing a denoised ECG signal from an input signal including a desired ECG signal and noise, according to another example embodiment. The system includes a logic circuit 2210 and a memory circuit 2212. The memory circuit 2212 stores instructions that, when executed by the logic circuit, carry out the following steps. For illustration, FIG. 22 represents steps as carried out in the logic circuit 2210 with various blocks; however, various approaches for carrying out the steps may be implemented in connection with other embodiments. Moreover, the logic circuit 2210 may include two or more logic circuits, such as two or more processors that carry out different aspects of the respective steps. In addition, the various steps shown in FIG. 22 and described here may be implemented using one or more embodiments as discussed above, in connection with the other figures and otherwise.

Referring again to FIG. 22, an input ECG signal 2205, in a first domain, is received at a communications input port 2214, and is decomposed at block 2220 into subcomponents 2225 in a second domain (e.g., of higher dimension than the first domain as discussed hereinabove). QRS window-based identification is carried out at block 2230, at which a location of the QRS complex of a cardiac cycle in the ECG signal is identified. A first time window in the cardiac cycle that includes the QRS complex is identified, along with at least one time window in the cardiac cycle that does not include the QRS complex. The first time window and the at least one time window span the duration of the cardiac cycle.

At block 2240, and for each of the identified time windows, target subcomponents 2245 are identified as subcomponents that contain more desired ECG signal energy than noise energy. For example, when a particular subcomponent exhibits more energy associated with a desired ECG signal than energy not associated with such a signal, that subcomponent may be identified as a target subcomponent. The target subcomponents 2245 are used at block 2250 to construct a denoised physiological signal 2255.

The denoised ECG signal is then output via a communications output port 2216. This output may, for example, involve a wired or wireless communication, and may be carried out in accordance with one or more embodiments as described herein. In some implementations, some or all of the logic circuit 2210 is included as part of an implantable device, and carries out some or all of the steps in the implantable device, for generating the denoised physiological signal 2255. Using this approach, and as consistent with the above, the logic circuit 2210 can be implemented to significantly reduce the size of the denoised and compressed physiological signal 2255 (e.g., as relative to approaches that do not denoise in this manner), and facilitate the communication of the denoised and compressed physiological signal using less data and, correspondingly, lower power.

Those skilled in the art will appreciate that various alternative logic circuits or computing arrangements, including one or more processors and a memory arrangement configured with program code, would be suitable for carrying out the approaches as discussed herein, including those discussed in connection with FIG. 22 above, along with data structures for organizing the required data. Such computer code can be encoded in a processor executable format and may be stored on and/or provided via a variety of computer-readable storage media or delivery channels such as magnetic or optical disks or tapes, electronic storage devices, or as application services over a network. With specific reference to FIG. 22, the logic circuit 2210 (and memory 2212, where appropriate) may be implemented with separate components on a circuit board or may be implemented internally within an integrated circuit. When implemented internally within an integrated circuit, the logic circuit 2210 can be implemented as a microcontroller.

The architecture of the logic circuits, processors and computer type circuits as described herein depends on implementation requirements as would be recognized by those skilled in the art. In this context, these components may be one or more general purpose processors, or a combination of one or more general purpose processors and suitable co-processors, or one or more specialized processors (e.g., RISC, CISC, and pipelined).

Referring again to FIG. 22, the memory circuit 2212 may include multiple levels of cache memory and a main memory, and local and/or remote persistent storage such as provided by magnetic disks, flash, EPROM, or other non-volatile data storage. The memory circuit 2212 may be read or read/write capable. The logic circuit 2210 may store instructions (e.g., software) in the memory circuit 2210, read data from and stores data to the memory circuit 2212, and communicate with external devices through the input/output ports 2214 and 2216. These functions may be synchronized by a clock signal generator that may be part of the logic circuit 2210. The resources of the logic circuit 2210 may be managed by either an operating system, or a hardware control unit.

Referring to process 1907 in FIG. 19, example transforms that can be used for decomposing the signal into a second domain of higher dimension while enhancing, or maximizing, the independence of the subcomponents include a discrete cosine transform, a wavelet related transform, a Karhunen-Loeve transform, a Fourier transform, a Gabor transform, or a filter bank.

In another embodiment, referring to FIG. 16, a denoising function and a data compression function are implemented within a computerized apparatus (e.g., a logic circuit) configured to execute programming instructions. In this embodiment, denoising and compression of an ECG results in a reduction in bit rate required to retain the information in the signal. By compressing the ECG signal prior to wireless transmission, fewer bits can be used to achieve data transmission, and hence the power consumed in the transmission (e.g., a telemetry link) is reduced. This approach may also be implemented when storing ECG data (or other signal data) in memory, to reduce the data storage space required.

In a more particular example embodiment, a denoising and compression involves reducing the bit rate of a signal by a factor of 15:1 to 20:1, relative to the bit rate of input signal. For instance, such a compression factor can be achieved with a 16-bit digitized single lead ECG having a bit rate of 4,000 bits per second and sampled at 250 Hz, and with band-limited (0.5 to 100 Hz) noise corresponding to a SNR of 4 dB. The compressed signal is communicated to a receiving device where the compressed ECG signal is reconstructed. The denoising approach facilitates reconstructing QRS complex, from the compressed signal, having mean amplitude for any 10-second interval therein that differs from the mean amplitude of the input ECG by 10% or less. In one embodiment, communication is performed using a wireless link such as a Bluetooth transceiver. In some embodiments, events in the ECG, such as arrhythmias, are detected and compression and transmission of the ECG is triggered based on the presence of a detected event.

In this example embodiment, the input ECG is processed by the computerized apparatus to first denoise the signal, then detect cardiac cycles, segment the ECG by cardiac cycles and align them in time according to an identifiable fiduciary (e.g., a QRS peak), and form an image consisting of aligned cardiac cycles. The image is then encoded using a lossy compression technique such as transform encoding, subband encoding, or wavelet based encoding. The encoded image contains nearly all of the information in the denoised ECG, but does so with about 15-fold fewer bits. The encoded image is reconstructed at a receiver using the inverse of the transform used to encode the image, and ECG segments are reconnected to form a denoised version of the input signal. In one embodiment, denoising prior to compression is achieved in the same manner as described herein for the apparatus used for denoising.

In another embodiment, cardiac cycles are detected by computing a QRS emphasis signal and evaluating peaks, valleys, or slopes to identify the QRS complex. In another embodiment, the QRS complex is detected and a template QRS complex that is representative of the average complex is subsequently computed. The template is then subtracted from each QRS complex, creating a time series consisting of the resulting difference. The time series of residuals is subsequently encoded using a lossy compression technique such as transform encoding, subband encoding, or wavelet based encoding. The template QRS is encoded using a lossless transform such as Huffman encoding. This approach may be useful, for example, in connection with an embodiment in which a relatively simpler and less computationally intense compression technique is appropriate (e.g., where QRS morphology is not expected to change rapidly). Accordingly, the computational intensity of denoising and resulting signal quality/size can be weighed as a tradeoff, for implementation in various embodiments.

REFERENCES CITED

For general information regarding a variety of fields that may relate to one or more embodiments of the present invention, and for specific information regarding the application of one or more such embodiments, reference may be made to the following documents, which are fully incorporated herein by reference. Various ones of these references are further cited above via corresponding numerals, and may be implemented as such.

1. A. Hyvarinen and E. Oja. Independent component analysis: Algorithms and applications. Neural Networks, 13(4-5): 411-430, 2000.
2. K. S. Ball, L. Sirovich, L. R. Keefe, Dynamical eigenfunction decomposition of turbulent channel flow, International Journal for Numerical Methods in Fluids Volume 12, Issue 6, Date: 5 Apr. 1991, Pages: 585-604
3. S. Mallat, A Wavelet Tour of Signal Processing, Academic Press, 1999.
4. K. R. Rao and P. Yip, *Discrete Cosine Transform: Algorithms, Advantages, Applications* San Diego, Calif.: Academic, 1990.
5. Mallat, S. G., and Zhang, Z., Matching Pursuits with Time-Frequency Dictionaries, IEEE TSP(41), No. 12, December 1993, pp. 3397-3415.
6. Donoho, D. L.; Huo, X.; Uncertainty principles and ideal atomic decomposition., IEEE Transactions on Information Theory Volume 47, Issue 7, Nov. 2001 Page(s):2845-2862
7. Jong, G.-J. et. al. Single-channel signal separation using time-domain basis functions. IEEE Signal Processing Letters, vol. 10, Issue: 6, pp 168-171
8. Y. C. Pati, R. Rezaiifar, and P. S. Krishnaprasad, "Orthogonal matching pursuit: recursive function approximation with applications to wavelet decomposition," in *Asilomar Conference on Signals, Systems and Computers,* 1993, vol. 1, pp. 40-44.
9. S. S. Chen, D. L. Donoho, and M. A. Saunders, "Atomic decomposition by basis pursuit," *SIAM J. Scientific Computing*, vol. 20, no. 1, pp. 33-61, 1999.
10. Aharon, M.; Elad, M.; Bruckstein, A., K-SVD: An Algorithm for Designing Overcomplete Dictionaries for Sparse Representation, *IEEE Transactions on Signal Processing*, page(s): 4311-4322, Volume: 54, Issue: 11, Nov. 2006
11. M. Alghoniemy, Ah. Tewfik, "Reduced complexity bounded error subset selection," in *IEEE Int. Conf Acoustics, Speech* and Signal Processing (ICASSP), March. 2005, pp. 725-728.
12. K. Zhang, L. W. Chan, "An Adaptive Method for Subband Decomposition ICA", Neural Computation, vol. 18, no. 1, pp. 191-223, 2006.
13. Vaidyanathan, Multirate Systems and Filter Banks, Prentice Hall, 1993
14. L. Smith A tutorial on Principal Components Analysis, http://users.ecs.soton.ac.uk/hbr03r/pa037042.pdf
15. Aminghafari, M.; Cheze, N.; Poggi, J-M. (2006), "Multivariate de-noising using wavelets and principal component analysis," *Computational Statistics & Data Analysis,* 50, pp. 2381-2398
16. P. Comon, "Independent component analysis, a new concept?," Signal Process. Special Issue on Higher Order Statistics, vol. 36, no. 3, pp. 287-314, 1994.
17. J.-F. Cardoso, "High-order contrasts for independent component analysis," Neural Comput., vol. 11, no. 1, pp. 157-192, 1999.
18. Blaschke, T.; Wiskott, L.; CuBICA: independent component analysis by simultaneous third- and fourth-order cumulant diagonalization IEEE Transactions on Signal Processing, Volume 52, Issue 5, May 2004 Page(s):1250-1256
19. Hyvärinen, A. New approximations of differential entropy for independent component analysis and projection pursuit. In *Advances in Neural Information Processing Systems*, volume 10, pages 273-279.MIT Press.
20. Bell, A. and Sejnowski, T., An information-maximization approach to blind separation and blind deconvolution, *Neural Computation*, 7:1129-1159.
21. Cardoso, J.-F. Infomax and maximum likelihood for source separation. *IEEE Letters on Signal Processing,* 1997, 4, 112-114.

22. M. Zibulevsky, B. Pearlmutter, Blind source separation by sparse decomposition in a signal dictionary, Neural Computation 2001, v13, pp 863-882.
23. Todros, K.; Tabrikian, J.; Blind Separation of Independent Sources Using Gaussian Mixture Model IEEE Transactions on Signal Processing Volume 55, Issue 7, Part 2, July 2007 Page(s):3645-3658
24. Hyvärinen, A. Fast and robust fixed-point algorithms for independent component analysis. *IEEE Transactions on Neural Networks,* 10(3):626-634.
25. L. K. Saul and J. B. Allen, "Periodic component analysis: An eigenvalue method for representing periodic structure in speech.," in NIPS, [Online]. 2000, pp. 807-813. Available: http://www.cs.cmu.edu/Groups/NIPS/00papers-pub-on-web/SaulAllen.pdf
26. R Sameni, et. al. Multichannel electrocardiogram decomposition using periodic component analysis. IEEE Transactions on Biomedical Engineering, 2008 vol 55, no 8 pp 1935-1940
27. Mallat, S. and Zhong, S. 1992. Characterization of Signals from Multiscale Edges. IEEE Trans. Pattern Anal. Mach. Intell. 14, 7 (July 1992),
28. Mallat, S. G., Hwang, W. L., Singularity Detection and Processing with Wavelets, IEEE Transactions on Information Technology (38), 1991, pp. 617-643.
29. Xu, Yansun, et. al. Wavelet transform domain filters: a spatially selective noise filtration technique, IEEE transactions on image processing 1994, vol. 3, no6, pp. 747-758
30. Pan Q., Zhang L. Dai G. and et al. Two denoising methods by wavelet transform. IEEE Trans. on SP., 1999, 47(12): 3401-3406
31. Donoho, D. L., "Denoising by soft-thresholding," IEEE Trans. on Inf. Theory, 42 3, pp. 613-627, 1995
32. http://www.physionet.org/physiobank/database/#ecg
33. M. Hassan, J. Terrien, B. Karlsson, and C. Marque, "Spatial analysis of uterine EMG signals: Evidence of increased in synchronization with term," *Conf Proc IEEE Eng Med Biol Soc*, vol. 1, pp. 6296-9, 2009.
34. X. Li, X. Yao, J. Fox, and J. G. Jefferys, "Interaction dynamics of neuronal oscillations analysed using wavelet transforms," *J Neurosci Methods*, vol. 160, pp. 178-85, Feb. 15 2007.
35. http://www.physionet.org/physiobank/database/mitdb/
36. M. L. Hilton. Wavelet and wavelet packets compression of electrocardiogram. IEEE Transactions on Biomedical Engineering, 44(5):394-402, May 1997.
37. Z. Lu, D. Y. Kim, and W. A. Pearlman. Wavelet compression of ECG signals by the set partitioning in hierarchical trees algorithm. IEEE Transactions on Biomedical Engineering, 47(7):849-856, July 2000.
38. S. C. Tai, C. C. Sun, and W. C. Tan, "2-D ECG compression method based on wavelet transform and modified SPIHT," IEEE Trans. Biomed. Eng., vol. 52, no. 6, pp. 999-1008, June 2005
39. Marcellin M., et. al., An Overview of JPEG-2000, Proc. of IEEE Data Compression Conference, pp. 523-541, 2000.
40. K. Sayood, Introduction to Data Compression, Academic Press 2000.
41. K. G. Oweiss, A. Mason, Y. Suhail, A. M. Kamboh and K. E. Thomson "A scalable wavelet transform VLSI architecture for real-time signal processing in high-density intracortical implants", IEEE Trans. Circuits Syst. I, vol. 54, pp. 1266 2007.
42. Martinez J-P, et. al. A wavelet-based ECG delineator: Evaluation on standard databases. IEEE transactions on biomedical engineering 2004, vol. 51, no4, pp. 57
43. R Sameni, et. al. A nonlinear Bayesian filtering framework for ECG denoising. IEEE transactions on biomedical engineering, vol 54, n 012, pp 2172-2185, 2007
44. S. Paredes, T. Rocha, P. de Carvalho, J. Henriques, Atrial Activity Detection through a Sparse Decomposition Technique," vol. 2, pp. 358-362, 2008 International Conference on BioMedical Engineering and Informatics, 2008
45. D A Clunie, Extension of an open source DICOM toolkit to support SCP-ECG waveforms. 2nd OpenECG Workshop 2004, Berlin, Germany Based upon the above discussion and illustrations, those skilled in the art will readily recognize that various modifications and changes may be made to the present invention without strictly following the exemplary embodiments and applications illustrated and described herein. Such modifications and changes may include, for example, incorporating one or more aspects described in the above references and/or applying one or more embodiments thereto, or combining embodiments. These and other modifications do not depart from the true spirit and scope of the present invention, including that set forth in the following claims.

What is claimed is:

1. A method for computing a denoised ECG signal from an input signal including an ECG signal and noise, the method comprising:
    identifying a location of a QRS complex of a cardiac cycle in the input signal;
    identifying a first time window in the cardiac cycle that includes the QRS complex;
    identifying a second time window in the cardiac cycle that does not include the QRS complex; and
    removing a band of frequencies from the second time window.

2. The method of claim 1, wherein identifying the second time window includes identifying at least two time windows that do not include the QRS complex.

3. The method of claim 2, wherein identifying the at least two time windows that do not include the QRS complex includes identifying a time window that includes a T-wave of the cardiac cycle and another time window that includes a portion of the cardiac cycle that does not include the T-wave.

4. The method of claim 1, wherein
    identifying the first time window includes identifying the first time window having a beginning based upon an onset of a Q-wave of the cardiac cycle and an ending based upon an offset of an S-wave of the cardiac cycle, and
    identifying the second time window includes identifying the second time window having a beginning based on the offset of the S-wave and an ending based on the onset of the Q-wave of a next cardiac cycle.

5. The method of claim 1, wherein the first and second time windows partially overlap one another.

6. The method of claim 1, wherein
    removing the band of frequencies from the second time window includes removing a band of frequencies by spatially selective filtering the input signal, and
    identifying the location of the QRS complex of the cardiac cycle in the input signal includes identifying the QRS locations by spatially selective filtering the input signal.

7. The method of claim 1, wherein removing the band of frequencies from the second time window includes removing a band of frequencies corresponding to frequencies outside of a P-wave frequency range and a T-wave frequency range for the cardiac cycle, by filtering the input signal.

8. The method of claim 7, wherein
identifying the second time window includes identifying at least two time windows that do not include the QRS complex, and
filtering the input signal includes applying different filtering characteristics for filtering repolarization activity corresponding to the T-wave frequency range and for filtering atrial activity corresponding to the P-wave frequency range.

9. The method of claim 1, wherein removing the band of frequencies from the second time window includes removing a band of frequencies predominantly associated with noise.

10. The method of claim 1, wherein removing the band of frequencies from the second time window includes removing at least two distinct bands of frequencies.

11. The method of claim 1 wherein removing the band of frequencies from the second time window includes:
decomposing the input signal into subcomponents;
identifying target subcomponents in the second time window as subcomponents that contain more energy within a band of frequencies characteristic of a desired ECG signal in the second time window than energy outside the band of frequencies characteristic of the desired ECG signal in the second time window; and
removing subcomponents in the second time window that are not target subcomponents.

12. The method of claim 1, wherein removing the band of frequencies from the second time window includes:
identifying a band of frequencies to be removed in the second time window based upon a band of frequencies characteristic of the ECG signal in the second time window,
computing a reference signal based upon locations of the first and second time windows, and
using the reference signal to adjust a transfer function of an adaptive filter, and thereafter using the adaptive filter to remove the identified band of frequencies from the second time window.

13. The method of claim 1, wherein at least one of identifying the first time window and identifying the second time window includes identifying the time windows based upon pseudoperiodic characteristics of the ECG signal.

14. The method of claim 1, wherein removing the band of frequencies includes removing the band of frequencies based upon pseudoperiodic characteristics of the ECG signal.

15. The method of claim 1, wherein at least one of identifying the first time window and identifying the second time window includes identifying the time windows based upon a time-based distribution of components of the input signal.

16. The method of claim 1, wherein removing the band of frequencies includes removing the band of frequencies based upon a time-based distribution of components of the input signal.

17. The method of claim 1, wherein at least one of identifying the first time window and identifying the second time window includes identifying the time windows based upon pseudoperiodic characteristics of the ECG signal and a time-based distribution of components of the input signal.

18. The method of claim 1, wherein removing the band of frequencies includes removing the band of frequencies based upon pseudoperiodic characteristics of the ECG signal and a time-based distribution of components of the input signal.

19. The method of claim 1, wherein removing the band of frequencies includes identifying components of the input signal that are associated with a desired ECG signal based upon a time-based distribution of the components, and removing a band of frequencies that does not include the components.

20. The method of claim 1, wherein removing the band of frequencies includes modifying the input signal to generate the denoised ECG signal as an output for processing at a computer.

21. The method of claim 1,
further including
partitioning a cycle of the input signal into the first and second time windows based upon a characteristic band of frequencies expected for the ECG signal within each of the at least two time windows,
identifying the locations of the at least two time windows based upon a location of at least two feature points of the cycle, and
identifying subcomponents in one of the time windows as subcomponents that contain more energy within the characteristic band of frequencies, than energy outside the characteristic band of frequencies; and
wherein removing a band of frequencies from the second time window includes removing the band of frequencies based upon the identified subcomponents.

22. The method of claim 1, wherein removing a band of frequencies from the second time window includes removing a band of frequencies having components of the input signal that have more noise energy than ECG signal energy.

23. The method of claim 1,
wherein the input signal has identifiable cycles that can be partitioned into time windows, each time window having an associated band of frequencies, and
further including partitioning the cardiac cycle into the first and second time windows, and identifying the second time window as a time window including noise subcomponents of the input signal as subcomponents that are not associated with a frequency band of a desired ECG signal.

24. The method of claim 1, wherein removing the band of frequencies includes comparing frequency content of subcomponents of the input signal within the at least one time window, identifying a characteristic band of frequencies via spectral analysis of a database containing recordings of representative ECG signals, and removing a band of frequencies based upon the identified characteristic band of frequencies.

25. The method of claim 1, further including decomposing the input signal from a first domain into subcomponents of the input signal in a second domain, wherein identifying the first time window includes identifying the first time window based upon subcomponents indicative of the QRS complex, and wherein identifying the second time window includes identifying the second time window based upon subcomponents indicative of the noise.

26. The method of claim 1, wherein removing the band of frequencies includes removing the band of frequencies based upon a time-frequency representation of spectral content distribution that varies synchronously with a feature point of the cardiac cycle.

27. A method for computing an atrial activity signal from an input signal including an ECG signal and noise, the method comprising:
decomposing the input signal from a first domain into subcomponents of the input signal in a second domain;
identifying a location of ventricular electrical activity of a cardiac cycle in the ECG signal;
identifying a primary time window in the cardiac cycle that includes ventricular electrical activity;
identifying at least one secondary time window in the cardiac cycle that does not include the ventricular electrical activity;

identifying target subcomponents in the at least one secondary time window that contain more energy within a band of frequencies characteristic of the atrial activity signal than energy outside the band of frequencies characteristic of the atrial activity signal; and constructing the atrial activity signal using at least one of the identified target subcomponents.

28. The method of claim 27, wherein ventricular electrical activity includes at least one of a QRS complex and a T-wave.

29. The method of claim 27, wherein decomposing the input signal includes using at least one of the following:
a discrete cosine transform;
a wavelet related transform;
a Karhunen-Loeve transform;
a Fourier transform;
a Gabor transform; and
a filter bank.

* * * * *